United States Patent
Fukuzaki et al.

(10) Patent No.: US 11,171,165 B2
(45) Date of Patent: Nov. 9, 2021

(54) PHOTOELECTRIC CONVERSION ELEMENT, IMAGING ELEMENT, OPTICAL SENSOR COMPRISING A PHOTOELECTRIC CONVERSION FILM CONTAINING A PREDETERMINED COMPOUND, AND COMPOUND

(71) Applicant: FUJIFILM Corporation, Tokyo (JP)

(72) Inventors: Eiji Fukuzaki, Kanagawa (JP); Tomoyuki Mashiko, Kanagawa (JP); Tomoaki Yoshioka, Kanagawa (JP); Koichi Iwasaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/015,067

(22) Filed: Sep. 8, 2020

(65) Prior Publication Data

US 2020/0411569 A1 Dec. 31, 2020

Related U.S. Application Data

(63) Continuation of application No. PCT/JP2019/012786, filed on Mar. 26, 2019.

(30) Foreign Application Priority Data

Mar. 28, 2018 (JP) .............. JP2018-062556
Nov. 30, 2018 (JP) .............. JP2018-225658

(51) Int. Cl.
  *H01L 51/42* (2006.01)
  *H01L 27/146* (2006.01)
(52) U.S. Cl.
  CPC ............ *H01L 27/146* (2013.01); *H01L 51/42* (2013.01)

(58) Field of Classification Search
  CPC ............ H01L 51/4253; H01L 51/0074; H01L 27/1462; H01L 27/146; H01L 51/0059;
  (Continued)

(56) References Cited

U.S. PATENT DOCUMENTS

| 5,030,708 | A | 7/1991 | Krutak et al. |
| 9,349,965 | B2 * | 5/2016 | Yofu .................... C07D 455/03 |

(Continued)

FOREIGN PATENT DOCUMENTS

| JP | 2006086160 | 3/2006 |
| JP | 2009135318 | 6/2009 |
| JP | 2009167348 | 7/2009 |

OTHER PUBLICATIONS

"Search Report of Europe Counterpart Application", dated Mar. 26, 2021, p. 1-p. 8.

(Continued)

*Primary Examiner* — Que Tan Le
(74) *Attorney, Agent, or Firm* — JCIPRNET

(57) ABSTRACT

The present invention provides a photoelectric conversion element including a photoelectric conversion film having a narrow half-width of absorption peak and an excellent photoelectric conversion efficiency, and an imaging element, an optical sensor, and a compound. The photoelectric conversion element according to the present invention includes a conductive film, a photoelectric conversion film, and a transparent conductive film, in this order, in which the photoelectric conversion film contains a compound represented by Formula (1).

(Continued)

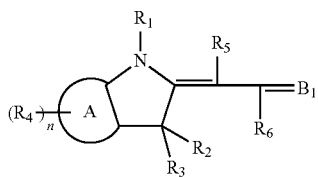

(1)

21 Claims, 19 Drawing Sheets

(58) Field of Classification Search
CPC . H01L 51/42; H01L 51/442; H01L 27/14621; H01L 27/14665
USPC ................................ 250/214.1, 208.1, 214 R
See application file for complete search history.

(56) References Cited

U.S. PATENT DOCUMENTS

| 2007/0085074 A1 | 4/2007 | Wang et al. |
| 2009/0140123 A1 | 6/2009 | Shen et al. |
| 2009/0184235 A1 | 7/2009 | Nomura et al. |

OTHER PUBLICATIONS

"International Search Report (Form PCT/ISA/210)" of PCT/JP2019/012786, dated Jun. 25, 2019, with English translation thereof, pp. 1-5.
"Written Opinion of the International Searching Authority (Form PCT/ISA/237)" of PCT/JP2019/012786, dated Jun. 25, 2019, with English translation thereof, pp. 1-14.

* cited by examiner

PHOTOELECTRIC CONVERSION ELEMENT, IMAGING ELEMENT, OPTICAL SENSOR COMPRISING A PHOTOELECTRIC CONVERSION FILM CONTAINING A PREDETERMINED COMPOUND, AND COMPOUND

CROSS-REFERENCE TO RELATED APPLICATIONS

This application is a Continuation of PCT International Application No. PCT/JP2019/012786 filed on Mar. 26, 2019, which claims priority under 35 U.S.C. § 119(a) to Japanese Patent Application No. 2018-062556 filed on Mar. 28, 2018 and Japanese Patent Application No. 2018-225658 filed on Nov. 30, 2018. Each of the above applications is hereby expressly incorporated by reference, in its entirety, into the present application.

BACKGROUND OF THE INVENTION

1. Field of the Invention

The present invention relates to a photoelectric conversion element, an imaging element, an optical sensor, and a compound.

2. Description of the Related Art

In recent years, development of an element having a photoelectric conversion film (for example, an imaging element) has progressed.

Regarding a photoelectric conversion element using a photoelectric conversion film, for example, JP2009-167348A discloses a photoelectric conversion element having a photoelectric conversion film containing a predetermined compound.

SUMMARY OF THE INVENTION

As one aspect of an imaging element, there is a laminated type imaging element in which a plurality of photoelectric conversion elements that receive different types of light are laminated. In a case where light is incident on the imaging element, a part of the incidence ray is absorbed by the photoelectric conversion elements arranged on the incident side, and the transmitted light is absorbed by the photoelectric conversion elements arranged further inside. In such an imaging element, since colors are easily separated, it is preferable that the absorption peak of each photoelectric conversion element has a narrow half-width.

The present inventors have examined the characteristics of the photoelectric conversion element specifically disclosed in Example section of JP2009-167348A, and have found that the half-width of the absorption peak of the photoelectric conversion film in the photoelectric conversion element is wide, and further improvement is necessary.

Also, the photoelectric conversion element is required to have excellent photoelectric conversion efficiency.

In view of the circumstances, an object of the present invention is to provide a photoelectric conversion element including a photoelectric conversion film having a narrow half-width of absorption peak and an excellent photoelectric conversion efficiency.

Another object of the present invention is to provide an imaging element, an optical sensor, and a compound.

The inventors of the present invention have conducted extensive studies on the above-described problems. As a result, the inventors have found that it is possible to solve the above-described problems by applying the compound having a predetermined structure to the photoelectric conversion film, and have completed the present invention.

(1) A photoelectric conversion element comprising a conductive film, a photoelectric conversion film, and a transparent conductive film, in this order, in which the photoelectric conversion film contains a compound represented by Formula (1) described below.

In Formula (1), $B_1$ is preferably a group represented by Formula (B-1) described below.

(2) The photoelectric conversion element according to (1), in which the compound represented by Formula (1) described below is a compound represented by Formula (2) described below or a compound represented by Formula (2b) described below.

(3) The photoelectric conversion element according to (2), in which the group represented by Formula (B-1-1) described below in the compounds represented by Formula (2) and Formula (2b) which are described below is groups represented by Formulae (J-1) to (J-5) which are described below.

(4) The photoelectric conversion element according to (3), in which the compound represented by Formula (1) described below is the compound represented by Formula (2) or Formula (2b) described below, and the group represented by Formula (B-1-1) described below in the compound represented by Formula (2) or Formula (2b) described below is the group represented by Formula (J-1) described below or the group represented by Formula (J-2) described below.

(5) The photoelectric conversion element according to any one of (2) to (4), in which the compound represented by Formula (1) described below is the compound represented by Formula (2b) described below, and $Rc_1$ represents the group represented by Formula (R-2) described below, the group represented by Formula (R-3) described below, the group represented by Formula (R-4) described below, a group represented by Formula (4A) described below, or a polycyclic aromatic ring which may have a substituent.

(6) The photoelectric conversion element according to (5), in which the compound represented by Formula (1) described below is the compound represented by Formula (2b) described below, and the group represented by Formula (B-1-1) described below in the compound represented by Formula (2b) described below is a group represented by Formula (J-1) described below, and $Rc_1$ represents the group represented by Formula (4A) described below, or a polycyclic aromatic ring which may have a substituent.

(7) The photoelectric conversion element according to (5) or (6), in which the compound represented by Formula (1) described below is a compound represented by Formula (2b-1) described below or a compound represented by Formula (2b-2) described below.

(8) The photoelectric conversion element according to (7), in which in Formulae (2b-1) and (2b-2) which are described below, $Rc_2$ represents a group represented by Formula (5A) described below, a group represented by Formula (5B) described below, or a naphthyl group which may have a substituent.

(9) The photoelectric conversion element according to any one of (1) to (8), in which the photoelectric conversion film further contains an n-type organic semiconductor, and has a bulk hetero structure formed in a state where the compound represented by Formula (1) described below and the n-type organic semiconductor are mixed.

(10) The photoelectric conversion element according to (9), in which the n-type organic semiconductor contains fullerenes selected from the group consisting of a fullerene and a derivative thereof.

(11) The photoelectric conversion element according to any one of (1) to (10), further comprising one or more interlayers between the conductive film and the transparent conductive film, in addition to the photoelectric conversion film.

(12) An imaging element comprising the photoelectric conversion element according to any one of (1) to (11).

(13) The imaging element according to (12), further comprising another photoelectric conversion element that receives light having a wavelength different from a wavelength of light received by the photoelectric conversion element.

(14) The imaging element according to (13), in which the photoelectric conversion element and the other photoelectric conversion element are laminated, and at least a part of incidence ray is transmitted through the photoelectric conversion element, and then is received by the other photoelectric conversion element.

(15) The imaging element according to (13) or (14), in which the photoelectric conversion element is a green photoelectric conversion element, and the other photoelectric conversion element includes a blue photoelectric conversion element and a red photoelectric conversion element.

(16) An optical sensor comprising the photoelectric conversion element according to any one of (1) to (11).

(17) A compound represented by Formula (1) described below.

(18) The compound according to (17), which is the compound represented by Formula (2) described below or a compound represented by Formula (2b) described below.

(19) The compound according to (18), which is the compound represented by Formula (2b) described below and $Rc_1$ represents the group represented by Formula (R-2) described below, the group represented by Formula (R-3) described below, the group represented by Formula (R-4) described below, a group represented by Formula (4A) described below, or a polycyclic aromatic ring which may have a substituent.

(20) The compound according to (19), which is a compound represented by Formula (2b-1) described below or a compound represented by Formula (2b-2) described below.

According to the present invention, it is possible to provide a photoelectric conversion element including a photoelectric conversion film having a narrow half-width of absorption peak and an excellent photoelectric conversion efficiency.

According to the present invention, it is possible to provide an imaging element, an optical sensor, and a compound.

DESCRIPTION OF THE PREFERRED EMBODIMENTS

Figure 1:
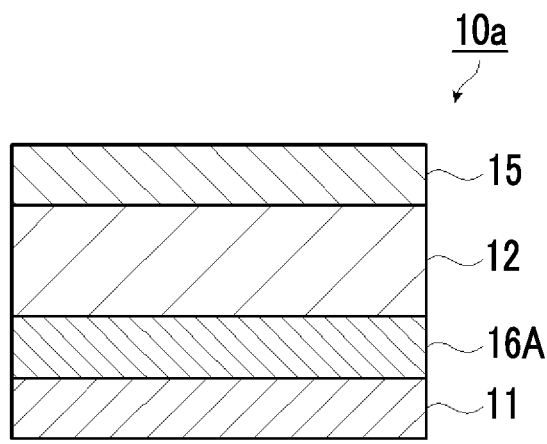
FIG. 1 is a schematic cross-sectional view showing an example of a configuration of a photoelectric conversion element.

Hereinafter, preferred embodiments of a photoelectric conversion element of the present invention will be described.

In the present specification, a substituent for which whether it is substituted or unsubstituted is not specified may be further substituted with a substituent (for example, a substituent W described below) within the scope not impairing an intended effect. For example, the expression of "alkyl group" refers to an unsubstituted alkyl group or an alkyl group with which a substituent (for example, a substituent W described below) may be substituted.

Further, in the present specification, examples of the "substituent" include groups exemplified as the substituent W described later. The "substituent" is preferably an alkyl group, an aryl group, or a heteroaryl group.

In the present specification, the "aromatic ring" means a ring exhibiting aromaticity. The "aromatic ring" may or may not have a substituent. The "aromatic ring" may be a "monocyclic aromatic ring" consisting of one ring exhibiting aromaticity, or a "polycyclic aromatic ring" in which two or more rings are condensed.

The "polycyclic aromatic ring" has two or more rings exhibiting aromaticity.

Examples of the aromatic ring may be either an aromatic hydrocarbon ring or an aromatic heterocyclic ring.

The substituents contained in the "aromatic ring (a monocyclic aromatic ring or a polycyclic aromatic ring)" may bond to each other to further form a ring.

Examples of the monocyclic aromatic ring include a monocyclic aromatic hydrocarbon ring such as a benzene ring, and a monocyclic aromatic heterocyclic ring such as a pyrrole ring, a furan ring, a thiophene ring, an imidazole ring, and an oxazole ring.

Examples of the polycyclic aromatic ring include a polycyclic aromatic hydrocarbon ring such as a naphthalene ring, an anthracene ring, a fluorene ring, and a phenanthrene ring, and polycyclic aromatic heterocyclic ring such as a quinoline ring and a benzothiophene ring.

In the present specification, the "non-aromatic ring" means a ring that does not exhibit aromaticity. The "non-aromatic ring" may or may not have a substituent. The "non-aromatic ring" may be a "monocyclic non-aromatic ring" consisting of one ring that does not exhibit aromaticity, or may be a "polycyclic non-aromatic ring" in which two or more rings that do not exhibit aromaticity are condensed and which does not exhibit aromaticity as a whole.

However, in the present specification, the substituents of the non-aromatic ring may bond to each other to form a ring, or the substituents of the non-aromatic ring may bond to each other to form an aromatic ring. Moreover, the non-aromatic ring may have an aromatic ring as a substituent (or a part thereof).

The "non-aromatic ring containing no aromatic structure" does not include an aromatic ring as a part of the non-aromatic ring. For example, in a non-aromatic ring containing no aromatic structure, the substituent (or part thereof) of the non-aromatic ring is not an aromatic ring, and a ring formed of the substituents of the non-aromatic ring bonding to each other is not an aromatic ring.

Examples of the non-aromatic ring include an aliphatic hydrocarbon ring (a cycloalkane ring and the like) and a cycloalkene ring.

In addition, in the present specification, the numerical range represented by "to" means a range including numerical values denoted before and after "to" as a lower limit value and an upper limit value.

In the present specification, a hydrogen atom may be a light hydrogen atom (an ordinary hydrogen atom) or a deuterium atom (a double hydrogen atom).

There is a feature of the photoelectric conversion element according to the embodiment of the present invention is that a bulky substituent is introduced into a compound represented by Formula (1) described below (hereinafter, also referred to as "specific compound") contained in the photoelectric conversion film. It is assumed that by introducing a bulky substituent in the specific compound (for example, at the positions of $R_1$ to $R_4$ in Formula (1)), steric repulsion between specific compounds occurs to the extent that excellent photoelectric conversion efficiency is obtained, and by suppressing the association of specific compounds in the photoelectric conversion film, the half-width of the absorption peak of the photoelectric conversion film is narrowed, and excellent photoelectric conversion efficiency is obtained.

FIG. 1 shows a schematic cross-sectional view of one embodiment of a photoelectric conversion element of the present invention.

A photoelectric conversion element 10a shown in FIG. 1 has a configuration in which a conductive film (hereinafter, also referred to as a lower electrode) 11 functioning as the lower electrode, an electron blocking film 16A, a photoelectric conversion film 12 containing the specific compound described below, and a transparent conductive film (hereinafter, also referred to as an upper electrode) 15 functioning as the upper electrode are laminated in this order.

Figure 2:
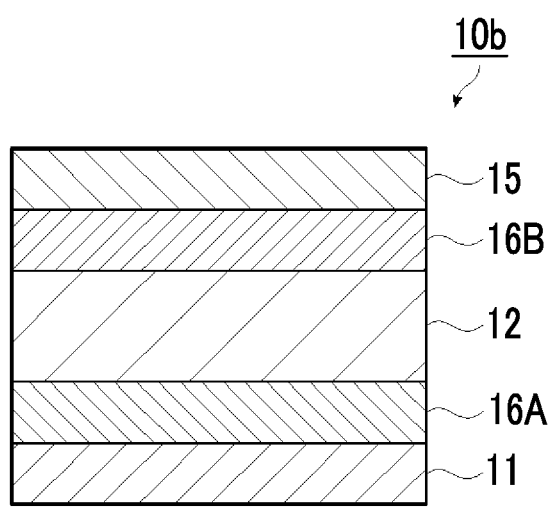
FIG. 2 is a schematic cross-sectional view showing an example of a configuration of a photoelectric conversion element.

FIG. 2 shows a configuration example of another photoelectric conversion element. A photoelectric conversion element 10b shown in FIG. 2 has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1 and 2 may be appropriately changed according to the application and the characteristics.

In the photoelectric conversion element 10a (or 10b), it is preferable that light is incident on the photoelectric conversion film 12 through the upper electrode 15.

In a case where the photoelectric conversion element 10a (or 10b) is used, the voltage can be applied. In this case, it is preferable that the lower electrode 11 and the upper electrode 15 form a pair of electrodes and the voltage of $1\times10^{-5}$ to $1\times10^{7}$ V/cm is applied thereto. From the viewpoint of performance and power consumption, the voltage to be applied is more preferably $1\times10^{-4}$ to $1\times10^{7}$ V/cm, and still more preferably $1\times10^{-3}$ to $5\times10^{6}$ V/cm. The voltage application method is preferable that the voltage is applied such that the electron blocking film 16A side is a cathode and the photoelectric conversion film 12 side is an anode, in FIGS. 1 and 2. In a case where the photoelectric conversion element 10a (or 10b) is used as an optical sensor, or also in a case where the photoelectric conversion element 10a (or 10b) is incorporated in an imaging element, the voltage can be applied by the same method. As described in detail below, the photoelectric conversion element 10a (or 10b) can be suitably applied to applications of the imaging element.

Hereinafter, the form of each layer constituting the photoelectric conversion element according to the embodiment of the present invention will be described in detail.

<Photoelectric Conversion Film>

The photoelectric conversion film is a film containing a specific compound as a photoelectric conversion material. By using the compound, a photoelectric conversion element including a photoelectric conversion film having a narrow half-width of absorption peak and an excellent photoelectric conversion efficiency can be obtained.

Hereinafter, the specific compound will be described in detail.

Formula (1) includes all geometric isomers that can be distinguished based on the C=C double bond constituted by a carbon atom to which $R_5$ (or $R_6$) bonds and a carbon atom adjacent thereto in Formula (1). That is, both the cis isomer and the trans isomer which are distinguished based on the C=C double bond are included in Formula (1).

The same applies to Formulae (2), (2b), (3) to (7), (2b-1), and (2b-2).

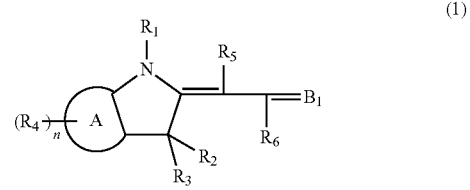

(1)

In Formula (1), $R_1$ represents an aryl group which may have a substituent, a heteroaryl group which may have a substituent, a group represented by Formula (R-1), a group represented by Formula (R-2), a group represented by Formula (R-3), or a group represented by Formula (R-4).

(R-1)

(R-2)

(R-3)

(R-4)

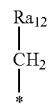

The carbon atoms of the aryl group are not particularly limited, but is preferably 6 to 30, more preferably 6 to 18, and still more preferably 6. The aryl group may have a monocyclic structure or a condensed ring structure (a fused ring structure) in which two or more rings are condensed.

As the aryl group, for example, a phenyl group, a naphthyl group, an anthryl group, or a fluorenyl group is preferable.

Examples of the substituent that the aryl group may have include the substituent W described below, and examples thereof include an alkyl group and a halogen atom, and an alkyl group is preferable.

The aryl group may have a plurality of types of substituents.

In a case where the aryl group has a substituent, the number of substituents that the aryl group has is not particularly limited, but is preferably 1 to 5, and more preferably 2 to 3.

The aryl group is preferably an aryl group which may be substituted with a substituent other than a halogen atom.

The carbon atoms of the heteroaryl group (a monovalent aromatic heterocyclic group) are not particularly limited, but is preferably 3 to 30, and more preferably 3 to 18.

The heteroaryl group includes a hetero atom in addition to a carbon atom and a hydrogen atom. Examples of the hetero atom include a sulfur atom, an oxygen atom, a nitrogen atom, a selenium atom, a tellurium atom, a phosphorus atom, a silicon atom, and a boron atom, and a sulfur atom, an oxygen atom, or a nitrogen atom is preferable.

The number of hetero atoms of the heteroaryl group is not particularly limited, but is preferably 1 to 10, more preferably 1 to 4, and still more preferably 1 to 2.

The number of ring members of the heteroaryl group is not particularly limited, but is preferably 3 to 8, more preferably 5 to 7, and still more preferably 5 to 6. The heteroaryl group may have a monocyclic structure or a condensed ring structure in which two or more rings are condensed. In a case of the condensed ring structure, an aromatic hydrocarbon ring having no hetero atom (for example, a benzene ring) may be included.

Examples of the heteroaryl group include a furyl group, a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a benzofuryl group, a thienyl group, a benzothienyl group, a dibenzofuryl group, a dibenzothienyl group, a pyrrolyl group, an indolyl group, an imidazopyridinyl group, and a carbazolyl group.

Among these, a furyl group, a thienyl group, a pyridyl group, a quinolyl group, an isoquinolyl group, or a carbazolyl group is preferable.

Examples of the substituent that the heteroaryl group may have include the same substituent that the aryl group may have.

In a case where the heteroaryl group has a substituent, the number of substituents that the heteroaryl group has is not particularly limited, but is preferably 1 to 5, and more preferably 1 to 3.

In Formula (R-1), $Ra_1$ represents a hydrogen atom or a substituent. The substituent represented by $Ra_1$ is preferably an alkyl group (preferably having 1 to 4 carbon atoms).

However, $Ra_1$ is none of an aryl group which may have a substituent or a heteroaryl group which may have a substituent.

* represents a bonding position.

In Formula (R-2), $Ra_2$ and $Ra_3$ each independently represent a substituent. The substituents represented by $Ra_2$ and $Ra_3$ are preferably an alkyl group (preferably having 1 to 4 carbon atoms), or an aryl group. The definition of the aryl group is the same as the definition of the aryl group described for $R_1$.

$Ra_2$ and $Ra_3$ may bond to each other to form a ring. More specifically, $Ra_2$ and $Ra_3$ may bond to each other via a single bond or a linking group to form a ring.

Examples of the ring formed by $Ra_2$ and $Ra_3$ bonding to each other include an aromatic ring (an aromatic hydrocarbon ring or an aromatic heterocyclic ring) and a non-aromatic ring.

* represents a bonding position.

In Formula (R-3), $Ra_4$ to $Ra_6$ each independently represent a substituent. The substituents represented by $Ra_4$ and $Ra_6$ are preferably an alkyl group (preferably having 1 to 4 carbon atoms), or an aryl group. The definition of the aryl group is the same as the definition of the aryl group described for $R_1$.

$Ra_4$ to $Ra_6$ may bond to each other to form a ring. More specifically, $Ra_4$ and $Ra_5$, $Ra_5$ and $Ra_6$, and $Ra_4$ and $Ra_6$ may respectively independently bond to each other to form a ring through a single bond or a linking group.

Examples of the type of ring formed include the rings exemplified as the ring formed by $Ra_2$ and $Ra_3$ bonding to each other.

* represents a bonding position.

In Formula (R-4), $Ra_{12}$ represents an aryl group which may have a substituent or a heteroaryl group which may have a substituent. The definitions of the aryl group and the heteroaryl group are the same as the definitions of the aryl group and the heteroaryl group described for $R_1$.

* represents a bonding position.

In a case where $R_1$ is a group other than the group represented by Formula (R-1), $R_1$ is preferably a group represented by Formula (R-2), a group represented by Formula (R-3), a group represented by Formula (R-4), a group represented by Formula (4A), or a polycyclic aromatic ring which may have a substituent, more preferably a group represented by Formula (4A), or a polycyclic aromatic ring which may have a substituent, and still more preferably a group represented by Formula (5A), a group represented by Formula (5B), or a naphthyl group which may have a substituent.

(4A)

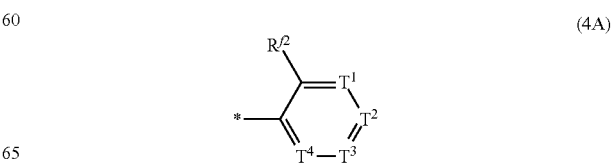

In Formula (4A), $T^1$ to $T^4$ each independently represent $CR^{e12}$ or a nitrogen atom. $R^{e12}$ represents a hydrogen atom or a substituent (an alkyl group having 1 to 4 carbon atoms, or a halogen atom). $R^{f2}$ represents an alkyl group (preferably having 1 to 4 carbon atoms), a cyano group, an aryl group which may have a substituent, or a heteroaryl group which may have a substituent.

The definitions of the aryl group and the heteroaryl group are the same as the definition of the aryl group described for $R_1$.

In a case where a plurality of $R^{e12}$s are present in Formula (4A), $R^{e12}$s may be the same as or different from each other, and $R^{e12}$s may bond to each other to form a non-aromatic ring containing no aromatic ring structure.

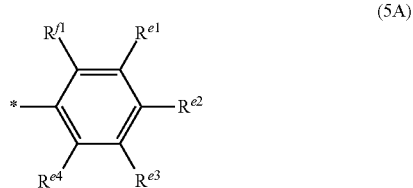

(5A)

In Formula (5A), $R^{e1}$ to $R^{e4}$ each independently represent a hydrogen atom or a substituent (an alkyl group having 1 to 4 carbon atoms, or a halogen atom). $R^{e1}$ to $R^{e4}$ may bond to each other to form a non-aromatic ring containing no aromatic ring structure. $R^{f1}$ represents an alkyl group (preferably having 1 to 4 carbon atoms).

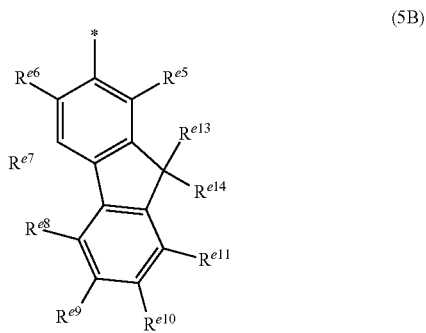

(5B)

In Formula (5B), $R^{e5}$ to $R^{e11}$, and $R^{e13}$ to $R^{e14}$ each independently represent a hydrogen atom or a substituent (an alkyl group having 1 to 4 carbon atoms). $R^{e5}$ to $R^{e11}$ and $R^{e13}$ to $R^{e14}$ may bond to each other to form a ring.

Among these, one or both of $R^{e1}$ to $R^{e11}$ preferably represent a substituent (an alkyl group having 1 to 4 carbon atoms).

A represents an aromatic ring.

Among these, from the viewpoint of obtaining a superior effect of the present invention, the aromatic hydrocarbon ring is preferable, and a naphthalene ring or a fluorene ring is more preferable.

$R_2$ and $R_3$ each independently represent a substituent. The substituents represented by $R_2$ and $R_3$ are preferably an alkyl group (preferably having 1 to 4 carbon atoms), or an aryl group. The definition of the aryl group is the same as the definition of the aryl group described for $R_1$.

The total number of carbon atoms contained in $R_2$ and $R_3$ is not particularly limited, is often 2 or more, and 4 or more is preferable from the viewpoint of obtaining a superior effect of the present invention. The total number of carbon atoms is not particularly limited, but is preferably 12 or less.

$R_2$ and $R_3$ may bond to each other to form a ring. More specifically, $R_2$ and $R_3$ may each independently bond to each other via a single bond or a linking group to form a ring. Examples of the type of ring formed include the rings exemplified as the ring formed by $Ra_2$ and $Ra_1$ bonding to each other.

$R_4$ to $R_6$ each independently represent a hydrogen atom or a substituent. The substituents represented by $R_4$ and $R_6$ are preferably an alkyl group (preferably having 1 to 4 carbon atoms), or an aryl group. The definition of the aryl group is the same as the definition of the aryl group described for $R_1$.

Among these, from the viewpoint of obtaining a superior effect of the present invention, $R_5$ and $R_6$ are preferably a hydrogen atom.

n represents an integer of 0 to 18. Among these, 0 to 5 is preferable, and 0 to 3 is more preferable, from the viewpoint of obtaining a superior effect of the present invention.

In a case where n is 2 or more, a plurality of $R_4$s may bond to each other to form a non-aromatic ring containing no aromatic ring structure, or a fluorene ring.

In a case where A is a benzene ring, n is 1 or more, at least one of $R_4$s represents a substituent having a Hammett's substituent constant $\sigma_p$ of 0.05 or less. Among these, the substituent is preferably a substituent having a Hammett's substituent constant $\sigma_p$ of −0.10 or less, from the viewpoint of obtaining a superior effect of the present invention. The lower limit of the Hammett's substituent constant $\sigma_p$ is preferably −0.80 or more.

Examples of the substituent having a Hammett's substituent constant $\sigma_p$ of 0.05 or less include an alkyl group, an alkenyl group (a cycloalkenyl group and a bicycloalkenyl group), an alkynyl group, an aryl group, a heteroaryl group (may be referred to as a heterocyclic group), a silyl group, a hydroxy group, an alkoxy group, an aryloxy group, a silyloxy group, a heterocyclic oxy group, an amino group (including an anilino group), a mercapto group, an alkylthio group, an arylthio group, and a heterocyclic thio group. Among these, a methyl group, an ethyl group, a propyl group, a butyl group, or a phenyl group is preferable.

Here, the Hammett's substituent constant $\sigma_p$ will be described. Hammett's rule is an experimental rule, which has been published in 1935 in order to quantitatively discuss the effect of substituents on the reaction or equilibrium of benzene derivatives by L. P. Hammett and is widely accepted today. The substituent constant $\sigma_p$ obtained by the Hammett's rule is described in detail in Chem. Rev. 1991, 91, 165-195, for example. In the present invention, although the substituents are limited or explained by Hammett's substituent constant $\sigma_p$, the limitation or explain does not mean that the literature-known value found in the above literature is limited only to a substituent, and even in a case where the value is unknown in the literature, the value also includes a substituent falling within the range in a case of being measured based on Hammett's rule.

The total number of carbon atoms contained in $R_1$ to $R_4$ is 5 or more. That is, the total number of carbon atoms contained in $R_1$, the carbon atoms contained in $R_2$, the carbon atoms contained in $R_3$, and the carbon atoms contained in $R_4$ is 5 or more. In a case where n is 0, the carbon atoms contained in $R_4$ is 0.

In a case where n is 2 or more, the total number of carbon atoms contained in $R_1$, the carbon atoms contained in $R_2$, the carbon atoms contained in $R_3$, and the carbon atoms of two or more $R_4$ is 5 or more.

Moreover, in a case where two $R_4$s bond to each other to form a ring, the total number of carbon atoms contained in $R_1$, the carbon atoms contained in $R_2$, the carbon atoms contained in $R_3$, and the carbon atoms contained in a ring formed by $R_4$s bonding to each other is 5 or more.

Among these, the total number of carbon atoms is preferably 7 or more, more preferably 9 or more, from the viewpoint of obtaining a superior effect of the present invention. The total number of carbon atoms is not particularly limited, but is preferably 30 or less.

In a case where $R_1$ represents an aryl group which may have a substituent, a heteroaryl group which may have a substituent, a group represented by Formula (R-2), a group represented by Formula (R-3), or a group represented by Formula (R-4), $B_1$ represents a group represented by Formula (B-1-1) or a group represented by Formula (B-1-2), and in a case where $R_1$ represents a group represented by (R-1), $B_1$ represents a group represented by Formula (B-2) or a group represented by Formula (B-3).

* represents a bonding position in Formulae (B-1-1), (B-1-2), (B-2), and (B-3).

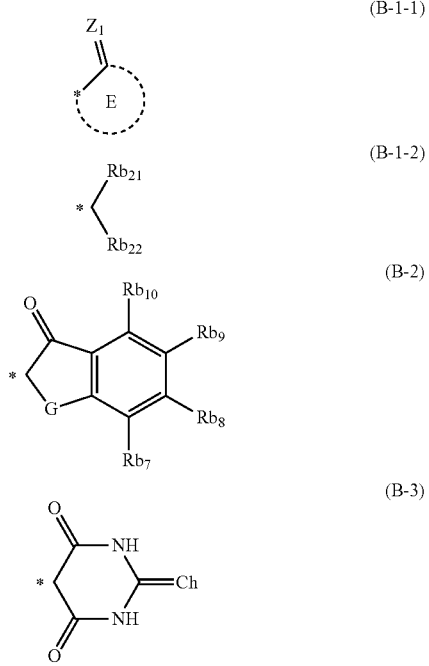

In Formula (B-1-1), E represents a ring which has at least two carbon atoms and may have a substituent.

E represents a ring containing at least two carbon atoms. The two carbon atoms are intended to mean a carbon atom bonding to $Z_1$ in Formula (B-1-1) by a double bond and a carbon atom adjacent to the carbon atom bonding to $Z_1$ by a double bond, and any carbon atom is an atom constituting E.

Among these, the carbon atoms of E are preferably 2 to 30, more preferably 2 to 20, and still more preferably 2 to 15. The above-described carbon atoms are a number containing two carbon atoms specified in Formula.

E may have a hetero atom, and examples thereof include a nitrogen atom, a sulfur atom, an oxygen atom, a selenium atom, a tellurium atom, a phosphorus atom, a silicon atom, and a boron atom, and a nitrogen atom, a sulfur atom, or an oxygen atom is preferable.

E may have a substituent.

The number of hetero atoms in E is preferably 0 to 10, more preferably 0 to 5, and still more preferably 0 to 3. The number of hetero atoms is a number that does not include the number of hetero atoms contained in $Z_1$.

E may or may not indicate aromaticity.

E may have a monocyclic structure or a condensed ring structure, but is preferably a 5-membered ring, a 6-membered ring, or a fused ring containing at least any one of a 5-membered ring or a 6-membered ring. The number of rings forming the fused ring is preferably 1 to 4, and more preferably 1 to 3.

$Z_1$ represents an oxygen atom, a sulfur atom, $NR_{Z1}$, or $CR_{Z2}R_{Z3}$. $R_{Z1}$ represents a hydrogen atom or a substituent, $R_{Z2}$ and $R_{Z3}$ each independently represent a cyano group or —$COOR_{Z4}$. $R_{Z4}$ represents an alkyl group which may have a substituent, an aryl group which may have a substituent, or a heteroaryl group which may have a substituent.

$Z_1$ is preferably an oxygen atom.

In Formula (B-1-2), $Rb_{21}$ and $Rb_{22}$ each independently represent a cyano group or —$COORb_{23}$. $Rb_{23}$ represents an alkyl group which may have a substituent, an aryl group which may have a substituent, or a heteroaryl group which may have a substituent.

In Formula (B-2), G represents —CO—, an oxygen atom, a sulfur atom, a selenium atom, a tellurium atom, —$NRb_1$—, —$CRb_2Rb_3$—, or —$SiRb_4Rb_5$—.

$Rb_1$ to $Rb_5$ and $Rb_7$ to $Rb_{10}$ each independently represent a hydrogen atom or a substituent.

$Rb_7$ to $Rb_{10}$ may bond to each other to form a ring. For example, $Rb_7$ and $Rb_8$, $Rb_8$ and $Rb_9$, and $Rb_9$ and $Rb_{10}$ may respectively independently bond to each other to form a ring through a single bond or a linking group.

Examples of the type of ring formed include the rings exemplified as the ring formed by $Ra_2$ and $Ra_1$ bonding to each other.

In Formula (B-3), Ch represents =$CRa_7Ra_8$, an oxygen atom, a sulfur atom, a selenium atom, or a tellurium atom.

$Ra_1$ and $Ra_8$ each independently represent a hydrogen atom or a substituent.

$Ra_7$ and $Ra_8$ may bond to each other to form a ring. More specifically, $Ra_7$ and $Ra_8$ may bond to each other via a single bond or a linking group to form a ring.

Examples of the type of ring formed include the rings exemplified as the ring formed by $Ra_2$ and $Ra_1$ bonding to each other.

In a case where $R_1$ represents an aryl group which may have a substituent, a heteroaryl group which may have a substituent, a group represented by Formula (R-2), a group represented by Formula (R-3), or a group represented by Formula (R-4), $B_1$ is preferably a group represented by Formula (B-1-1).

As the group represented by Formula (B-1-1), a group represented by Formula (B-1) is preferable from the viewpoint of obtaining a superior effect of the present invention.

In Formula (B-1), D represents —CO—, an oxygen atom, a sulfur atom, a selenium atom, a tellurium atom, —NRb$_1$—, —CRb$_2$Rb$_3$—, or —SiRb$_4$Rb$_5$—.

Rb$_1$ to Rb$_5$ each independently represent a hydrogen atom or a substituent.

E2 represents a ring containing at least two carbon atoms. The two carbon atoms refer to a carbon atom in a carbonyl group in Formula (B-1) and a carbon atom which is adjacent to the carbon atom in a carbonyl group, and both the carbon atoms are atoms constituting E2.

The carbon atoms of E2 are preferably 2 to 30, more preferably 2 to 20, and still more preferably 2 to 15. The above-described carbon atoms are a number containing two carbon atoms specified in Formula.

E2 may have a hetero atom, and examples thereof include a nitrogen atom, a sulfur atom, an oxygen atom, a selenium atom, a tellurium atom, a phosphorus atom, a silicon atom, and a boron atom, and a nitrogen atom, a sulfur atom, or an oxygen atom is preferable.

E2 may have a substituent.

The number of hetero atoms in E2 is preferably 0 to 10, more preferably 0 to 5, and still more preferably 0 to 3. The number of hetero atoms is a number that does not include the number of oxygen atoms contained in the carbonyl group constituting E2 specified in Formula (B-1).

E2 may or may not indicate aromaticity.

E2 may have a monocyclic structure or a condensed ring structure, but is preferably a 5-membered ring, a 6-membered ring, or a fused ring containing at least any one of a 5-membered ring or a 6-membered ring. The number of rings forming the fused ring is preferably 1 to 4, and more preferably 1 to 3.

As a group represented by Formula (B-1-1), groups represented by Formulae (J-1) to (J-5) are preferable, groups represented by Formulae (J-1) and (J-2) are more preferable, a group represented by Formula (J-1) is particularly preferable, from the viewpoint of obtaining a superior effect of the present invention.

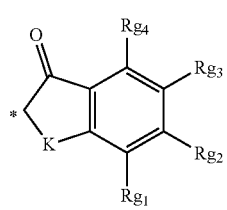

(J-1)

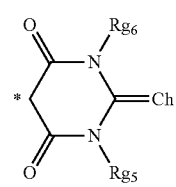

(J-2)

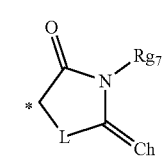

(J-3)

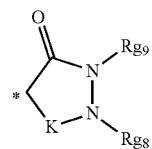

(J-4)

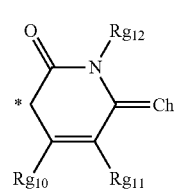

(J-5)

In Formula (J-1), Rg$_1$ to Rg$_4$ each independently represent a hydrogen atom or a substituent.

Rg$_1$ to Rg$_4$ may bond to each other to form a ring. For example, Rg$_1$ and Rg$_2$, Rg$_2$ and Rg$_3$, and Rg$_3$ and Rg$_4$ may respectively independently bond to each other to form a ring through a single bond or a linking group.

Examples of the type of ring formed include the rings exemplified as the ring formed by Ra$_2$ and Ra$_3$ bonding to each other.

K represents —CO—, an oxygen atom, a sulfur atom, a selenium atom, a tellurium atom, —NRb$_1$—, —CRb$_2$Rb$_3$—, or —SiRb$_4$Rb$_5$—. Rb$_1$ to Rb$_5$ each independently represent a hydrogen atom or a substituent.

In Formula (J-2), Rg$_5$ and Rg$_6$ each independently represent a hydrogen atom or a substituent.

Ch represents =CRa$_7$Ra$_8$, an oxygen atom, a sulfur atom, a selenium atom, or a tellurium atom. Ra$_7$ and Ra$_8$ each independently represent a hydrogen atom or a substituent.

Ra$_7$ and Ra$_8$ may bond to each other to form a ring. More specifically, Ra$_7$ and Ra$_8$ may each independently bond to each other via a single bond or a linking group to form a ring.

Examples of the type of ring formed include the rings exemplified as the ring formed by Ra$_2$ and Ra$_3$ bonding to each other.

In Formula (J-3), Rg$_7$ represents a hydrogen atom or a substituent.

Ch represents =CRa$_7$Ra$_8$, an oxygen atom, a sulfur atom, a selenium atom, or a tellurium atom. Ra$_7$ and Ra$_8$ each independently represent a hydrogen atom or a substituent.

Ra$_7$ and Ra$_8$ may bond to each other to form a ring.

L represents an oxygen atom, a sulfur atom, a selenium atom, or a tellurium atom.

In Formula (J-4), Rg$_8$ and Rg$_9$ each independently represent a hydrogen atom or a substituent.

Rg$_8$ and Rg$_9$ may bond to each other to form a ring. More specifically, Rg$_8$ and Rg$_9$ may each independently bond to each other via a single bond or a linking group to form a ring.

Examples of the type of ring formed include the rings exemplified as the ring formed by Ra$_2$ and Ra$_1$ bonding to each other.

K represents —CO—, an oxygen atom, a sulfur atom, a selenium atom, a tellurium atom, —NRb$_1$—, —CRb$_2$Rb$_3$—, or —SiRb$_4$Rb$_5$—. Rb$_1$ to Rb$_5$ each independently represent a hydrogen atom or a substituent.

In Formula (J-5), $Rg_{10}$ to $Rg_{12}$ each independently represent a hydrogen atom or a substituent.

$Rg_{10}$ and $Rg_{11}$ may bond to each other to form a ring.

Ch represents $=CRa_7Ra_8$, an oxygen atom, a sulfur atom, a selenium atom, or a tellurium atom. $Ra_7$ and $Ra_8$ each independently represent a hydrogen atom or a substituent. $Ra_7$ and $Ra_8$ may bond to each other to form a ring.

The specific compound does not have any of a carboxy group, a salt of a carboxy group, a phosphoric acid group, a salt of a phosphoric acid group, a sulfonic acid group, or a salt of a sulfonic acid group from the viewpoint of improving the vapor deposition suitability.

From the viewpoint of obtaining a superior effect of the present invention, as the specific compound, the compound represented by Formula (2), the compound represented by Formula (2b), the compound represented by Formula (5), the compound represented by Formula (6), or the compound represented by Formula (7) is preferable.

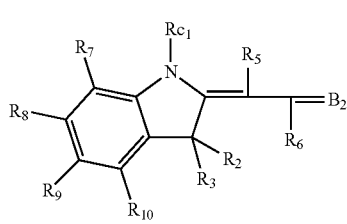

(2)

In Formula (2), the definitions of $R_2$, $R_3$, $R_5$, and $R_6$ are as described above.

$Rc_1$ represents an aryl group which may have a substituent, a heteroaryl group which may have a substituent, a group represented by Formula (R-2), a group represented by Formula (R-3), or a group represented by Formula (R-4). The definition and preferred embodiments of each group are as described above.

$R_7$ to $R_{10}$ each independently represent a hydrogen atom or a substituent. The substituents represented by $R_7$ and $R_{10}$ are preferably an alkyl group (preferably having 1 to 4 carbon atoms), or an aryl group. The definition of the aryl group is the same as the definition of the aryl group described for $R_1$.

$R_7$ to $R_{10}$ may bond to each other to form a non-aromatic ring containing no aromatic ring structure. For example, $R_7$ and $R_8$, $R_8$ and $R_9$, and $R_9$ and $R_{10}$ may respectively independently bond to each other to form a non-aromatic ring containing no aromatic ring structure through a single bond or a linking group.

At least one of $R_7$ to $R_{10}$ represents a substituent having a Hammett's substituent constant $\sigma_p$ of 0.05 or less. The definition and preferable range of the substituent having a Hammett's substituent constant $\sigma_p$ of 0.05 or less are as described above.

Among these, only one of $R_7$ to $R_{10}$ preferably represents a substituent having a Hammett's substituent constant $\sigma_p$ of 0.05 or less, from the viewpoint of obtaining a superior effect of the present invention.

The total number of carbon atoms contained in $Rc_1$, $R_2$, $R_3$, and $R_7$ to $R_{10}$ is 5 or more. That is, the total number of carbon atoms contained in $Rc_1$, the carbon atoms contained in $R_2$, the carbon atoms contained in $R_3$, the carbon atoms contained in $R_7$, the carbon atoms contained in $R_8$, the carbon atoms contained in $R_9$, and the carbon atoms contained in $R_{10}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

$B_2$ represents a group represented by Formula (B-1-1) described above.

However, the compound represented by Formula (2) has none of a carboxy group, a salt of a carboxy group, a phosphoric acid group, a salt of a phosphoric acid group, a sulfonic acid group, or a salt of a sulfonic acid group.

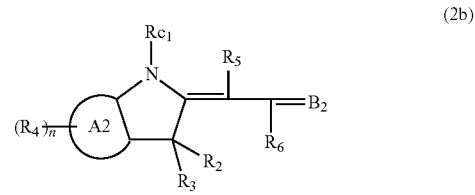

(2b)

In Formula (2b), the definitions of $Rc_1$, $R_2$, $R_3$, $R_4$, $R_5$, $R_6$, n, and $B_2$ are as described above.

Among these, in Formula (2b), $Rc_1$ is preferably a group represented by Formula (R-2), a group represented by Formula (R-3), a group represented by Formula (R-4), a group represented by Formula (4A), or a polycyclic aromatic ring which may have a substituent, and more preferably a group represented by Formula (5A), a group represented by Formula (5B), or a naphthyl group which may have a substituent.

A2 represents a polycyclic aromatic ring which may have a substituent. The polycyclic aromatic ring is preferably a naphthalene ring or a fluorene ring.

The total number of carbon atoms contained in $Rc_1$ and $R_2$ to $R_4$ is 5 or more.

That is, the total number of carbon atoms contained in $Rc_1$, the carbon atoms contained in $R_2$, the carbon atoms contained in $R_3$, and the carbon atoms contained in $R_4$ is 5 or more. In a case where n is 0, the carbon atoms contained in $R_4$ is 0.

In a case where n is 2 or more, the total number of carbon atoms contained in $R_1$, the carbon atoms contained in $R_2$, the carbon atoms contained in $R_3$, and the carbon atoms of two or more $R_4$ is 5 or more.

Moreover, in a case where two $R_4$s bond to each other to form a ring, the total number of carbon atoms contained in $R_1$, the carbon atoms contained in $R_2$, the carbon atoms contained in $R_3$, and the carbon atoms contained in a ring formed by $R_4$s bonding to each other is 5 or more.

Among these, the total number of carbon atoms is preferably 7 or more, more preferably 9 or more, from the viewpoint of obtaining a superior effect of the present invention. The total number of carbon atoms is not particularly limited, but is preferably 30 or less.

However, the compound represented by Formula (2b) has none of a carboxy group, a salt of a carboxy group, a phosphoric acid group, a salt of a phosphoric acid group, a sulfonic acid group, or a salt of a sulfonic acid group.

More specifically, the compound represented by Formula (2b) includes a compound represented by Formula (3) and a compound represented by Formula (4).

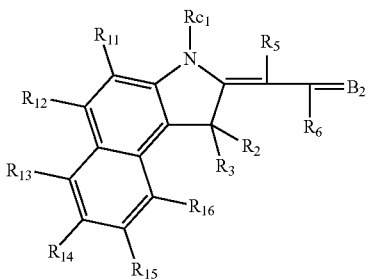

(3)

In Formula (3), the definitions of $Rc_1$, $R_2$, $R_3$, $R_5$, $R_6$, and $B_2$ are as described above.

$R_{11}$ to $R_{16}$ each independently represent a hydrogen atom or a substituent. The substituents represented by $R_{11}$ and $R_{16}$ are preferably an alkyl group (preferably having 1 to 4 carbon atoms), or an aryl group. The definition of the aryl group is the same as the definition of the aryl group described for $R_1$.

$R_{11}$ to $R_{16}$ may bond to each other to form a non-aromatic ring containing no aromatic ring structure, or a fluorene ring. For example, $R_{11}$ and $R_{12}$, $R_{12}$ and $R_{13}$, $R_{13}$ and $R_{14}$, $R_{14}$ and $R_{15}$, and $R_{15}$ and $R_{16}$ may respectively independently bond to each other to form a non-aromatic ring containing no aromatic ring structure through a single bond or a linking group, or a fluorene ring.

The total number of carbon atoms contained in $Rc_1$, $R_2$, $R_3$, and $R_{11}$ to $R_{16}$ is 5 or more. That is, the total number of carbon atoms contained in $Rc_1$, the carbon atoms contained in $R_2$, the carbon atoms contained in $R_3$, the carbon atoms contained in $R_{11}$, the carbon atoms contained in $R_{12}$, the carbon atoms contained in $R_{13}$, the carbon atoms contained in $R_{14}$, the carbon atoms contained in $R_{15}$, and the carbon atoms contained in $R_{16}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

However, the compound represented by Formula (3) does not have any of a carboxy group, a salt of a carboxy group, a phosphoric acid group, a salt of a phosphoric acid group, a sulfonic acid group, or a salt of a sulfonic acid group.

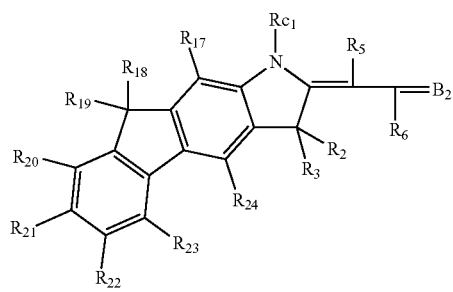

(4)

In Formula (4), the definitions of $Rc_1$, $R_2$, $R_3$, $R_5$, $R_6$, and $B_2$ are as described above.

$R_{17}$ to $R_{24}$ each independently represent a hydrogen atom or a substituent. The substituents represented by $R_{17}$ to $R_{24}$ are preferably an alkyl group (preferably having 1 to 4 carbon atoms), or an aryl group. The definition of the aryl group is the same as the definition of the aryl group described for $R_1$.

$R_{17}$ to $R_{24}$ may bond to each other to form a non-aromatic ring containing no aromatic ring structure, or a fluorene ring. For example, $R_{17}$ and $R_{18}$, $R_{18}$ and $R_{19}$, $R_{19}$ and $R_{20}$, $R_{20}$ and $R_{21}$, $R_{21}$ and $R_{22}$, $R_{22}$ and $R_{23}$, and $R_{23}$ and $R_{24}$ may respectively independently bond to each other to form a non-aromatic ring containing no aromatic ring structure through a single bond or a linking group, or a fluorene ring. In addition, $R_{18}$ and $R_{19}$ may bond to each other to form a fluorene ring. In this case, a 9,9'-spirobi[9H-fluorene] ring may be formed with the carbon atom to which $R_{18}$ and $R_{19}$ directly bond to each other as a Spiro atom.

The total number of carbon atoms contained in $Rc_1$, $R_2$, $R_3$, and $R_{17}$ to $R_{24}$ is 5 or more. That is, the total number of carbon atoms contained in $Rc_1$, the carbon atoms contained in $R_2$, the carbon atoms contained in $R_3$, the carbon atoms contained in $R_{17}$, the carbon atoms contained in $R_{18}$, the carbon atoms contained in $R_{19}$, the carbon atoms contained in $R_{20}$, the carbon atoms contained in $R_{21}$, the carbon atoms contained in $R_{22}$, the carbon atoms contained in $R_{23}$, and the carbon atoms contained in $R_{24}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

However, the compound represented by Formula (4) does not have any of a carboxy group, a salt of a carboxy group, a phosphoric acid group, a salt of a phosphoric acid group, a sulfonic acid group, or a salt of a sulfonic acid group.

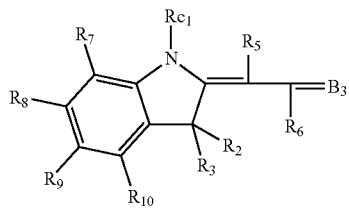

(5)

In Formula (5), the definitions of $R_2$, $R_3$, $R_5$, and $R_6$ are as described above.

In Formula (5), $Rc_2$ represents a group represented by Formula (R-1) described above.

$R_7$ to $R_{10}$ each independently represent a hydrogen atom or a substituent, $R_7$ to $R_{10}$ may bond to each other to form a non-aromatic ring containing no aromatic ring structure. At least one of $R_7$ to $R_{10}$ represents a substituent having a Hammett's substituent constant $\sigma_p$ of 0.05 or less.

The definitions and preferred ranges of $R_7$ to $R_{10}$ are the same as the definitions and preferred ranges described in Formula (2).

The total number of carbon atoms contained in $Rc_2$, $R_2$, $R_3$, and $R_7$ to $R_{10}$ is 5 or more. That is, the total number of carbon atoms contained in $Rc_2$, the carbon atoms contained in $R_2$, the carbon atoms contained in $R_3$, the carbon atoms contained in $R_7$, the carbon atoms contained in $R_8$, the carbon atoms contained in $R_9$, and the carbon atoms contained in $R_{10}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

$B_3$ represents a group represented by Formula (B-2) or a group represented by Formula (B-3).

However, the compound represented by Formula (5) has none of a carboxy group, a salt of a carboxy group, a phosphoric acid group, a salt of a phosphoric acid group, a sulfonic acid group, or a salt of a sulfonic acid group.

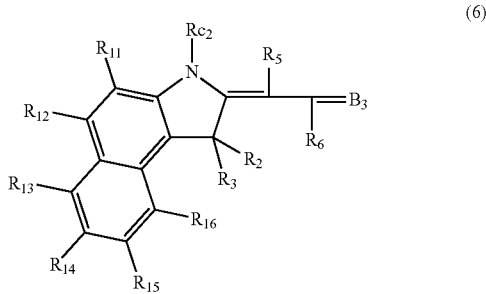

(6)

In Formula (6), the definitions of $Rc_2$, $R_2$, $R_3$, $R_5$, $R_6$, and $B_3$ are as described above.

In Formula (6), $Rc_2$ represents a group represented by Formula (R-1) described above.

$R_{11}$ to $R_{16}$ each independently represent a hydrogen atom or a substituent, $R_{11}$ to $R_{16}$ may bond to each other to form a non-aromatic ring containing no aromatic ring structure or a fluorene ring.

The definitions and preferred ranges of $R_{11}$ to $R_{16}$ are the same as the definitions and preferred ranges described in Formula (3).

The total number of carbon atoms contained in $Rc_2$, $R_2$, $R_3$, and $R_{11}$ to $R_{16}$ is 5 or more. That is, the total number of carbon atoms contained in $Rc_2$, the carbon atoms contained in $R_2$, the carbon atoms contained in $R_3$, the carbon atoms contained in $R_{11}$, the carbon atoms contained in $R_{12}$, the carbon atoms contained in $R_{13}$, the carbon atoms contained in $R_{10}$, the carbon atoms contained in $R_{15}$, and the carbon atoms contained in $R_{16}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

However, the compound represented by Formula (6) has none of a carboxy group, a salt of a carboxy group, a phosphoric acid group, a salt of a phosphoric acid group, a sulfonic acid group, or a salt of a sulfonic acid group.

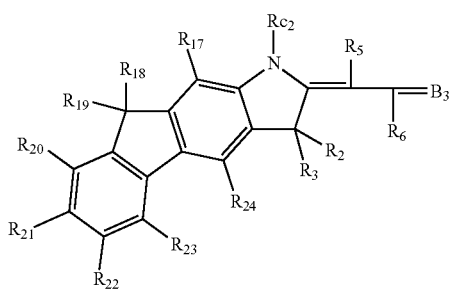

(7)

In Formula (7), the definitions of $Rc_2$, $R_2$, $R_3$, $R_5$, $R_6$, and $B_3$ are as described above. In Formula (7), $Rc_2$ represents a group represented by Formula (R-1) described above.

$R_{17}$ to $R_{24}$ each independently represent a hydrogen atom or a substituent, $R_{17}$ to $R_{24}$ may bond to each other to form a non-aromatic ring containing no aromatic ring structure or a fluorene ring.

The definitions and preferred ranges of $R_{17}$ to $R_{24}$ are the same as the definitions and preferred ranges described in Formula (4).

The total number of carbon atoms contained in $Rc_2$, $R_2$, $R_3$, and $R_{17}$ to $R_{24}$ is 5 or more. That is, the total number of carbon atoms contained in $Rc_2$, the carbon atoms contained in $R_2$, the carbon atoms contained in $R_3$, the carbon atoms contained in $R_{17}$, the carbon atoms contained in $R_{18}$, the carbon atoms contained in $R_{19}$, the carbon atoms contained in $R_{20}$, the carbon atoms contained in $R_{21}$, the carbon atoms contained in $R_{22}$, the carbon atoms contained in $R_{23}$, and the carbon atoms contained in $R_{24}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

However, the compound represented by Formula (7) has none of a carboxy group, a salt of a carboxy group, a phosphoric acid group, a salt of a phosphoric acid group, a sulfonic acid group, or a salt of a sulfonic acid group.

Among these, from the viewpoint of obtaining a superior effect of the present invention, an embodiment is preferable in which the compound represented by Formula (1) is at least one selected from the group consisting of the compound represented by Formula (3), the compound represented by Formula (4), the compound represented by Formula (6), and the compound represented by Formula (7), in the compound represented by Formula (3), the group represented by Formula (B-1-1) is the group represented by Formula (J-1) or the group represented by Formula (J-2), and in the compound represented by Formula (4), the group represented by Formula (B-1-1) is the group represented by Formula (J-1) or a group represented by Formula (J-2).

Also, an embodiment is more preferable in which the compound represented by Formula (1) is at least one selected from the group consisting of the compound represented by Formula (3), the compound represented by Formula (4), the compound represented by Formula (6), and the compound represented by Formula (7), in the compound represented by Formula (3), the group represented by Formula (B-1-1) is the group represented by Formula (J-1) or the group represented by Formula (J-2), and $Rc_1$ represents an aryl group which may be substituted with a substituent other than a halogen atom, a heteroaryl group which may have a substituent, the group represented by Formula (R-2), or the group represented by Formula (R-3), in the compound represented by Formula (4), the group represented by Formula (B-1-1) is the group represented by Formula (J-1) or the group represented by Formula (J-2), and $Rc_1$ represents an aryl group which may be substituted with a substituent other than a halogen atom, a heteroaryl group which may have a substituent, the group represented by Formula (R-2), or the group represented by Formula (R-3), in the compound represented by Formula (6), $B_3$ represents a group represented by Formula (B-2), and in the compound represented by Formula (7), $B_3$ represents a group represented by Formula (B-2).

Furthermore, an embodiment is still more preferable in which the compound represented by Formula (1) is at least one selected from the group consisting of the compound represented by Formula (3) and the compound represented by Formula (4), in the compound represented by Formula (3), the group represented by Formula (B-1-1) is the group represented by Formula (J-1), and $Rc_1$ represents an aryl group which may be substituted with a substituent other than a halogen atom, a heteroaryl group which may have a substituent, and in the compound represented by Formula (4), the group represented by Formula (B-1-1) is the group represented by Formula (J-1), $Rc_1$ represents an aryl group which may be substituted with a substituent other than a halogen atom, a heteroaryl group which may have a substituent, and the total number of carbon atoms contained in $R_2$ and $R_3$ is 4 or more.

From the viewpoint of obtaining a superior effect of the present invention, the compound represented by Formula (1) is preferably the compound represented by Formula (2b-1) or the compound represented by Formula (2b-2).

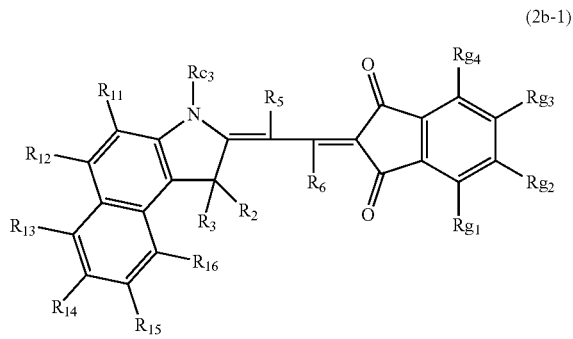

(2b-1)

In Formula (2b-1), the definitions of $R_2$, $R_3$, $R_5$, $R_6$, $R_{11}$ to $R_{16}$, and $Rg_1$ to $Rg_4$ are as described above.

Rc3 represents a group represented by Formula (4A) or a polycyclic aromatic ring which may have a substituent, and is preferably the group represented by Formula (5A), the group represented by Formula (5B), or a naphthyl group which may have a substituent. The total number of carbon atoms contained in $Rc_3$, $R_2$, $R_3$, and $R_{11}$ to $R_{16}$ is 5 or more. That is, the total number of carbon atoms contained in $Rc_3$, the carbon atoms contained in $R_2$, the carbon atoms contained in $R_3$, the carbon atoms contained in $R_{11}$, the carbon atoms contained in $R_{12}$, the carbon atoms contained in $R_{13}$, the carbon atoms contained in $R_{14}$, the carbon atoms contained in $R_{15}$, and the carbon atoms contained in $R_{16}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

However, the compound represented by Formula (2b-1) has none of a carboxy group, a salt of a carboxy group, a phosphoric acid group, a salt of a phosphoric acid group, a sulfonic acid group, or a salt of a sulfonic acid group.

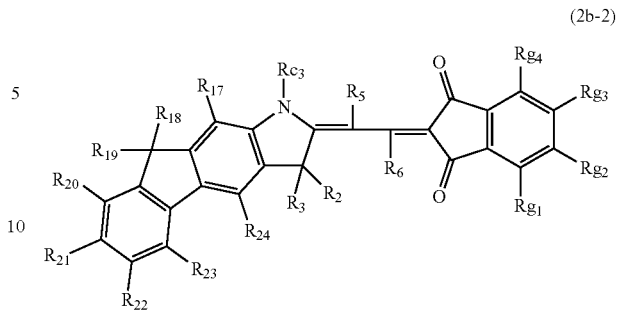

(2b-2)

In Formula (2b-2), the definitions of $Rc_3$, $R_2$, $R_3$, $R_5$, $R_6$, $R_{17}$ to $R_{24}$, and $Rg_1$ to $Rg_4$ are as described above.

The total number of carbon atoms contained in $Rc_3$, $R_2$, $R_3$, and $R_{17}$ to $R_{24}$ is 5 or more. That is, the total number of carbon atoms contained in $Rc_3$, the carbon atoms contained in $R_2$, the carbon atoms contained in $R_3$, the carbon atoms contained in $R_{17}$, the carbon atoms contained in $R_{18}$, the carbon atoms contained in $R_{19}$, the carbon atoms contained in $R_{20}$, the carbon atoms contained in $R_{21}$, the carbon atoms contained in $R_{22}$, the carbon atoms contained in $R_{23}$, and the carbon atoms contained in $R_{24}$ is 5 or more.

Among these, the total number of carbon atoms is preferably 11 or more, more preferably 15 or more, from the viewpoint of obtaining a superior effect of the present invention. The total number of carbon atoms is not particularly limited, but is preferably 30 or less.

Further, in Formula (2b-2), the total number of carbon atoms contained in $R_2$ and $R_3$ is 4 or more. That is, the total number of carbon atoms contained in $R_2$ and the number of carbon atoms contained in $R_3$ is 4 or more.

However, the compound represented by Formula (2b-2) has none of a carboxy group, a salt of a carboxy group, a phosphoric acid group, a salt of a phosphoric acid group, a sulfonic acid group, or a salt of a sulfonic acid group.

(Substituent W)

The substituent W in the present specification will be described below.

Examples of the substituent W include a halogen atom (such as a fluorine atom, a chlorine atom, a bromine atom, and an iodine atom), an alkyl group (including a cycloalkyl group, a bicycloalkyl group, and a tricycloalkyl group), an alkenyl group (including a cycloalkenyl group and a bicycloalkenyl group), an alkynyl group, an aryl group, a heteroaryl group (may be referred to as a heterocyclic group), a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonium group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, and a boronic acid group ($-B(OH)_2$).

Also, the substituent W may be further substituted with the substituent W. For example, an alkyl group may be substituted with a halogen atom.
The specific compounds are exemplified below, but the specific compounds according to the embodiment of the present invention are not limited thereto.
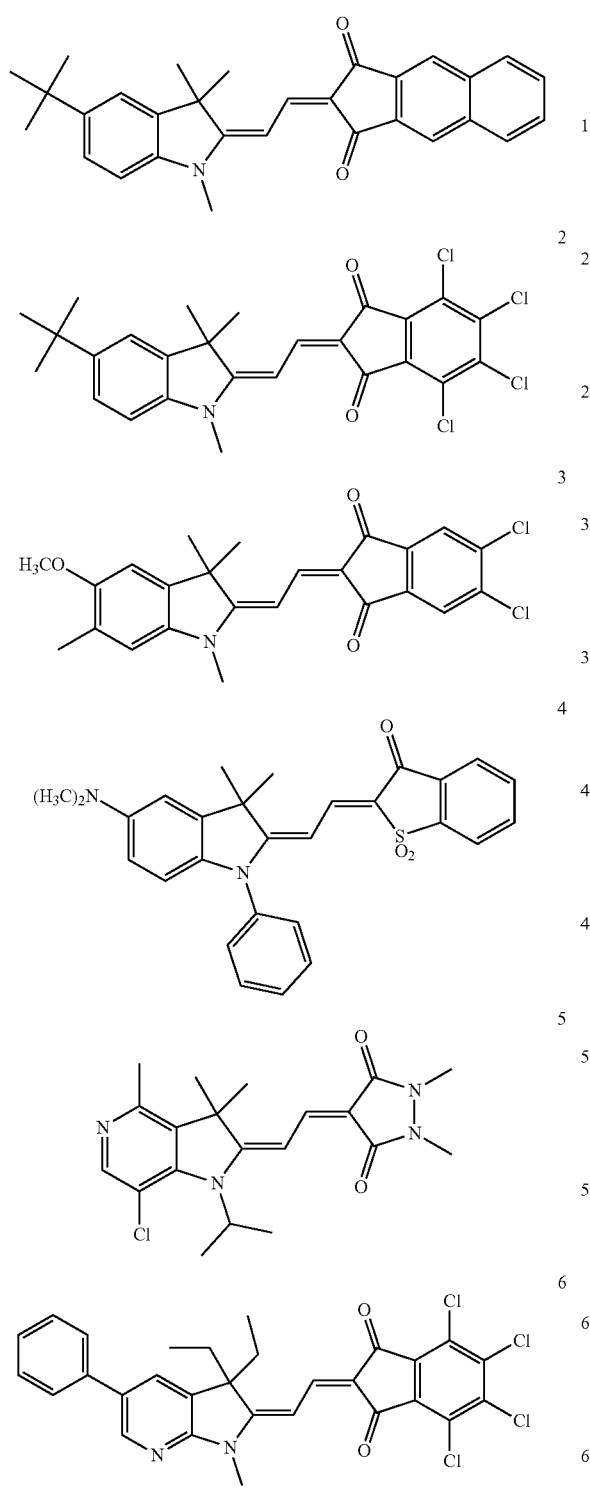
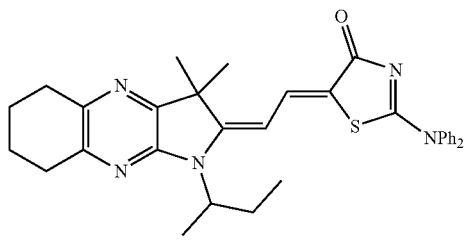
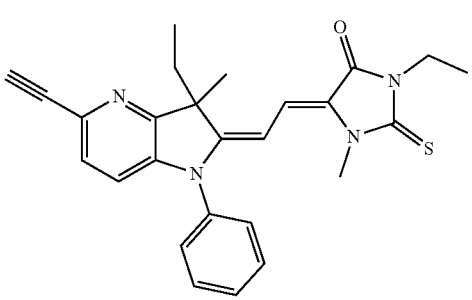
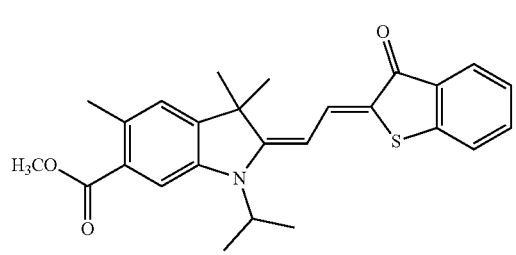
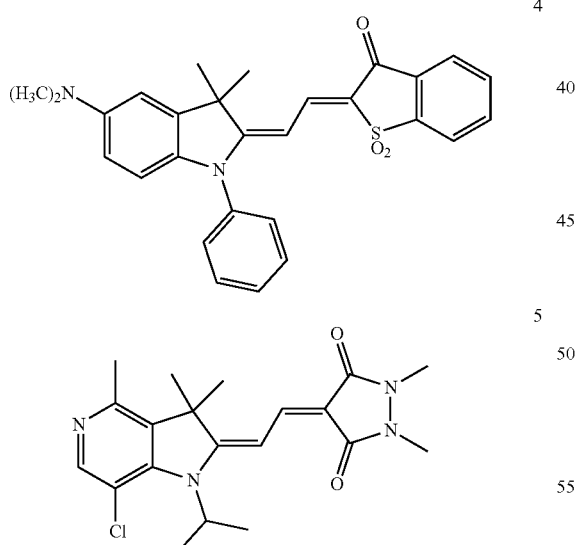
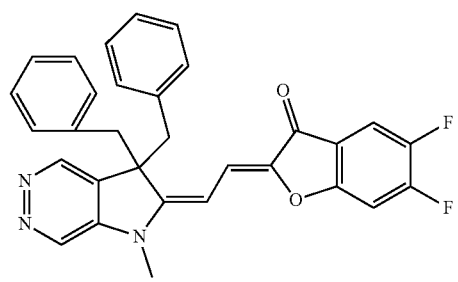
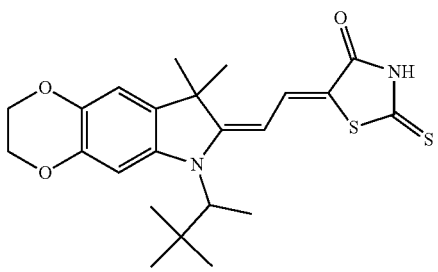

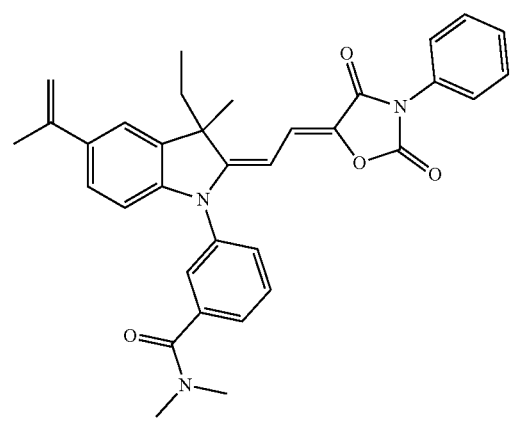
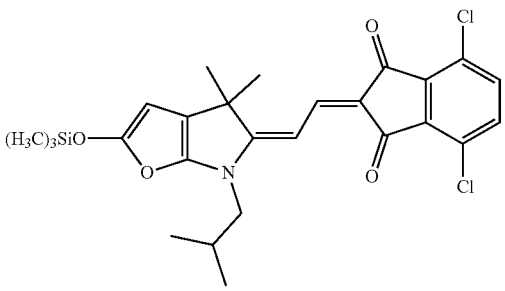
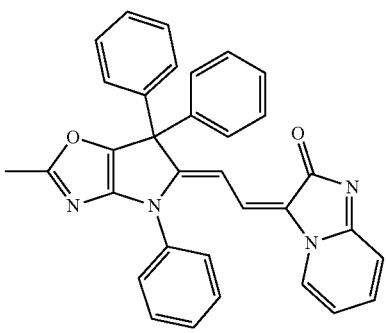
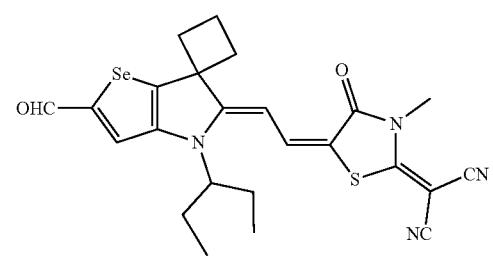
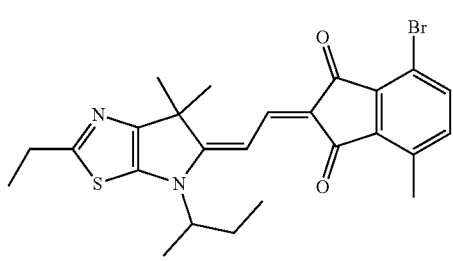
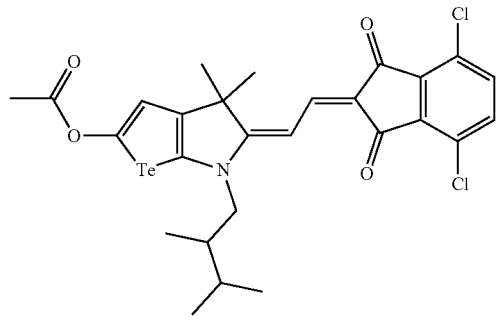

22
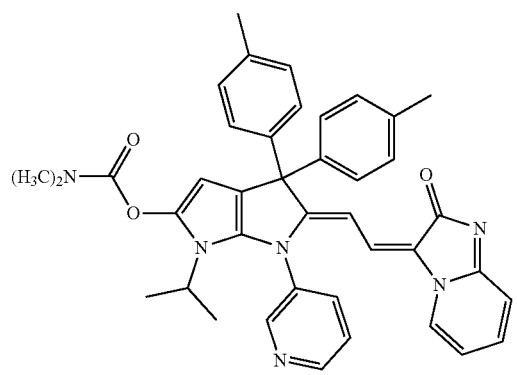
23
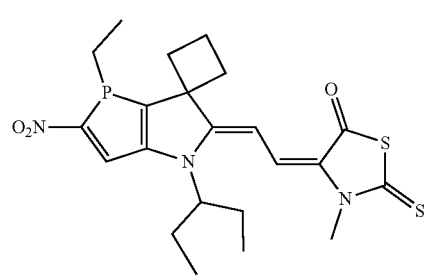
24
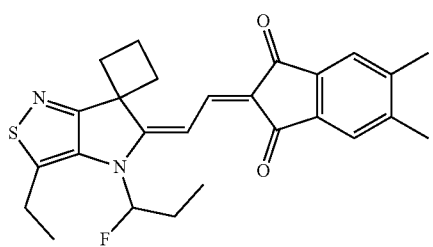
25
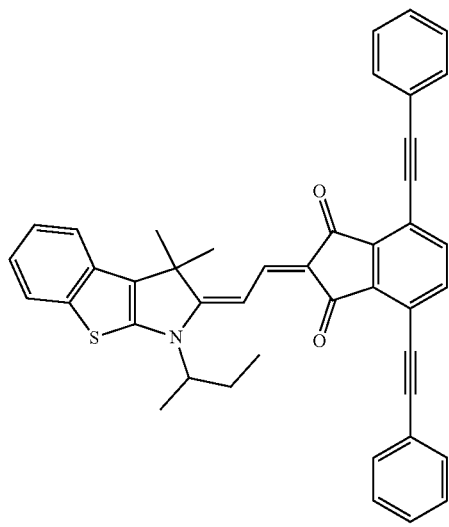
26
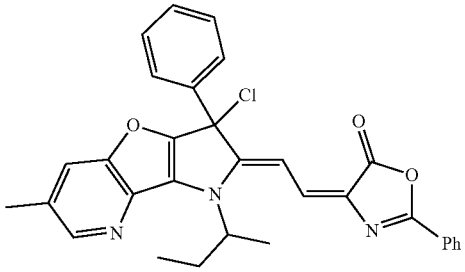
27
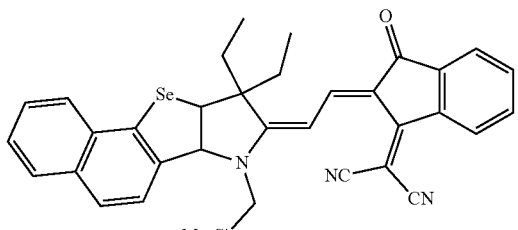
28
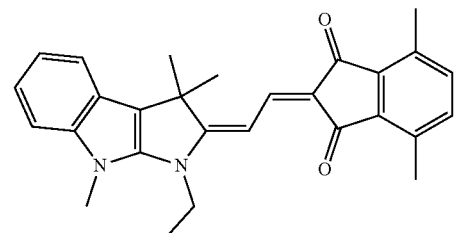
29
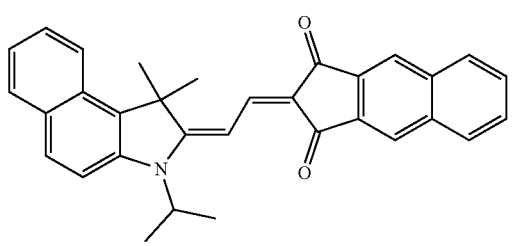
30
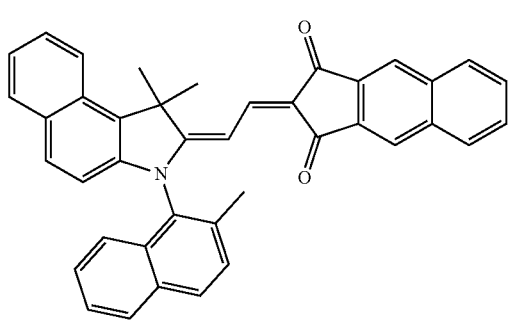

29
-continued
31
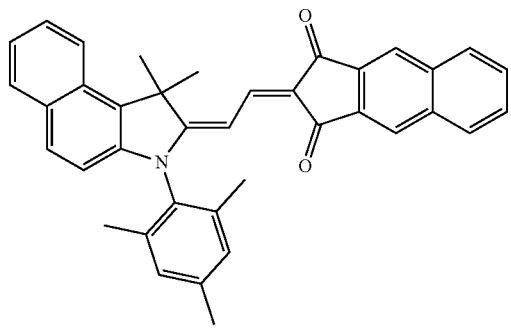
32
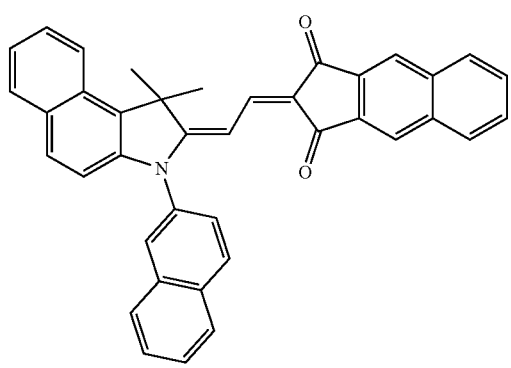
33
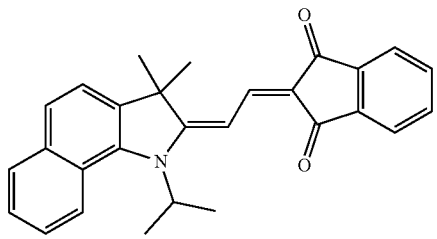
34
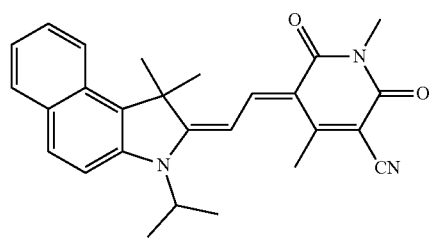
35
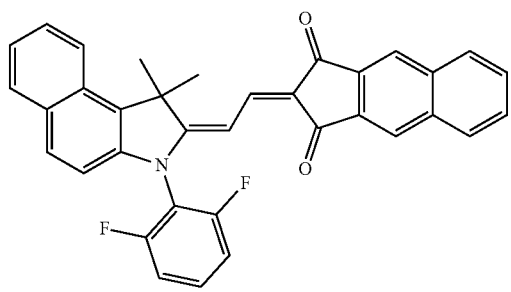
30
-continued
36
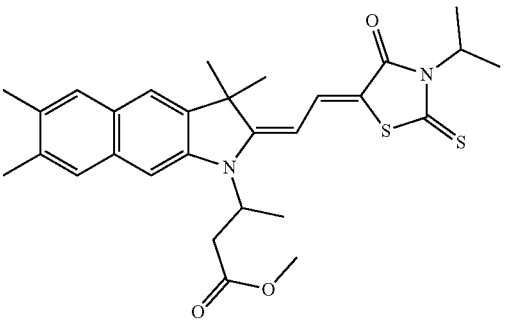
37
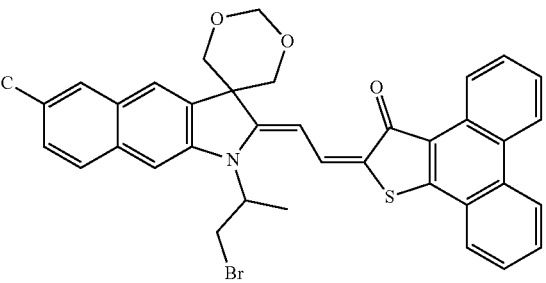
38
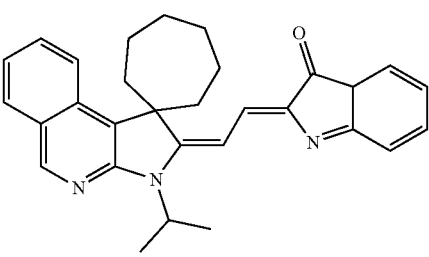
39
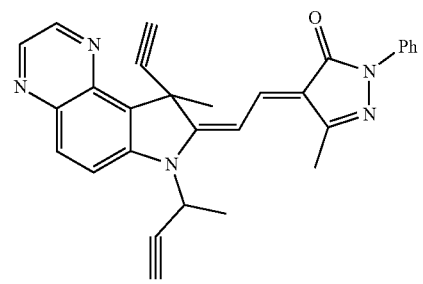
40
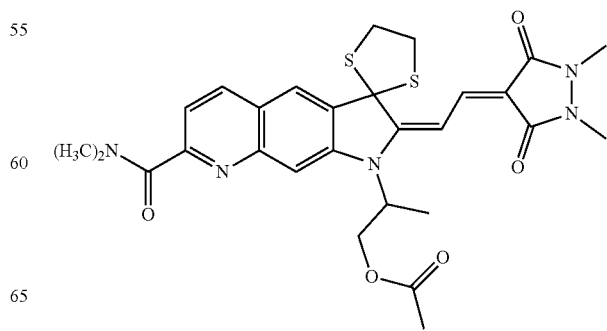

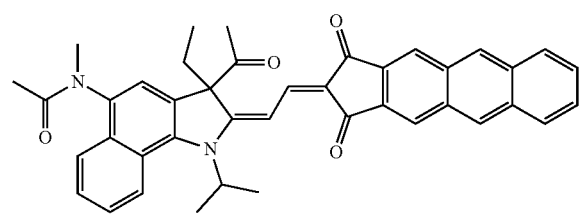
41
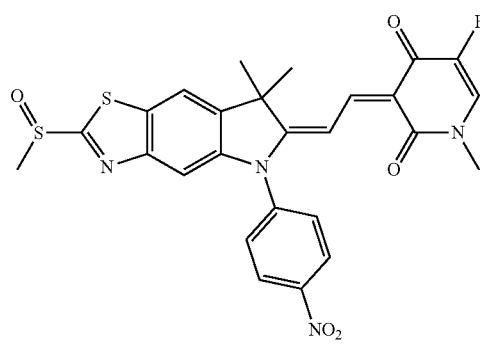
46
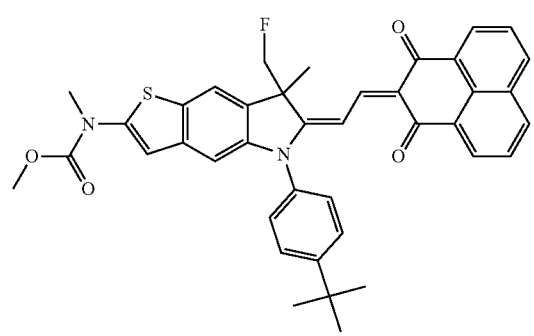
42
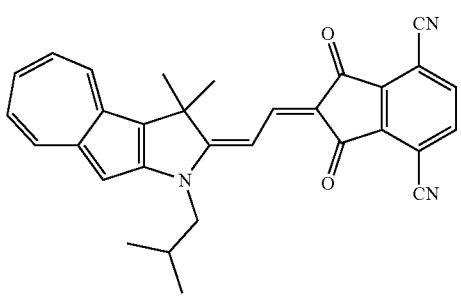
47
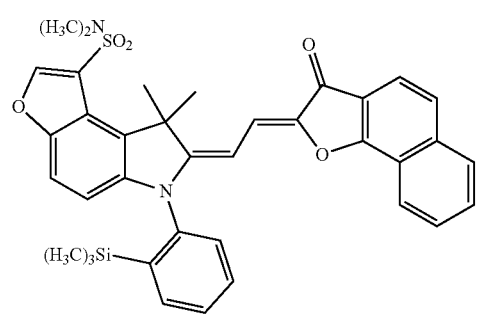
43
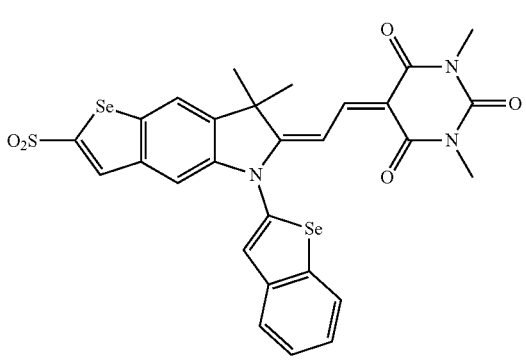
48
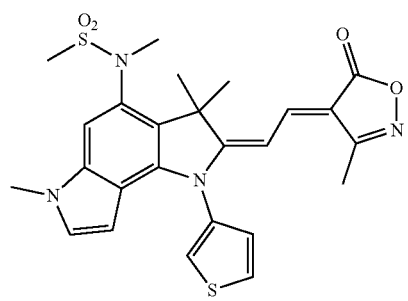
44
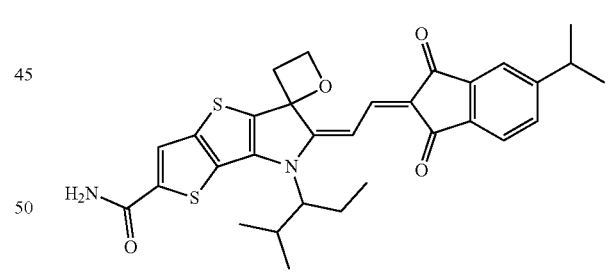
49
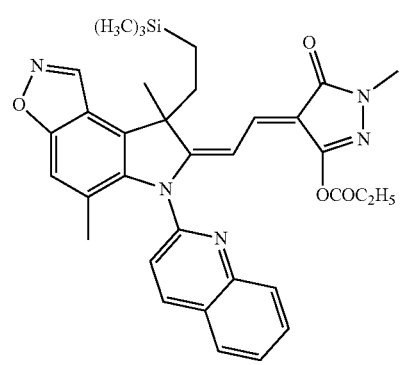
45
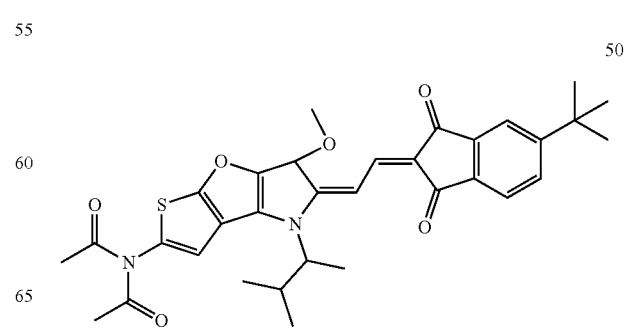
50

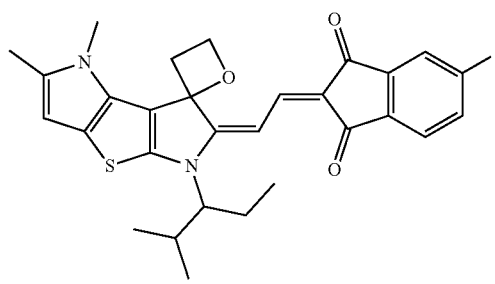
51
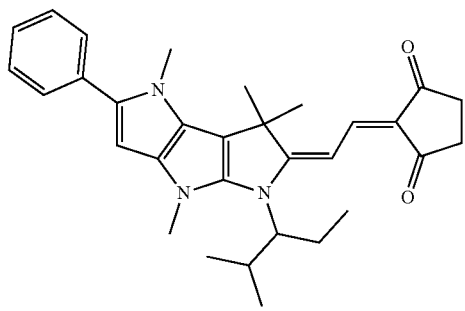
52
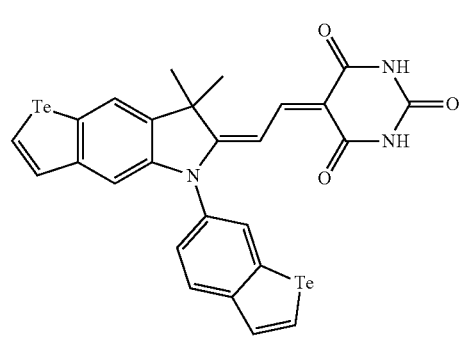
53
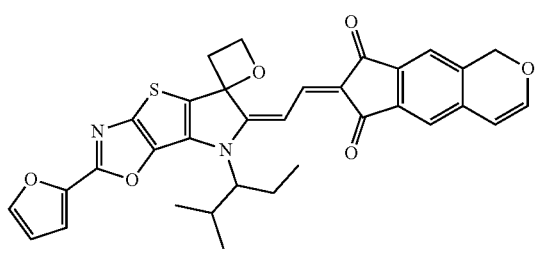
54
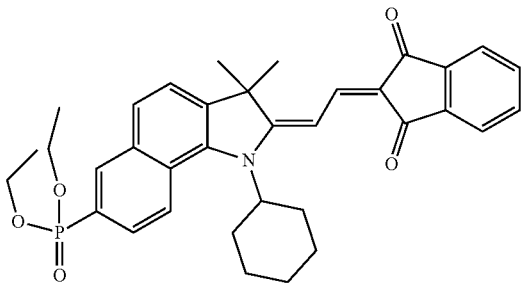
55
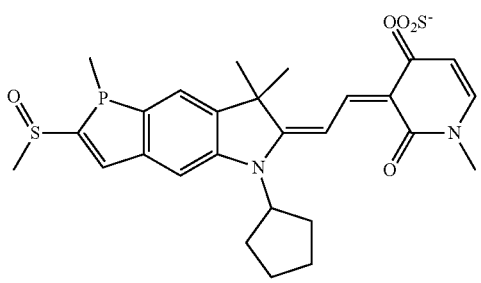
56
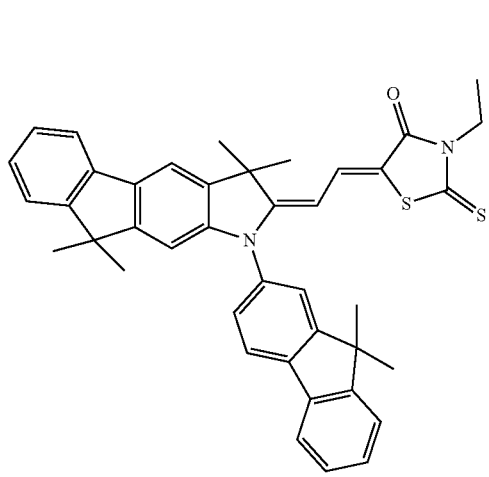
57
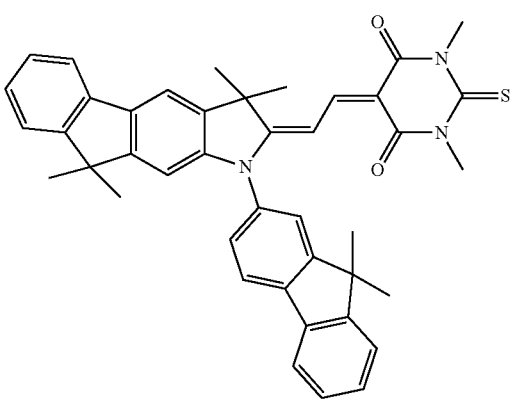
58
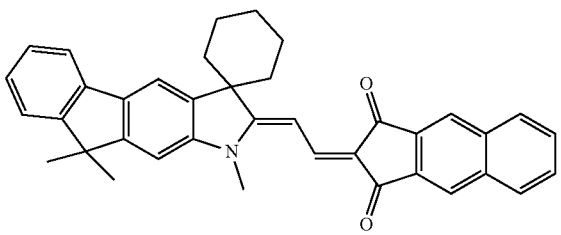
59

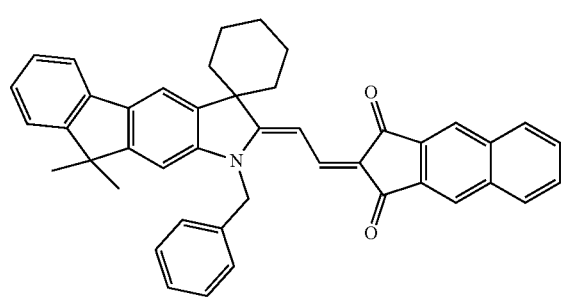
60
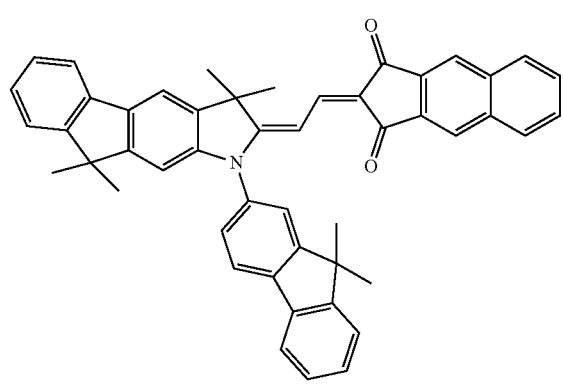
61
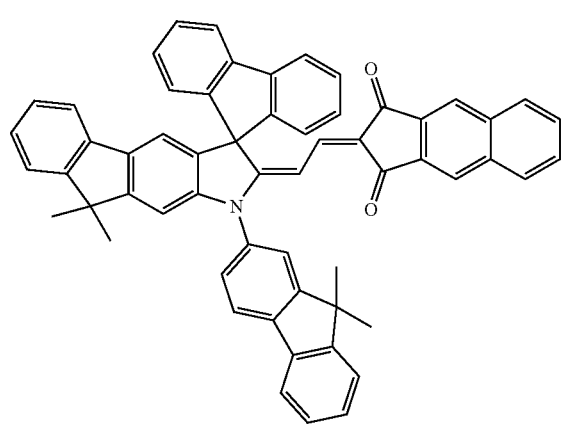
62
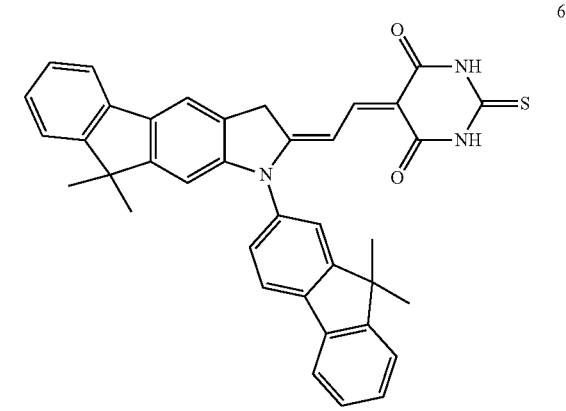
63
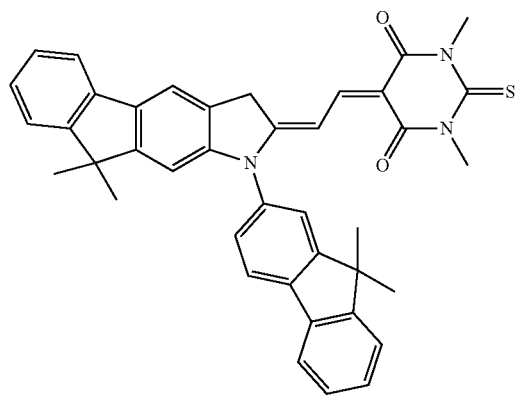
64
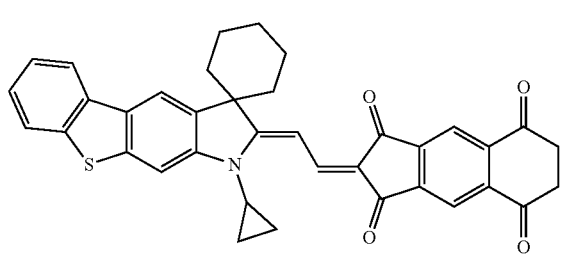
65
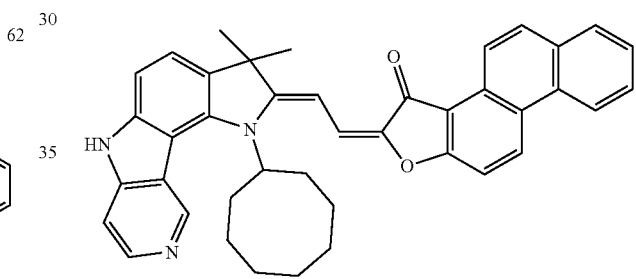
66
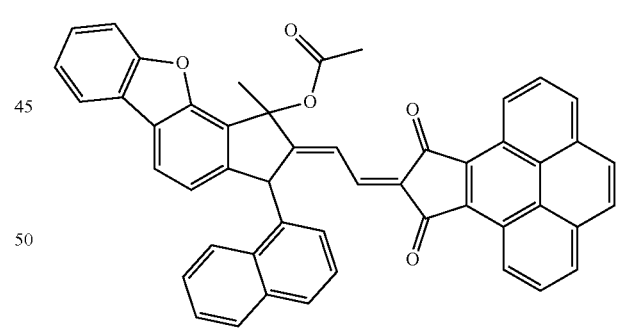
67
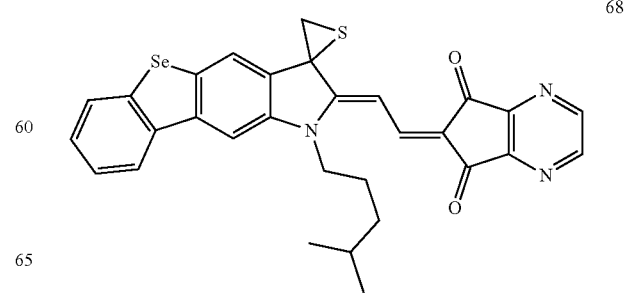
68

69
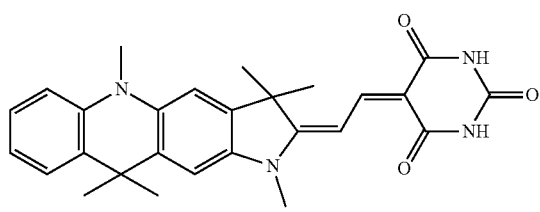
70
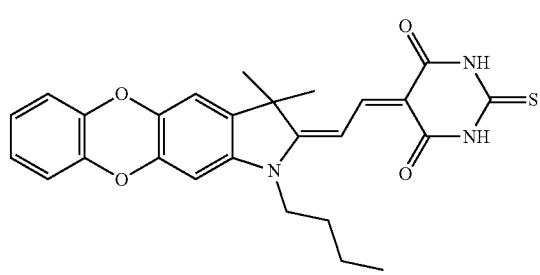
71
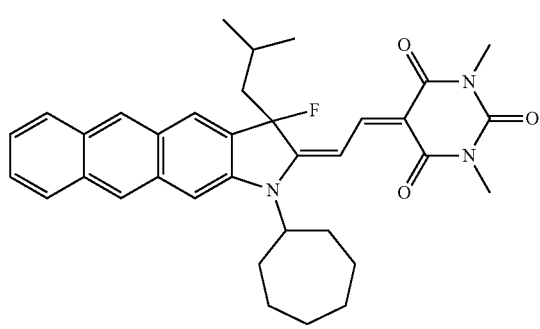
72
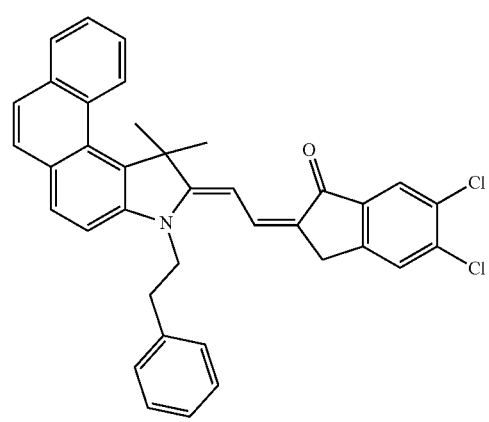
73
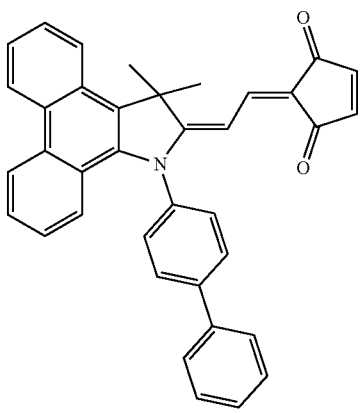
74
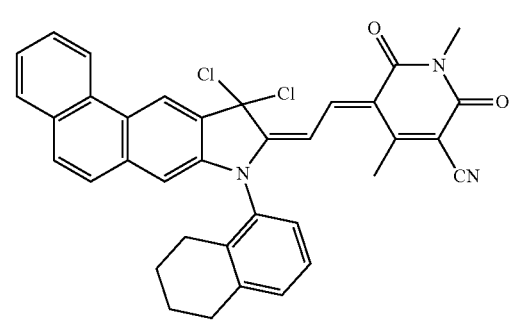
75
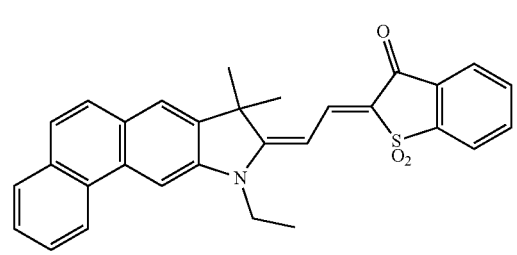
76
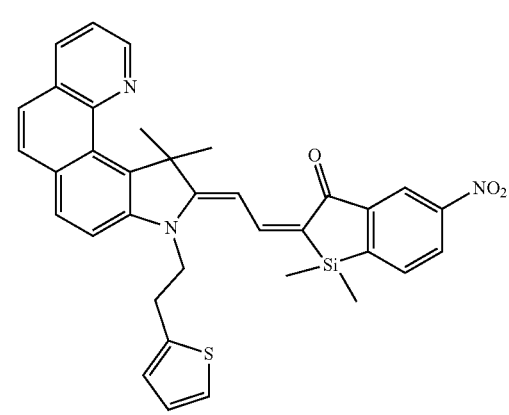

77
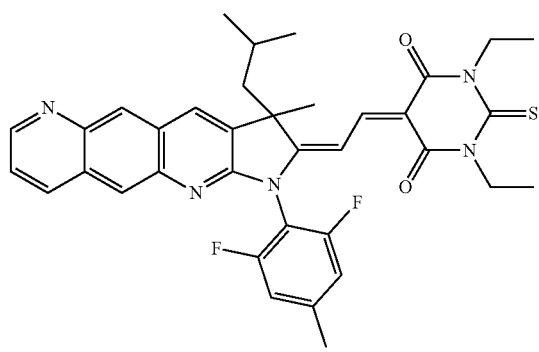
78
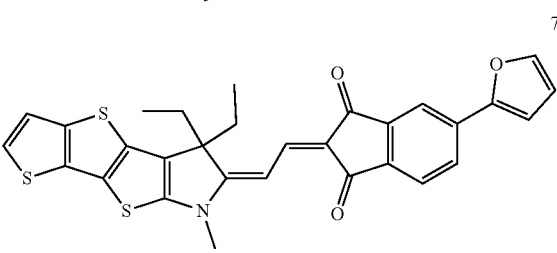
79
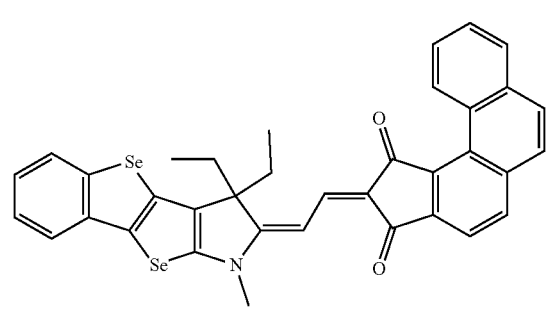
80
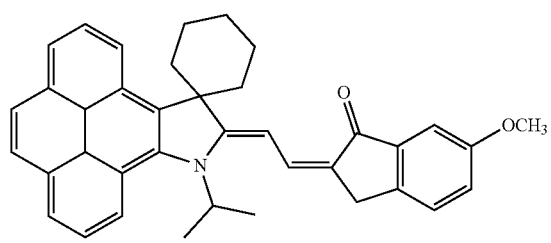
81
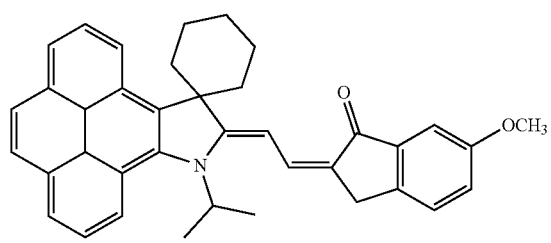
82
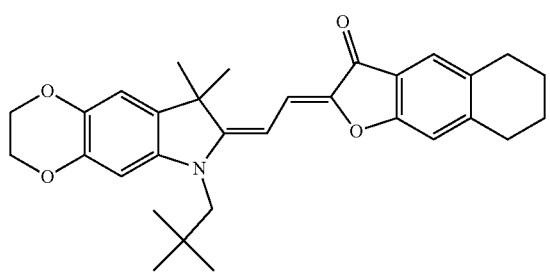
83
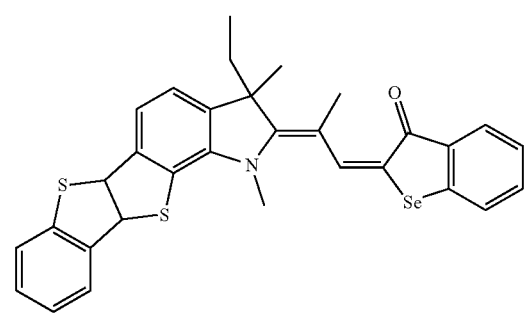
84
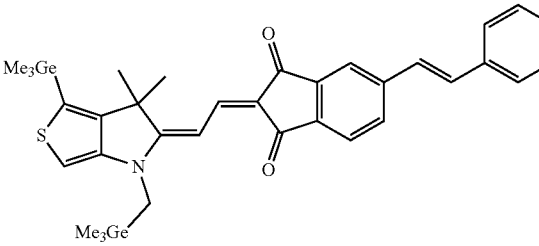
85
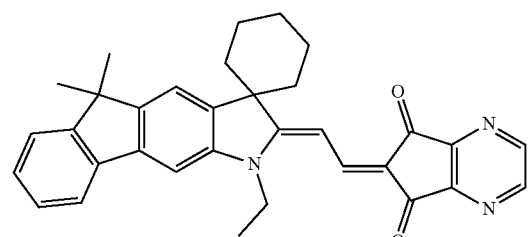
86
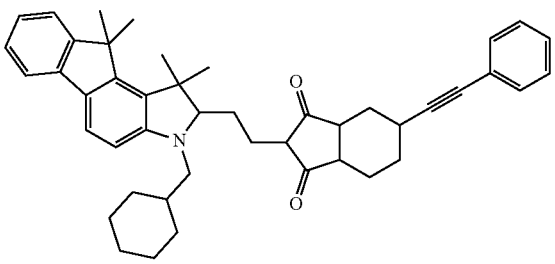

87
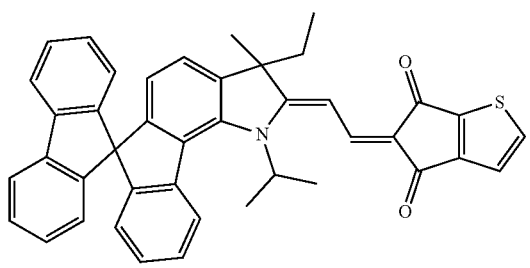
86
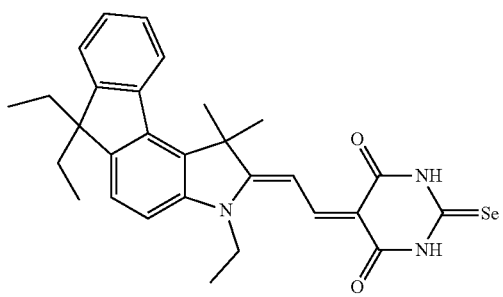
87
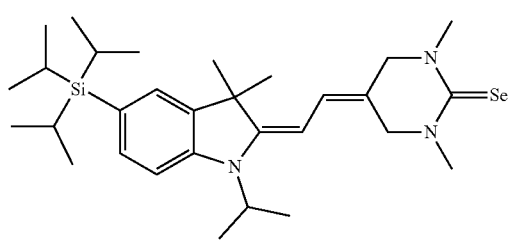
88
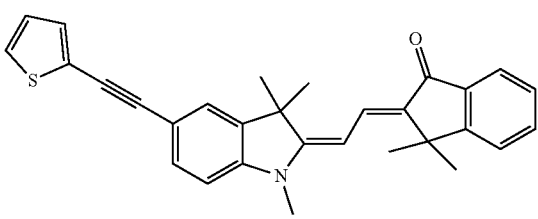
89
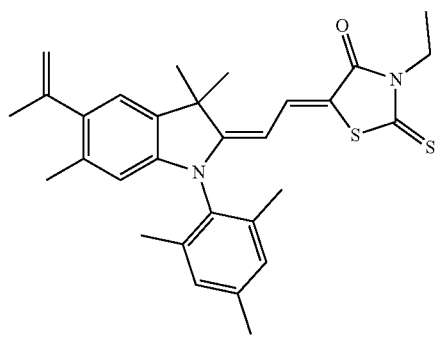
90
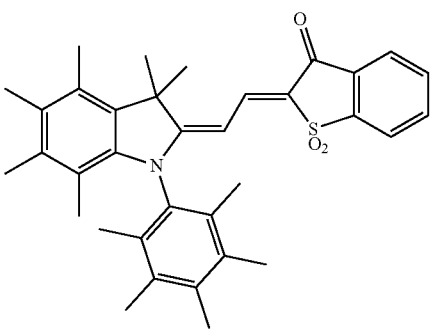
91
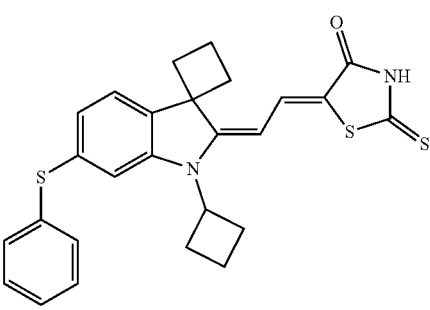
92
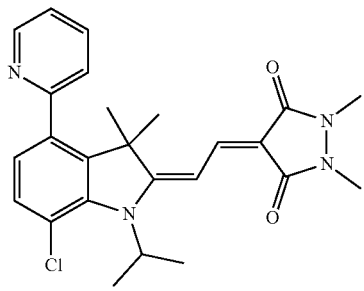
93
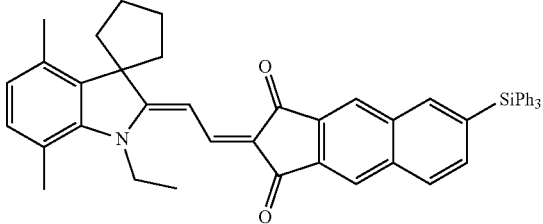
94
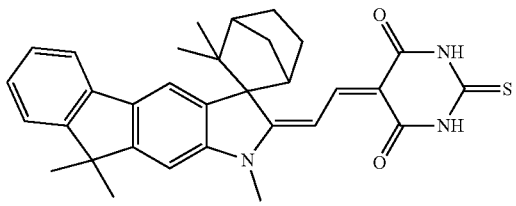

-continued
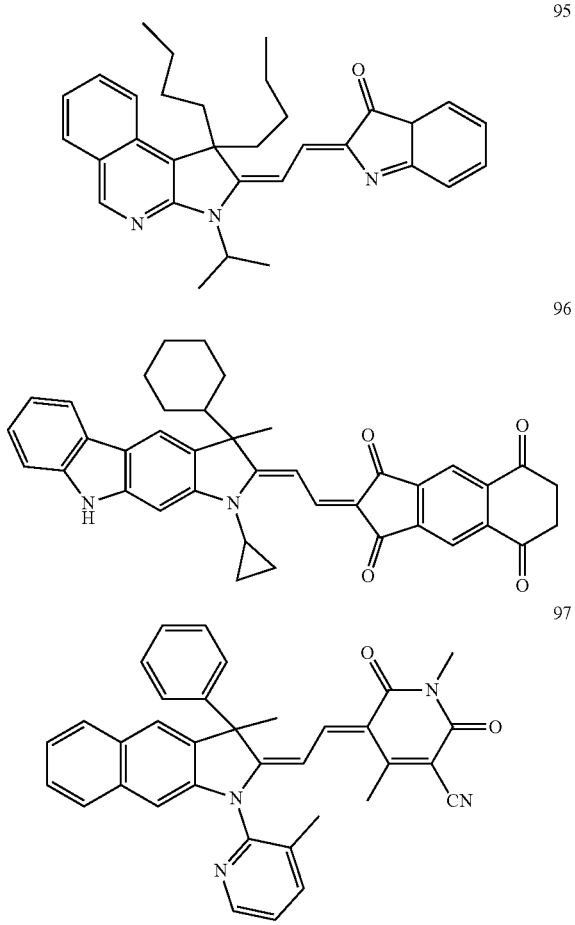
95
96
97
98
-continued
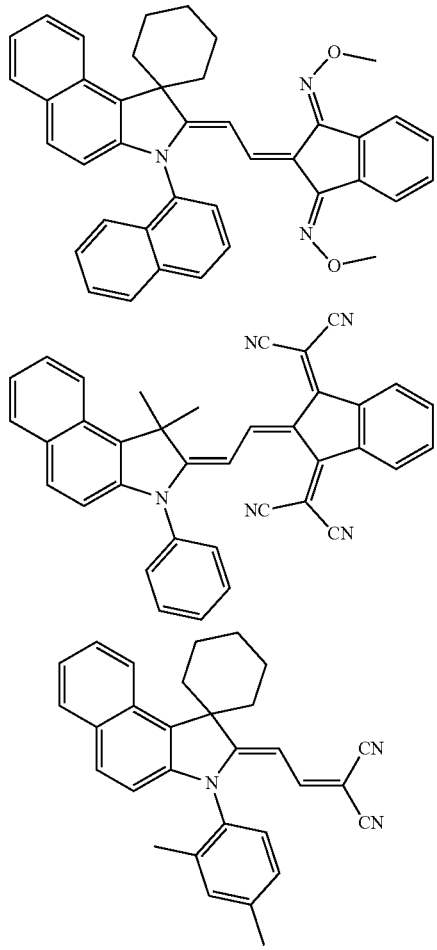
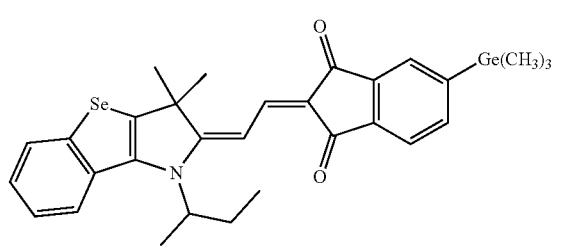
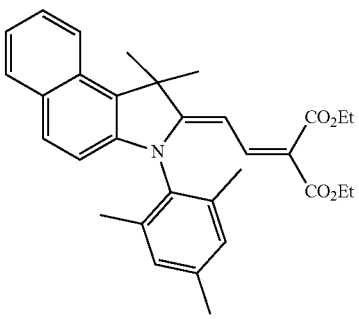
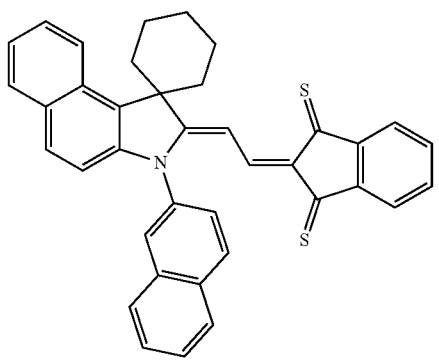
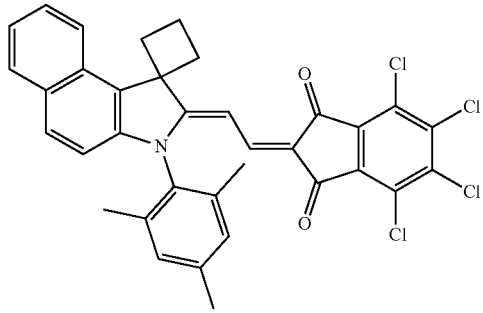

45
-continued
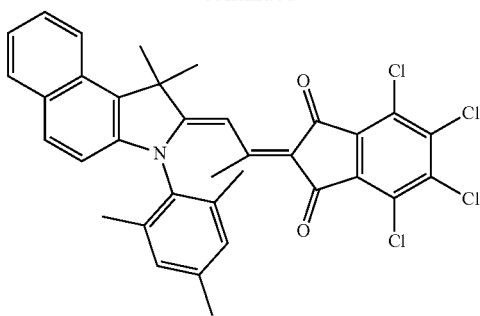
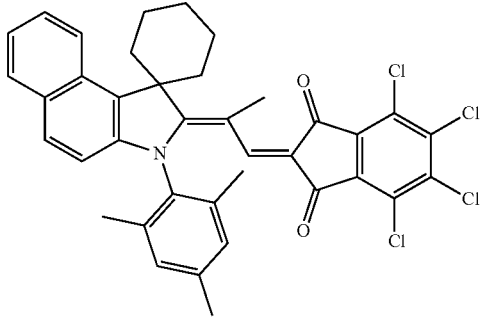
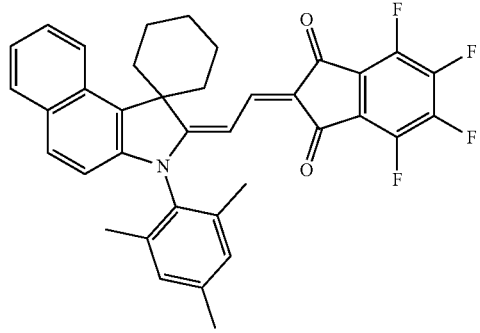
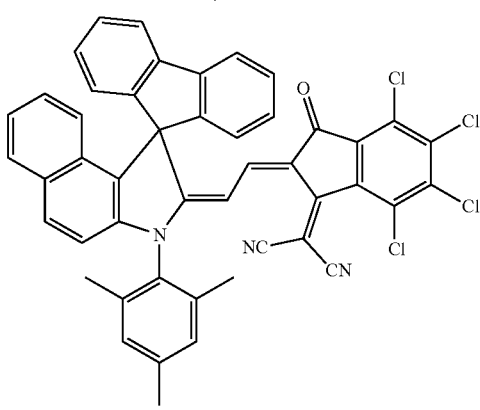
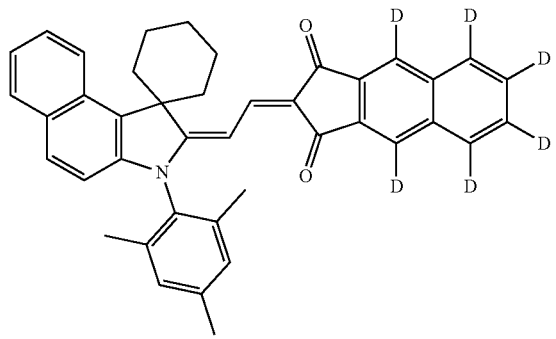
46
-continued
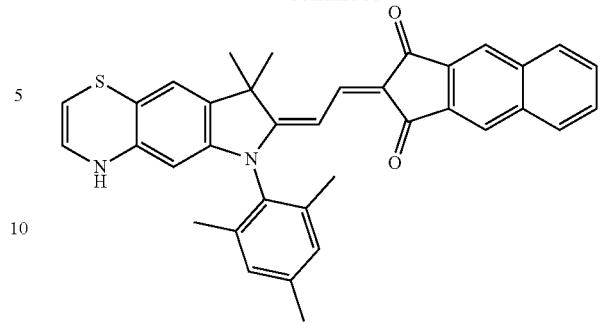
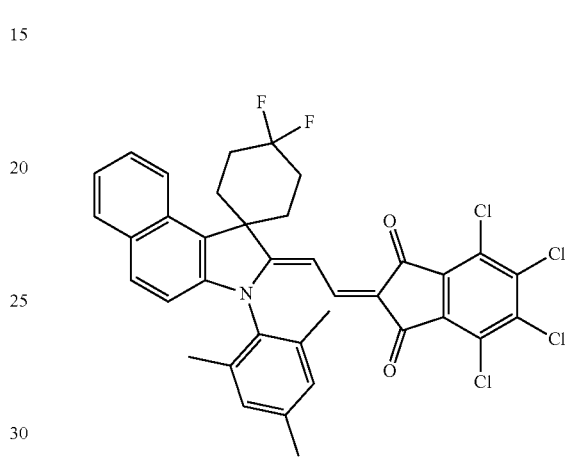
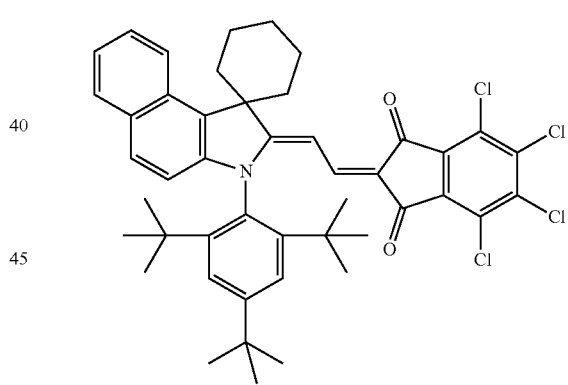
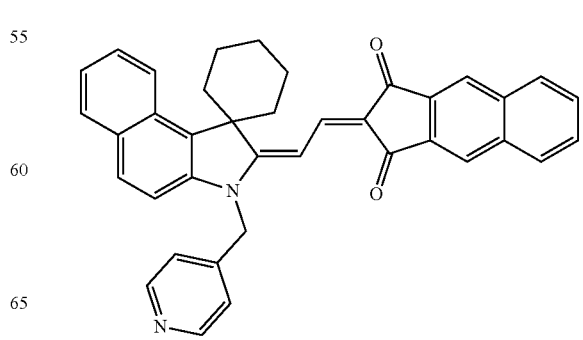

47
-continued
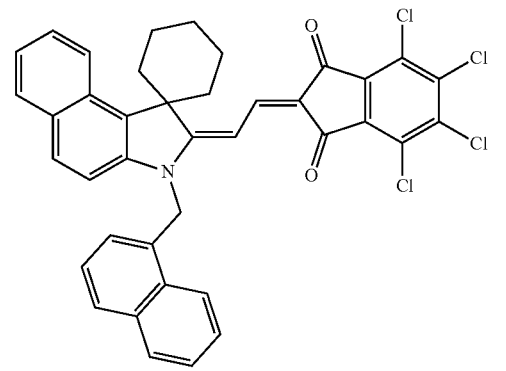
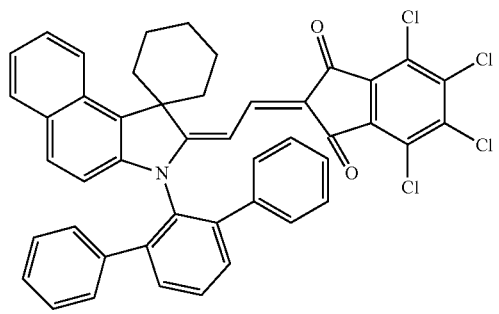
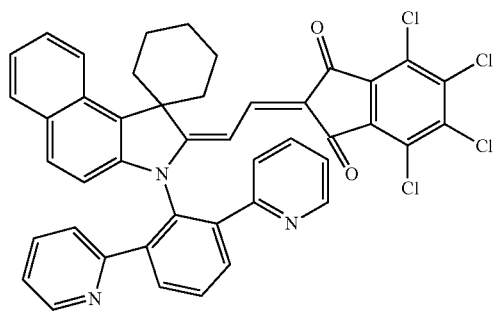
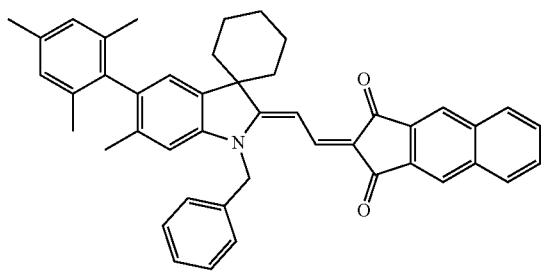
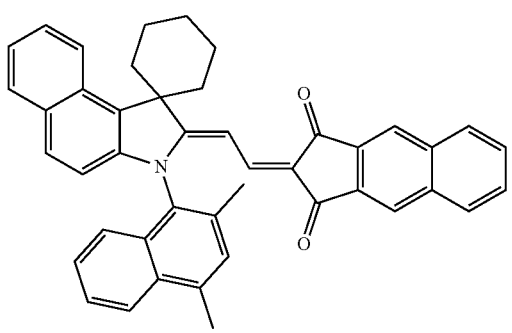
48
-continued
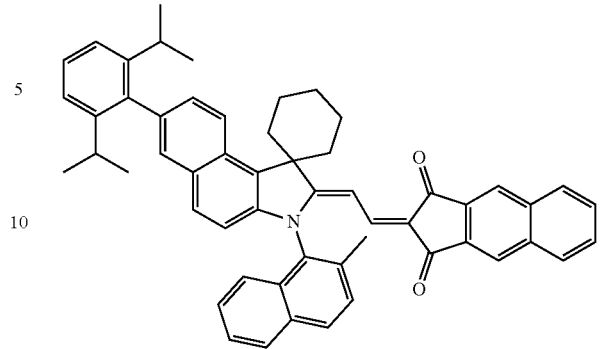
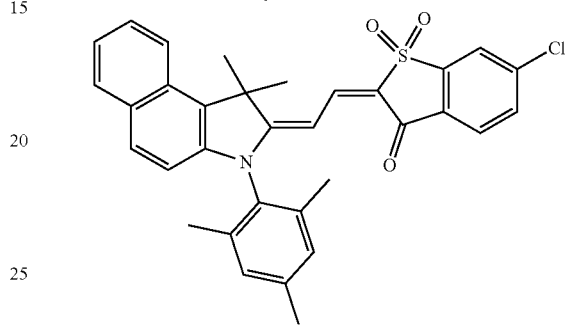
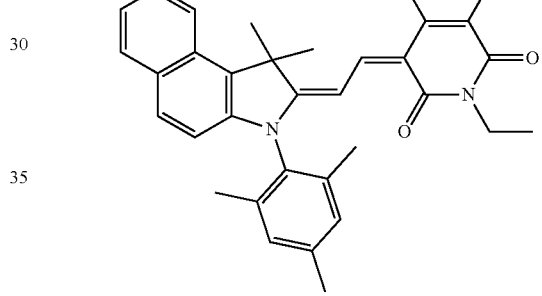
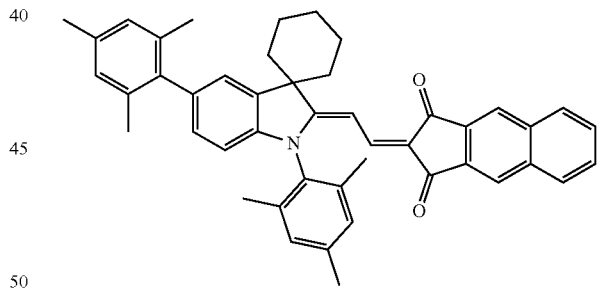
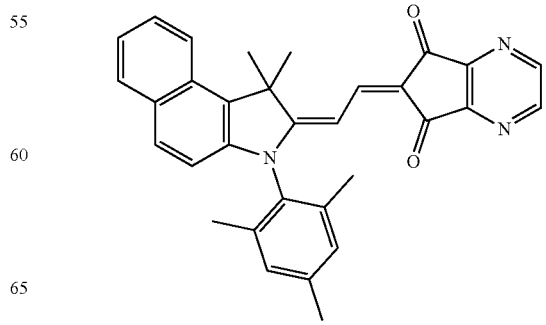

49
-continued
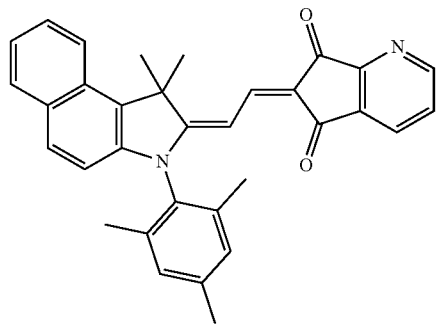
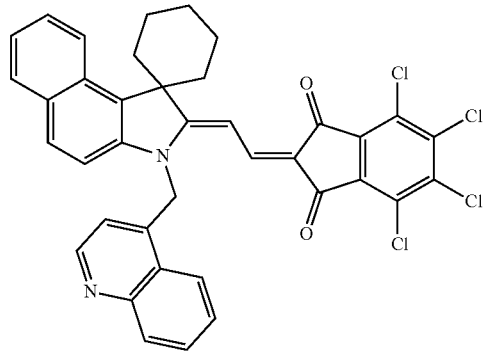
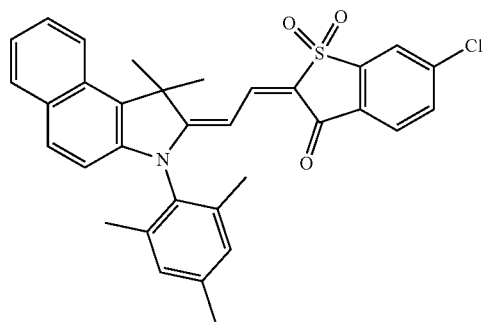
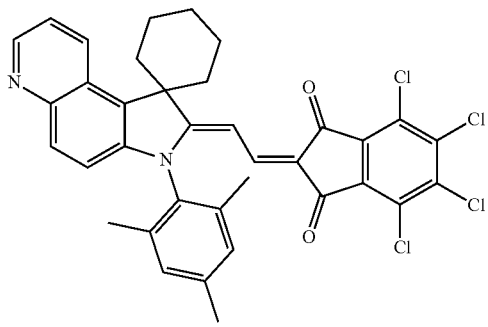
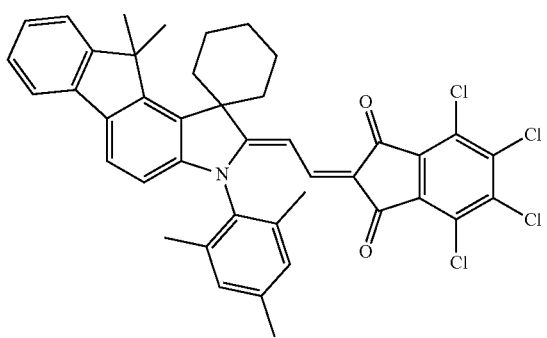
50
-continued
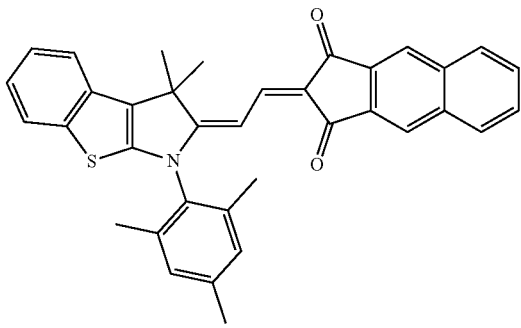
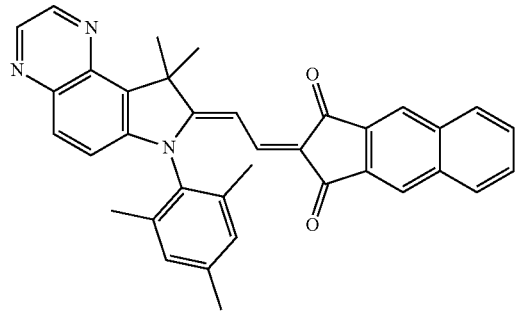
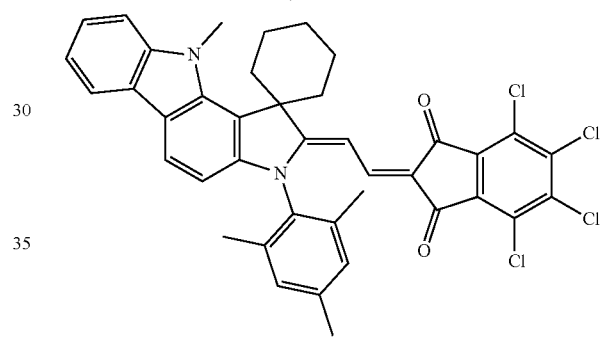
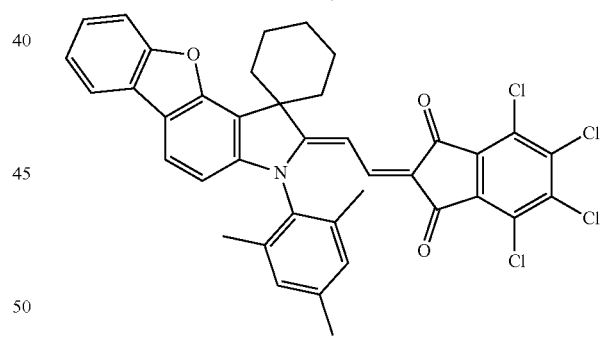
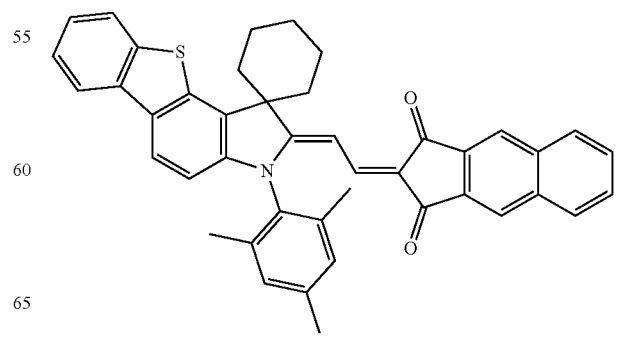

51
-continued
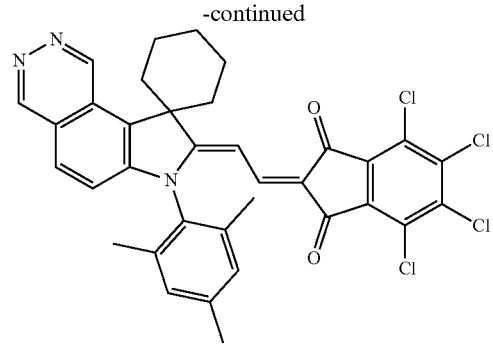
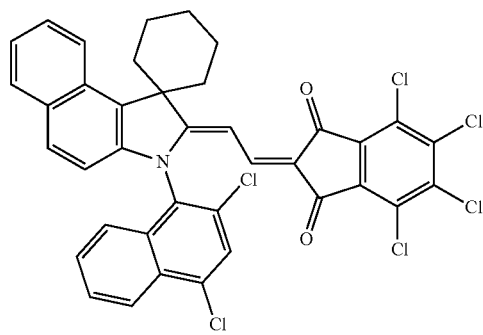
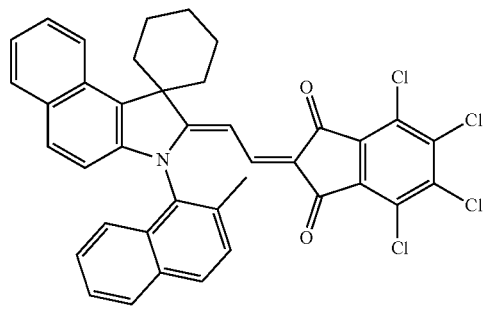
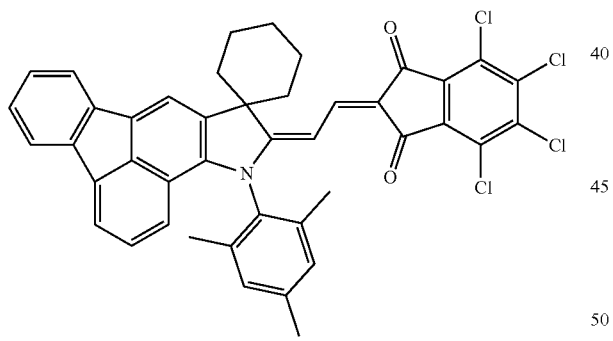
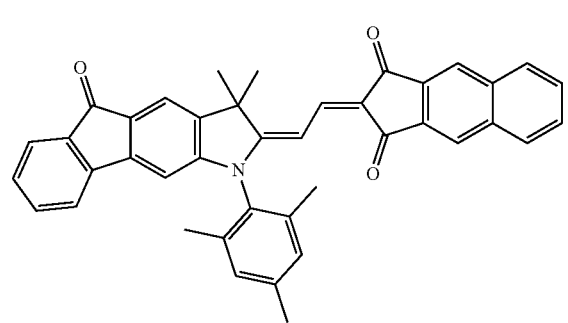
52
-continued
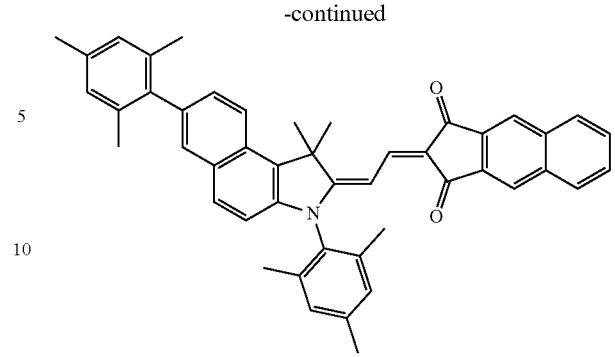
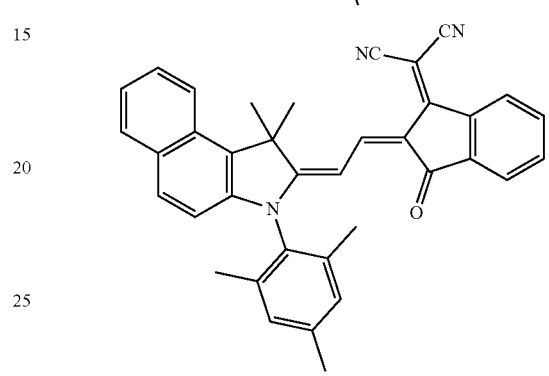
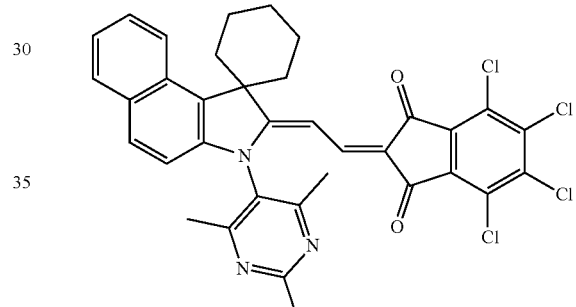
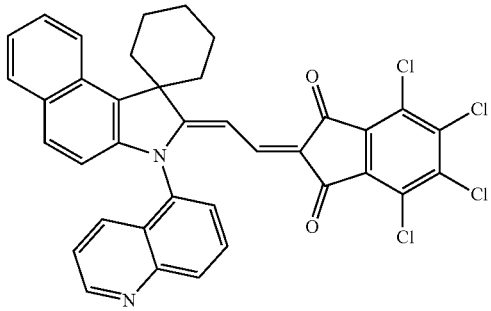
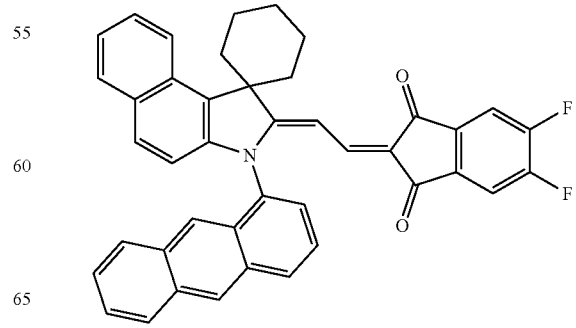

53
-continued
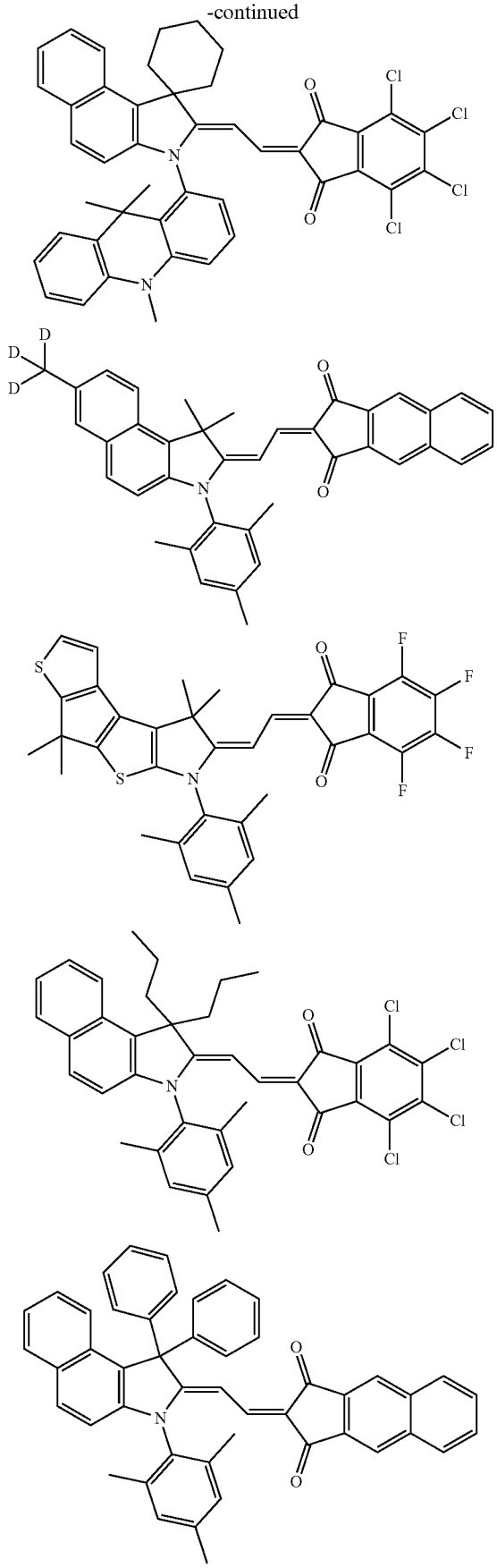
54
-continued
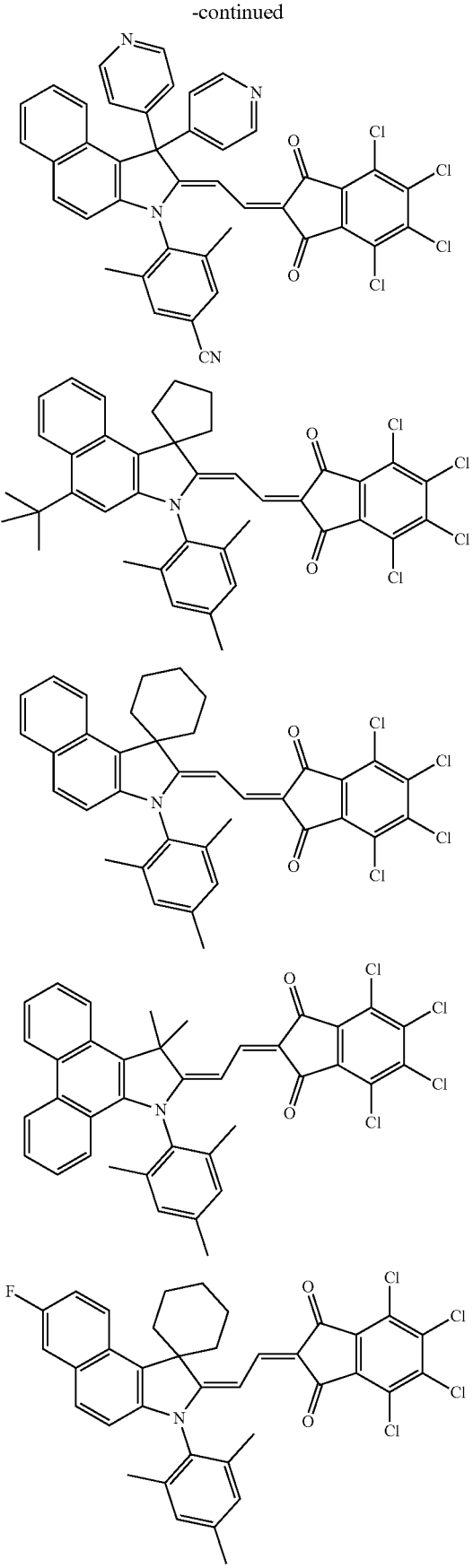

55
-continued
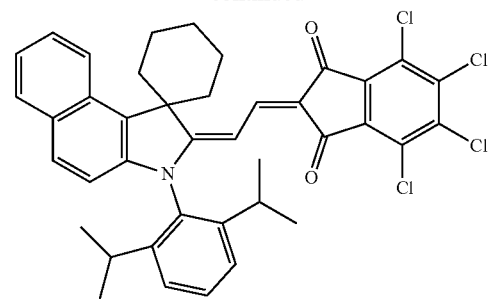
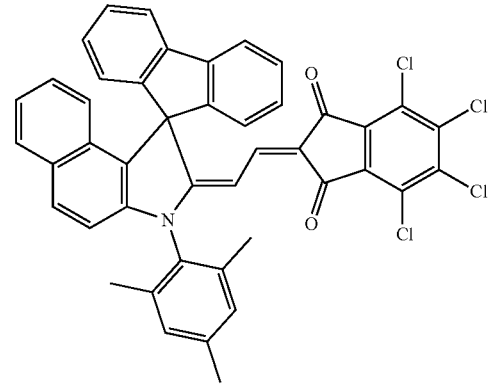
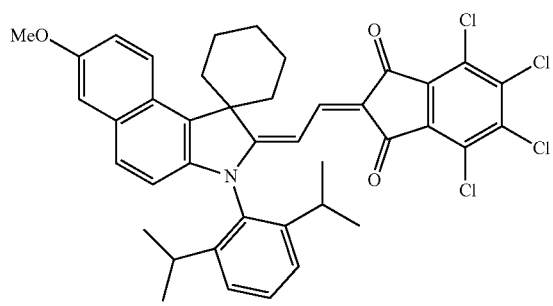
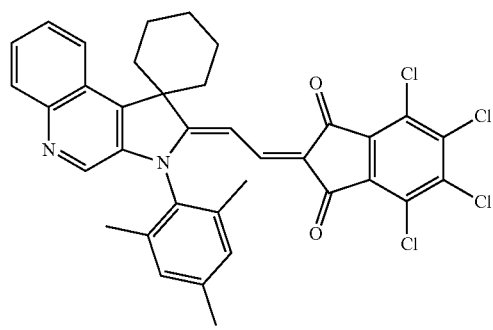
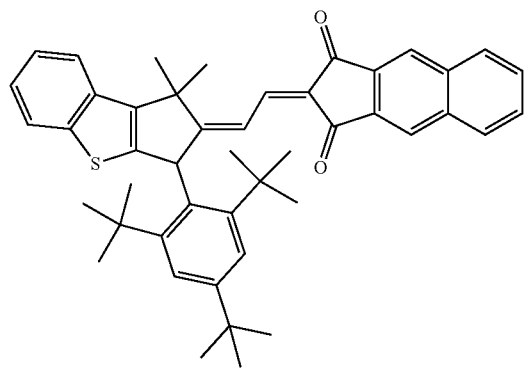
56
-continued
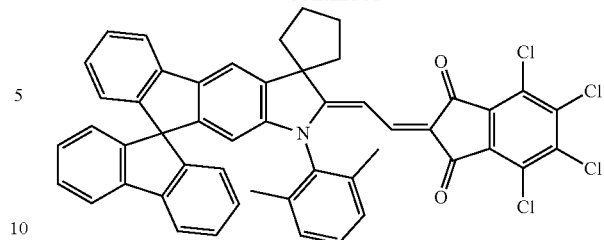
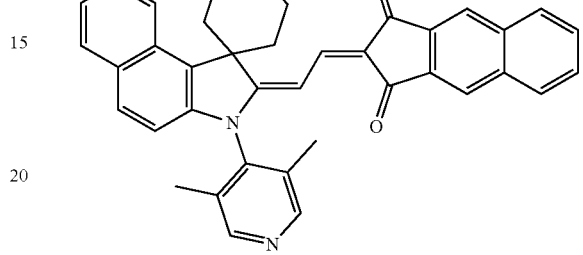
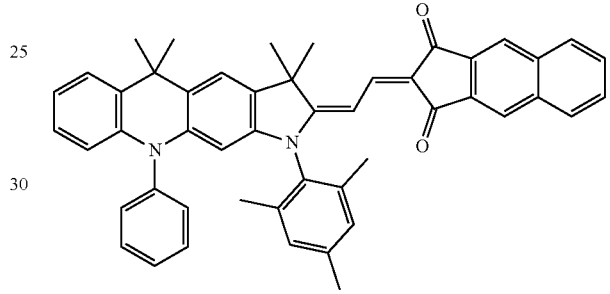
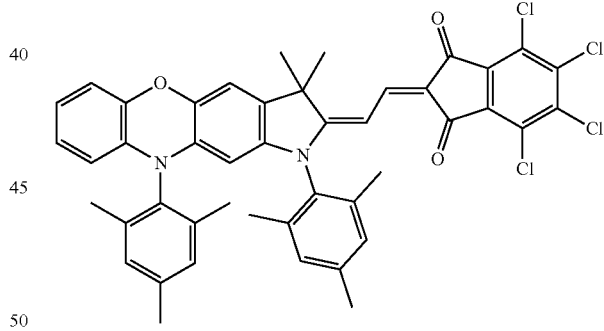
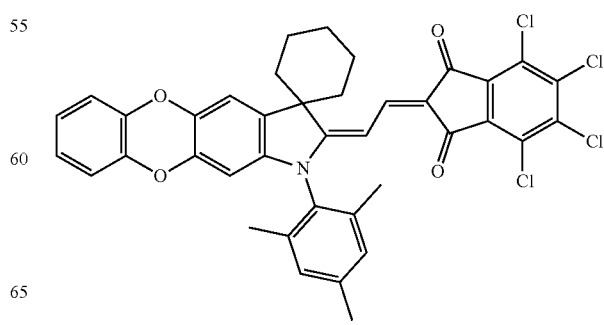

-continued

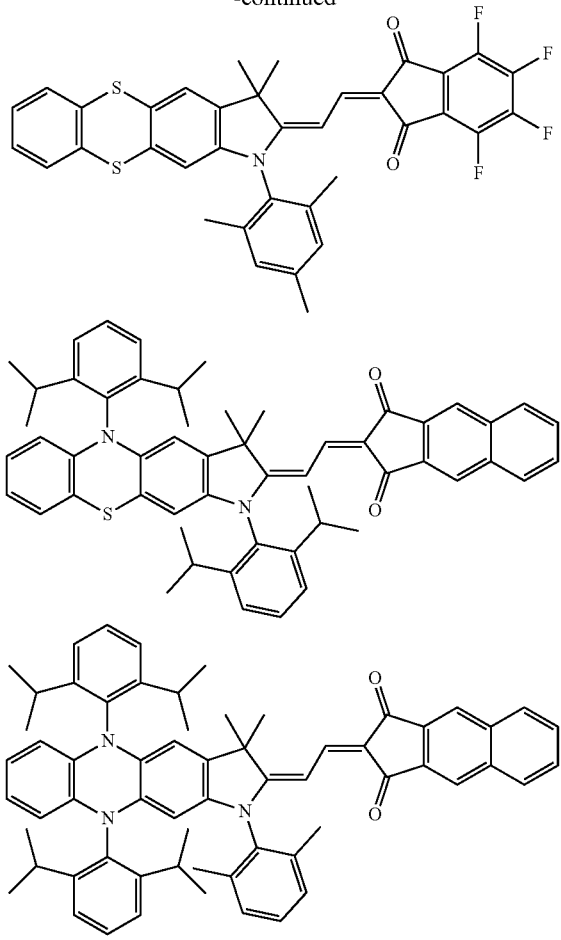

The specific compound is particularly useful as a material of the photoelectric conversion film used for the imaging element, the optical sensor, or a photoelectric cell. In addition, the specific compound usually functions as the p-type organic semiconductor in the photoelectric conversion film in many cases. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of stability in a case of using the compound as the p-type organic semiconductor and matching of energy levels between the compound and the n-type organic semiconductor.

The maximum absorption wavelength of the specific compound is not particularly limited, but is preferably in the range of 500 nm or more and less than 590 nm, more preferably in the range of 520 nm or more and less than 580 nm, and still more preferably in the range of 540 nm or more and less than 570 nm from the point that the photoelectric conversion film in the photoelectric conversion element according to the embodiment of the present invention is suitably used as an organic photoelectric conversion film that receives (absorbs) green light and performs photoelectrically conversion.

The maximum absorption wavelength is a value obtained by adjusting the absorption spectrum of the specific compound to a concentration at which the light absorbance becomes 0.5 to 1, and measuring the solution in a solution state (solvent:chloroform).

The maximum absorption wavelength of the photoelectric conversion film is not particularly limited, but is preferably in the range of 500 nm or more and less than 590 nm, more preferably in the range of 520 nm or more and less than 580 nm, and still more preferably in the range of 540 nm or more and less than 570 nm from the point that the photoelectric conversion film in the photoelectric conversion element according to the embodiment of the present invention is suitably used as an organic photoelectric conversion film that receives (absorbs) green light and performs photoelectrically conversion.

<n-Type Organic Semiconductor>

It is preferable that the photoelectric conversion film contains the n-type organic semiconductor as a component other than the specific compound.

The n-type organic semiconductor is an acceptor-property organic semiconductor material (a compound), and refers to an organic compound having a property of easily accepting an electron. More specifically, the n-type organic semiconductor refers to an organic compound having a large electron affinity of two organic compounds used in contact with each other. Therefore, any organic compound having an electron accepting property can be used as the acceptor type organic semiconductor.

Examples of the n-type organic semiconductor include fullerenes selected from the group consisting of a fullerene and derivatives thereof, fused aromatic carbocyclic compounds (for example, a naphthalene derivative, an anthracene derivative, a phenanthrene derivative, a tetracene derivative, a pyrene derivative, a perylene derivative, and a fluoranthene derivative); a heterocyclic compound having a 5- to 7-membered ring having at least one of a nitrogen atom, an oxygen atom, and a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); polyarylene compounds; fluorene compounds; cyclopentadiene compounds; silyl compounds; 1,4,5,8-naphthalenetetracarboxylic acid anhydride; 1,4,5,8-naphthalenetetracarboxylic acid anhydride imide derivative, oxadiazole derivative; anthraquinodimethane derivatives; diphenylquinone derivatives; bathocuproine, bathophenanthroline, and derivatives thereof; triazole compounds; a distyrylarylene derivative; a metal complex having a nitrogen-containing heterocyclic compound as a ligand; a silole compound; and compounds disclosed in paragraphs [0056] to [0057] of JP2006-100767A.

Among these, it is preferable that examples of the n-type organic semiconductor (compound) include fullerenes selected from the group consisting of a fullerene and derivatives thereof.

Examples of fullerene include fullerene C60, fullerene C70, fullerene C76, fullerene C78, fullerene C80, fullerene C82, fullerene C84, fullerene C90, fullerene C96, fullerene C240, fullerene C540, and mixed fullerene.

Examples of fullerene derivatives include compounds in which a substituent is added to the above fullerenes. As the substituent, an alkyl group, an aryl group, or a heterocyclic group is preferable. As the fullerene derivative, the compounds described in JP2007-123707A are preferable.

An organic dye may be used as the n-type organic semiconductor. Examples of the organic dye include a cyanine dye, a styryl dye, a hemicyanine dye, a merocyanine dye (including zeromethine merocyanine (simple merocyanine)), a rhodacyanine dye, an allopolar dye, an oxonol dye, a hemioxonol dye, a squarylium dye, a croconium dye, an azamethine dye, a coumarin dye, an arylidene dye, an anthraquinone dye, a triphenylmethane dye, an azo dye, an azomethine dye, a metallocene dye, a fluorenone dye, a flugide dye, a perylene dye, a phenazine dye, a phenothiazine dye, a quinone dye, a diphenylmethane dye, a polyene dye, an acridine dye, an acridinone dye, a diphenylamine dye, a quinophthalone dye, a phenoxazine dye, a phthaloperylene dye, a dioxane dye, a porphyrin dye, a chlorophyll dye, a phthalocyanine dye, a subphthalocyanine dye, and a metal complex dye.

The molecular weight of the n-type organic semiconductor is preferably 200 to 1200, and more preferably 200 to 900.

From the point that the photoelectric conversion film in the photoelectric conversion element according to the embodiment of the present invention is suitably used as an organic photoelectric conversion film that receives (absorbs) green light and performs photoelectrically conversion, it is preferable that the n-type organic semiconductor is colorless or has a maximum absorption wavelength and/or an absorption waveform close to that of the specific compound, and as the specific value, the maximum absorption wavelength of the n-type organic semiconductor is preferably 400 nm or less or in the range of 500 to 600 nm.

It is preferable that the photoelectric conversion film has a bulk hetero structure formed in a state in which the specific compound and the n-type organic semiconductor are mixed. The bulk hetero structure refers to a layer in which the specific compound and the n-type organic semiconductor are mixed and dispersed in the photoelectric conversion film. The photoelectric conversion film having the bulk hetero structure can be formed by either a wet method or a dry method. The bulk hetero structure is described in detail in, for example, paragraphs [0013] to [0014] of JP2005-303266A.

From the viewpoint of responsiveness of the photoelectric conversion element, the content of the specific compound to the total content of the specific compound and the n-type organic semiconductor (=film thickness in terms of single layer of specific compound/(film thickness in terms of single layer of specific compound+film thickness in terms of single layer of n-type organic semiconductor)×100) is preferably 15 to 75 volume %, and more preferably 35 to 75 volume %.

Also, in a case where the photoelectric conversion film contains a p-type organic semiconductor described below, the content of the specific (=film thickness in terms of single layer of specific compound/(film thickness in terms of single layer of specific compound+film thickness in terms of single layer of n-type organic semiconductor+film thickness in terms of single layer of p-type organic semiconductor)×100) is preferably 15 to 75 volume %, and more preferably 35 to 75 volume %.

It is preferable that the photoelectric conversion film is substantially formed of the specific compound and the n-type organic semiconductor. The term "substantially" means that the total content of the specific compound and the n-type organic semiconductor to the total mass of the photoelectric conversion film is 95 mass % or more.

The n-type organic semiconductor contained in the photoelectric conversion film may be used alone or in combination of two or more.

In addition to the specific compound and the n-type organic semiconductor, the photoelectric conversion film may further contain the p-type organic semiconductor. Examples of the p-type organic semiconductor include the compounds shown below.

The p-type organic semiconductor here means a p-type organic semiconductor which is a compound different from the specific compound. In a case where the photoelectric conversion film contains the p-type organic semiconductor, the p-type organic semiconductor may be used alone or in combination of two or more.

<p-Type Organic Semiconductor>

The p-type organic semiconductor is a donor organic semiconductor material (a compound), and refers to an organic compound having a property of easily donating an electron. More specifically, the p-type organic semiconductor means an organic compound having a smaller ionization potential in a case where two organic compounds are used in contact with each other.

Examples of p-type organic semiconductors include triarylamine compounds (for example, N, N'-bis (3-methylphenyl)-(1,1'-biphenyl)-4,4'-diamine (TPD), 4,4'-bis [N-(naphthyl)-N-Phenyl-amino] biphenyl (α-NPD), the compounds disclosed in paragraphs [0128] to [0148] of JP2011-228614A, the compounds disclosed in paragraphs [0052] to [0063] of JP2011-176259A, the compounds disclosed in paragraphs [0119] to [0158] of JP2011-225544A, the compounds disclosed in paragraphs [0044] to [0051] of JP2015-153910A, and the compounds disclosed in paragraphs [0086] to [0090] of JP2012-094660A, pyrazoline compounds, styrylamine compounds, hydrazone compounds, polysilane compounds, thiophene compounds (for example, a thienothiophene derivative, a dibenzothiophene derivative, a benzodithiophene derivative, a dithienothiophene derivative, a [1] benzothieno [3,2-b] thiophene (BTBT) derivative, a thieno [3,2-f: 4,5-f'] bis [1] benzothiophene (TBBT) derivative, the compounds disclosed in paragraphs [0031] to [0036] of JP2018-014474A, the compounds disclosed in paragraphs [0043] to [0045] of WO2016-194630A, the compounds disclosed in paragraphs [0025] to [0037], and [0099] to [0109] of WO2017-159684A, the compounds disclosed in paragraphs [0029] to [0034] of JP2017-076766A, a cyanine compound, an oxonol compound, a polyamine compound, an indole compound, a pyrrole compound, a pyrazole compound, a polyarylene compound, a fused aromatic carbocyclic compound (for example, a naphthalene derivative, an anthracene derivative, a phenanthrene derivative, a tetracene derivative, a pentacene derivative, a pyrene derivative, a perylene derivative, and a fluoranthene derivative), a porphyrin compound, a phthalocyanine compound, a triazole compound, an oxadiazole compound, an imidazole compound, a polyarylalkane compound, a pyrazolone compound, an amino-substituted chalcone compound, an oxazole compound, a fluorenone compound, a silazane compound, and a metal complex having nitrogen-containing heterocyclic compounds as ligands.

Examples of the p-type organic semiconductor include compounds having an ionization potential smaller than that of the n-type organic semiconductor, and in a case where this condition is satisfied, the organic dyes exemplified as the n-type organic semiconductor can be used.

The compounds that can be used as the p-type semiconductor compound are exemplified below.

61
62
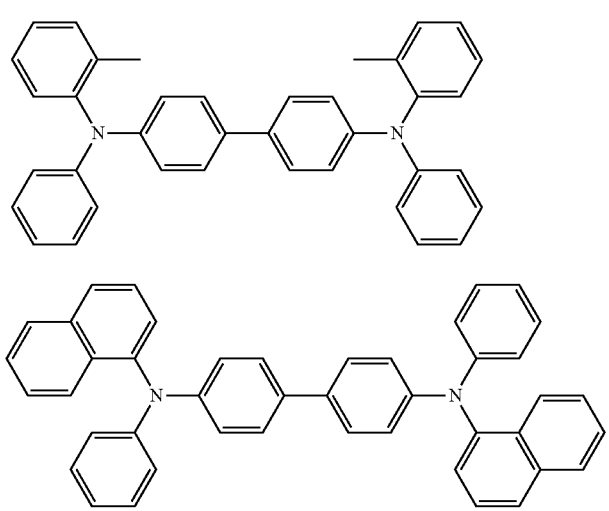
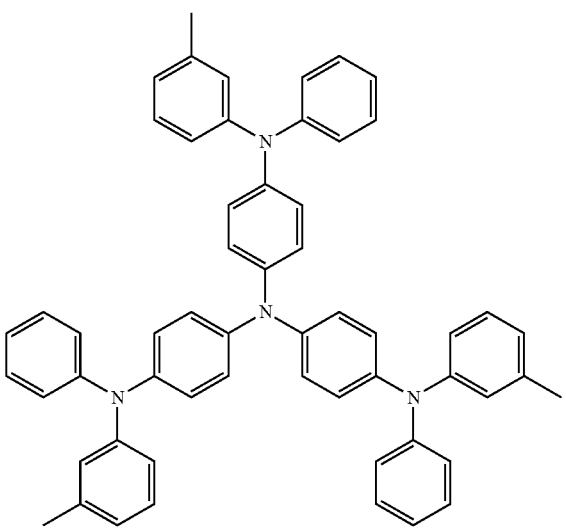
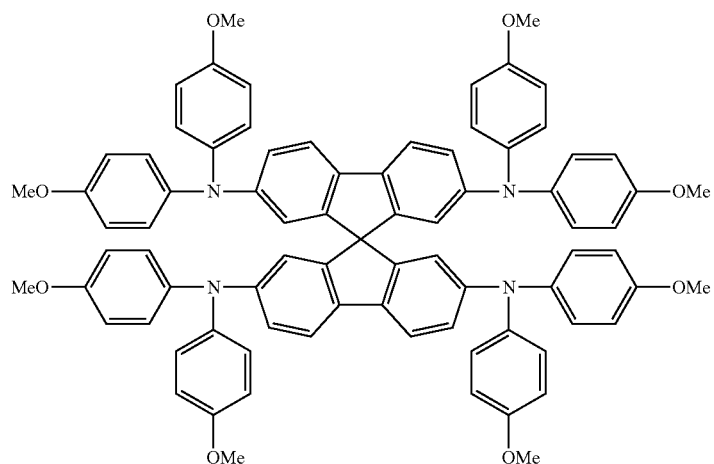
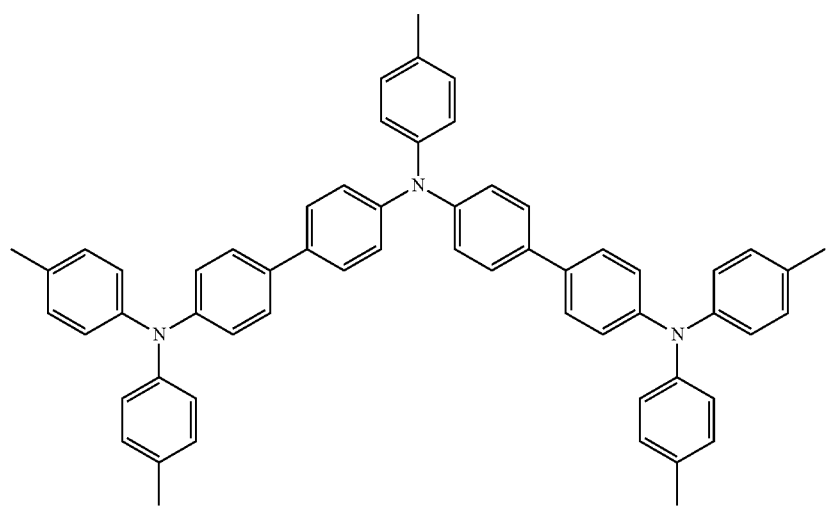

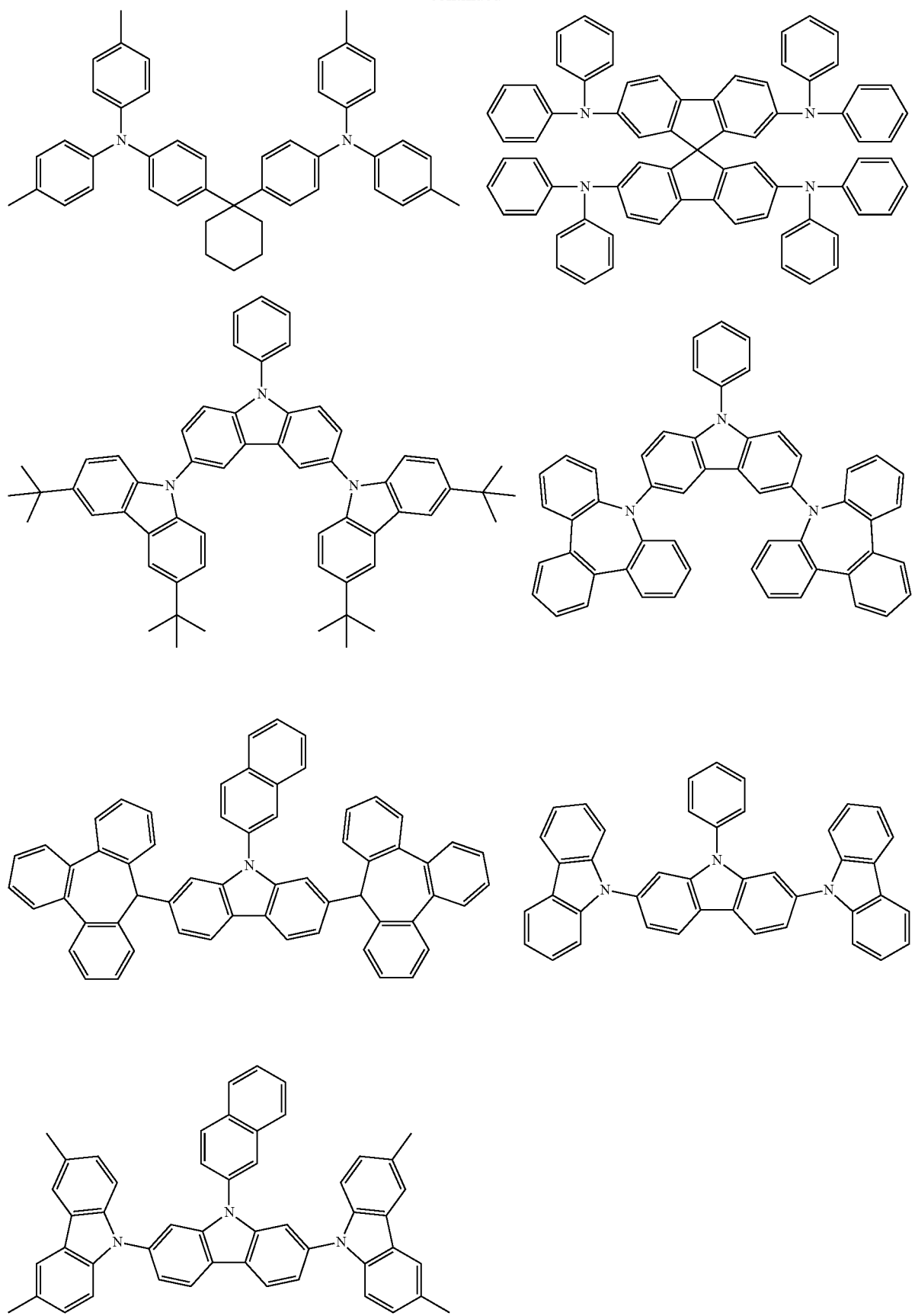

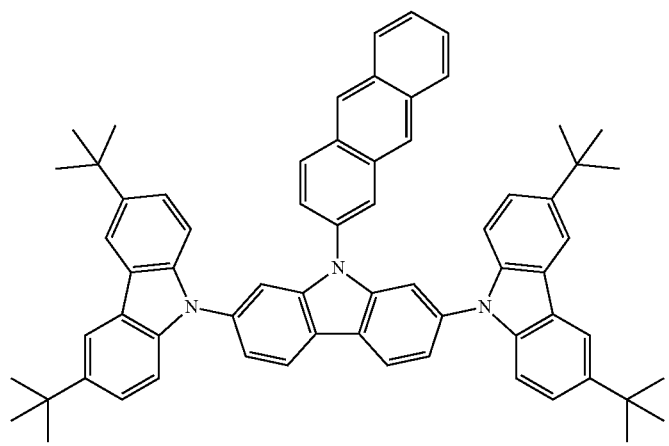
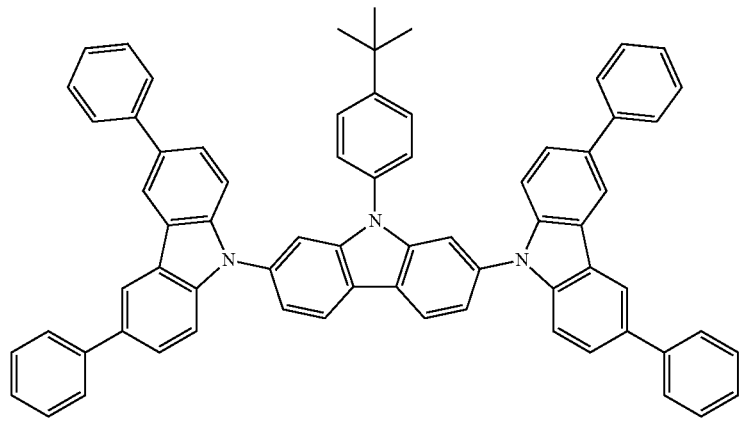
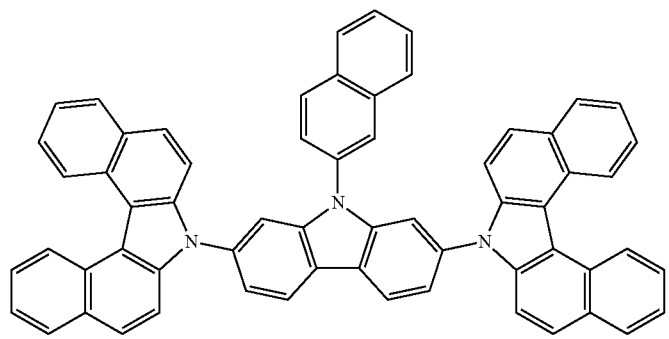
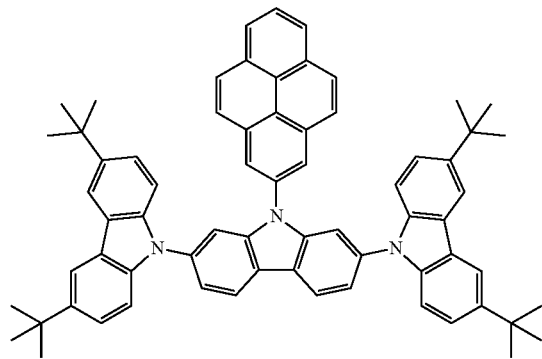
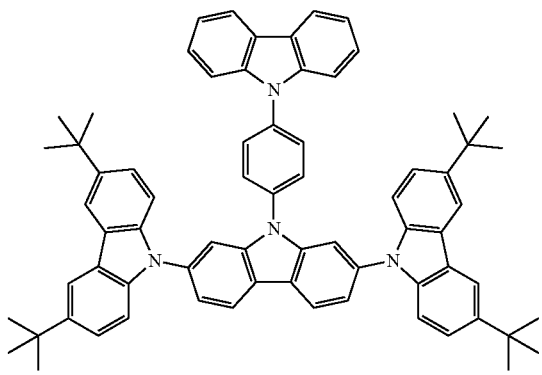

67
68
-continued
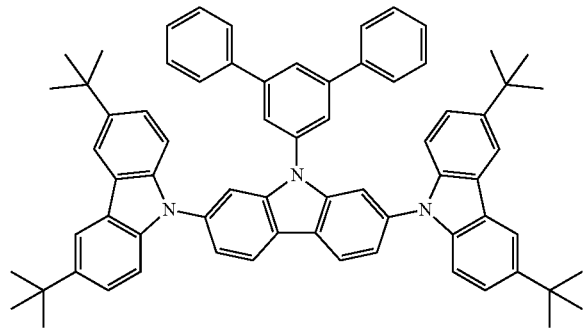
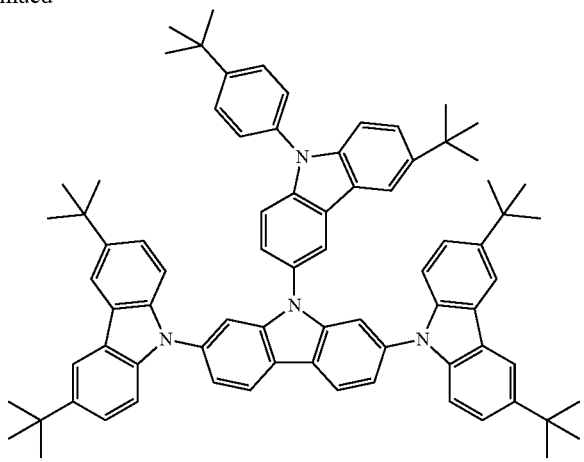
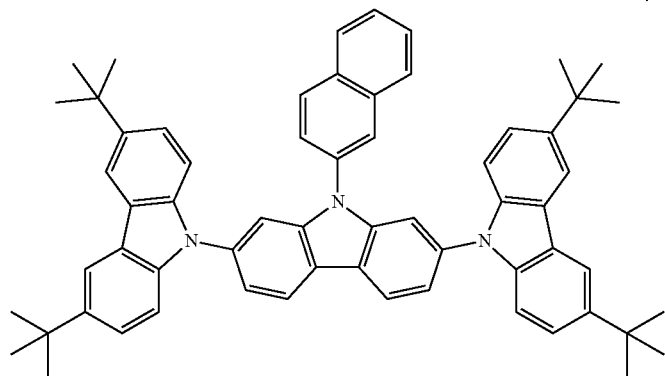
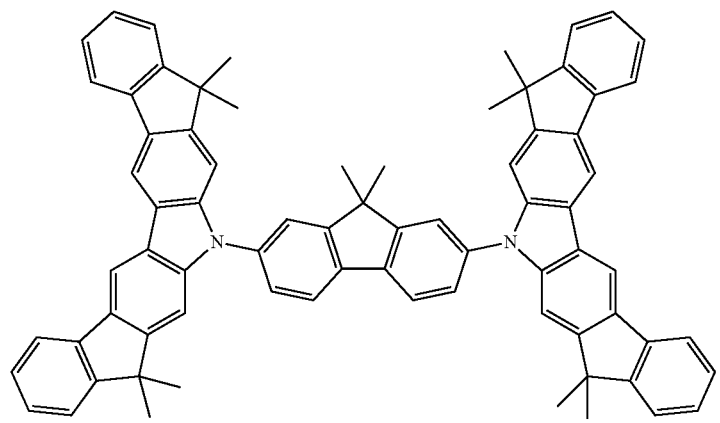
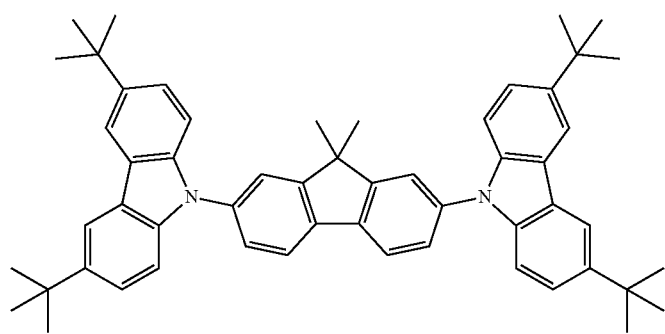

-continued
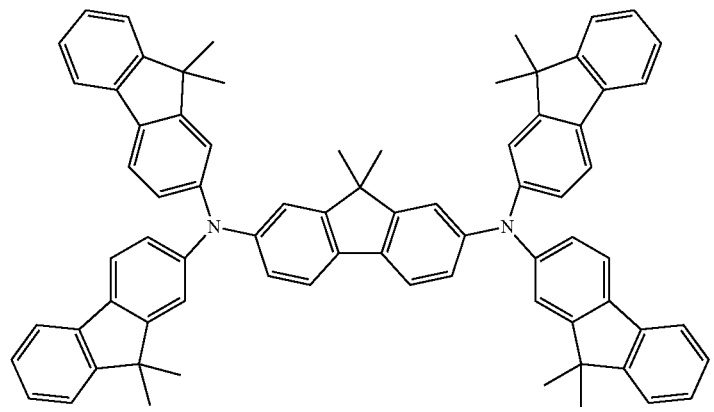
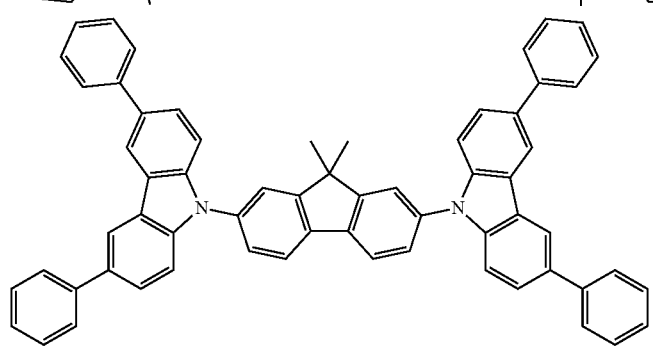
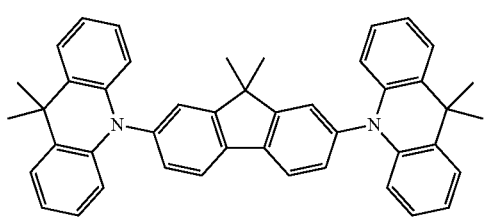
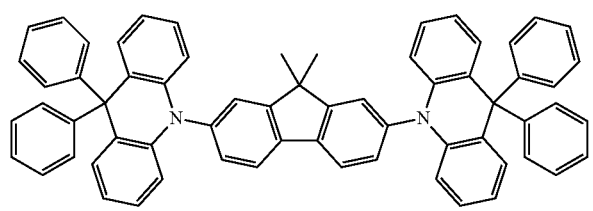
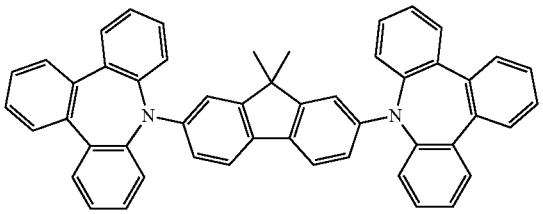
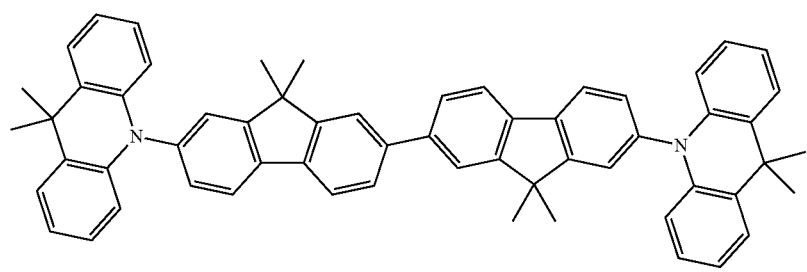
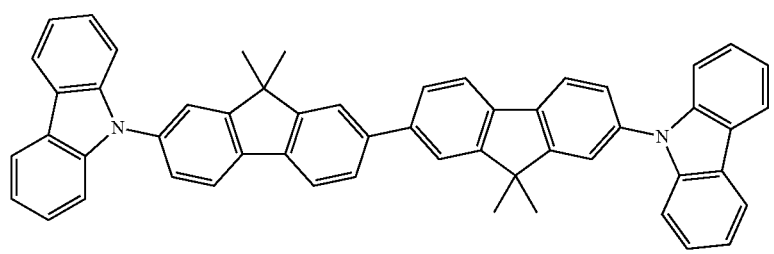

-continued
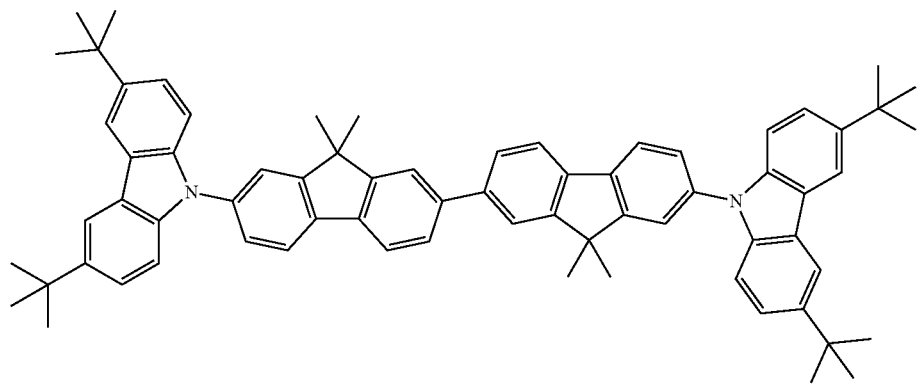
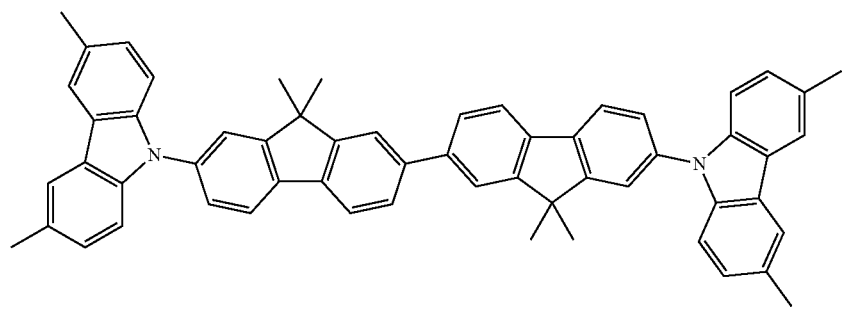
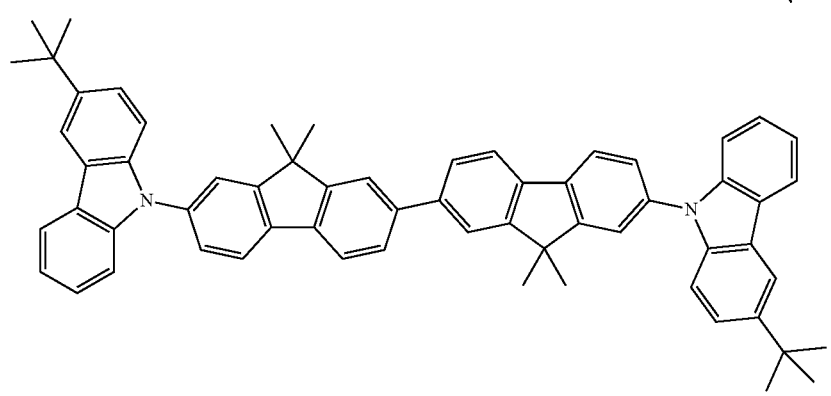
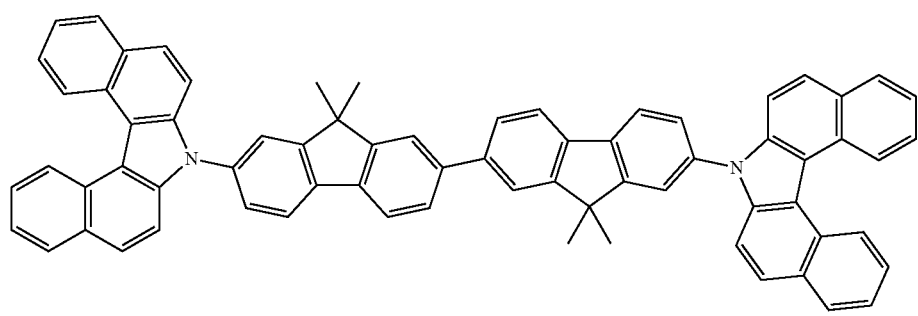
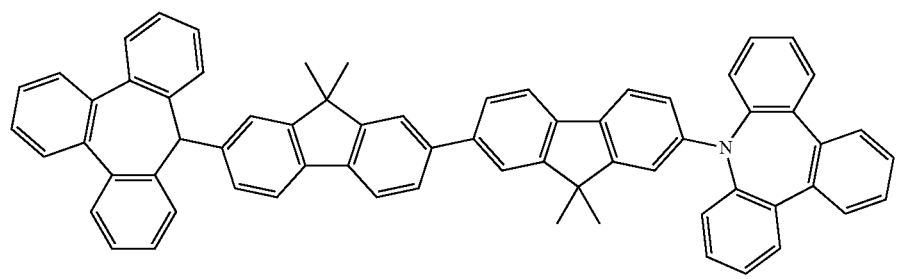

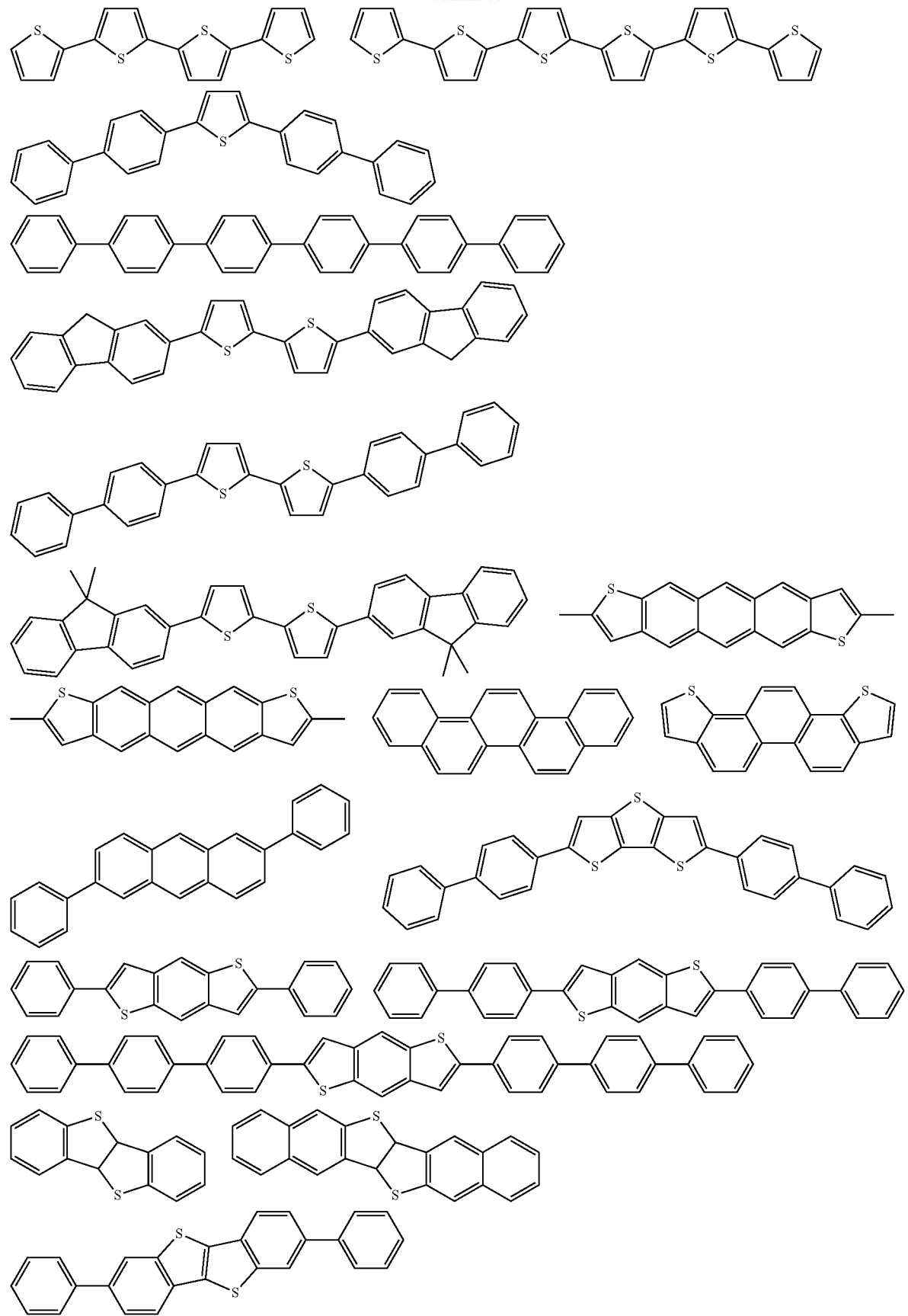

-continued
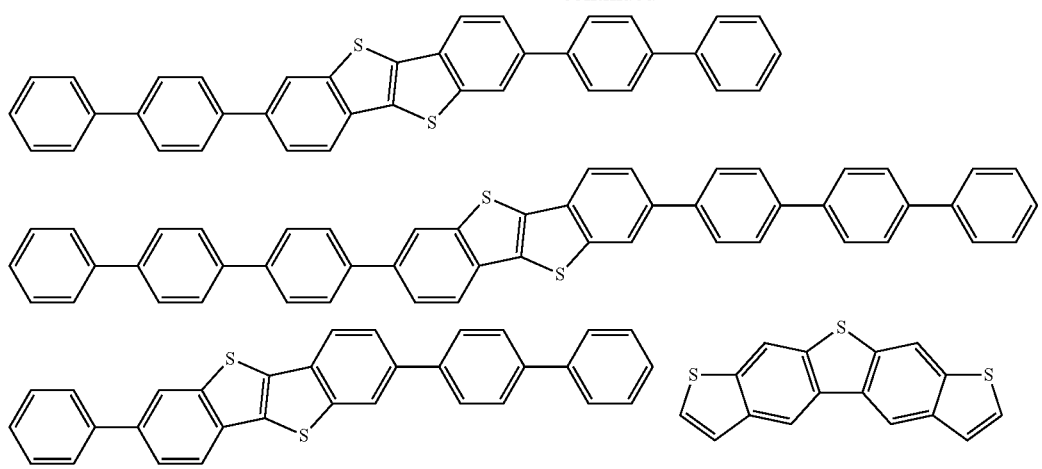
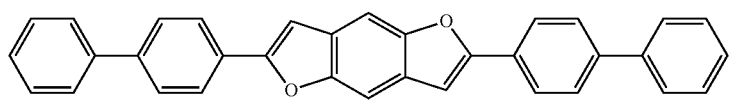
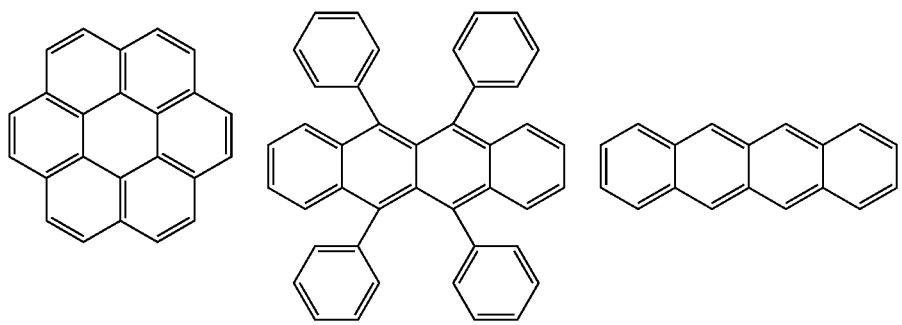
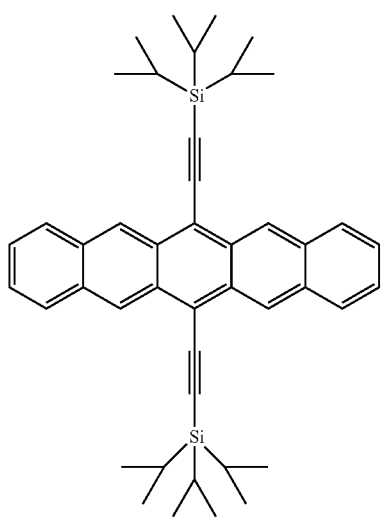

The photoelectric conversion film containing the specific compound is a non-luminescent film, and has a feature different from an organic light emitting diode (OLED). The non-luminescent film means a film having a luminescence quantum efficiency of 1% or less, and the luminescence quantum efficiency is preferably 0.5% or less, and more preferably 0.1% or less.

<Film Formation Method>

The photoelectric conversion film can be formed mostly by a dry film formation method. Examples of the dry film formation method include a physical vapor deposition method such as a vapor deposition method (in particular, a vacuum evaporation method), a sputtering method, an ion plating method, and molecular beam epitaxy (MBE), and chemical vapor deposition (CVD) such as plasma polymerization. Among these, the vacuum evaporation method is preferable. In a case where the photoelectric conversion film is formed by the vacuum evaporation method, producing conditions such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 300 nm.

<Electrode>

The electrode (the upper electrode (the transparent conductive film) 15 and the lower electrode (the conductive film) 11) is formed of a conductive material. Examples of the conductive material include metals, alloys, metal oxides, electrically conductive compounds, and mixtures thereof.

Since light is incident through the upper electrode 15, the upper electrode 15 is preferably transparent to light to be detected. Examples of the material forming the upper electrode 15 include conductive metal oxides such as tin oxide (ATO, FTO) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and the degree of freedom of the range of the film thickness that can be thinned is large. In addition, as the thickness of the upper electrode (the transparent conductive film) 15 is thinner, the amount of light that the upper electrode absorbs becomes smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance thermal vapor deposition method, a chemical reaction method (such as a sol-gel method), and a coating method with a dispersion of indium tin oxide.

<Charge Blocking Film: Electron Blocking Film and Positive Hole Blocking Film>

It is also preferable that the photoelectric conversion element according to the embodiment of the present invention has one or more interlayers between the conductive film and the transparent conductive film, in addition to the photoelectric conversion film. Example of the interlayer includes the charge blocking film. In the case where the photoelectric conversion element has this film, the characteristics (such as photoelectric conversion efficiency and responsiveness) of the photoelectric conversion element to be obtained become superior. Examples of the charge blocking film include the electron blocking film and the positive hole blocking film. Hereinafter, the films will be described in detail.

(Electron Blocking Film)

The electron blocking film is a donor organic semiconductor material (a compound), and the p-type organic semiconductor described above can be used.

A polymer material can also be used as the electron blocking film.

Specific examples of a polymer material include a polymer such as phenylenevinylene, fluorene, carbazole, indole, pyrene, pyrrole, picoline, thiophene, acetylene, and diacetylene, and a derivative thereof.

The electron blocking film may be configured by a plurality of films.

The electron blocking film may be formed of an inorganic material. In general, an inorganic material has a dielectric constant larger than that of an organic material. Therefore, in a case where the inorganic material is used in the electron blocking film, a large voltage is applied to the photoelectric conversion film. Therefore, the photoelectric conversion efficiency increases. Examples of the inorganic material that can be used in the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

(Positive Hole Blocking Film)

A positive hole blocking film is an acceptor-property organic semiconductor material (a compound), and the n-type organic semiconductor described above can be used.

The method of producing the charge blocking film is not particularly limited, but a dry film formation method and a wet film formation method are exemplified. Examples of the dry film formation method include a vapor deposition method and a sputtering method. The vapor deposition method may be any of physical vapor deposition (PVD) method and chemical vapor deposition (CVD) method, and physical vapor deposition method such as vacuum evaporation method is preferable. Examples of the wet film formation method include an inkjet method, a spray method, a nozzle printing method, a spin coating method, a dip coating method, a casting method, a die coating method, a roll coating method, a bar coating method, and a gravure coating method, and an inkjet method is preferable from the viewpoint of high precision patterning.

Each thickness of the charge blocking films (the electron blocking film and the positive hole blocking film) is preferably 3 to 200 nm, more preferably 5 to 100 nm, and still more preferably 5 to 30 nm.

<Substrate>

The photoelectric conversion element may further include a substrate. The type of substrate to be used is not particularly limited, but a semiconductor substrate, a glass substrate, and a plastic substrate are exemplified.

The position of the substrate is not particularly limited, but in general, the conductive film, the photoelectric conversion film, and the transparent conductive film are laminated on the substrate in this order.

<Sealing Layer>

The photoelectric conversion element may further include a sealing layer. The performance of the photoelectric conversion material may deteriorate noticeably due to the presence of deterioration factors such as water molecules. The deterioration can be prevented by sealing and coating the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be produced according to the description in paragraphs [0210] to [0215] of JP2011-082508A.

<Imaging Element>

An example of the application of the photoelectric conversion element includes an imaging element. The imaging element is an element that converts optical information of an image into an electric signal, and usually, a plurality of photoelectric conversion elements are arranged in a matrix on the same plane, and an optical signal is converted into the electric signal in each photoelectric conversion element (pixels) to sequentially output the electric signal to the outside of the imaging element for each pixel. Therefore, each pixel is formed of one or more photoelectric conversion elements and one or more transistors.

Figure 3:
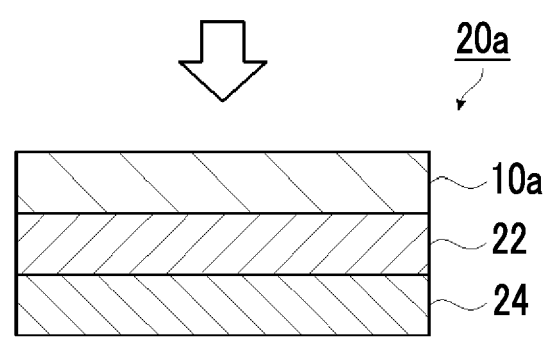
FIG. 3 is a schematic cross-sectional view of one embodiment of an imaging element.

FIG. 3 is a schematic cross-sectional view showing a schematic configuration of an imaging element for describing an embodiment of the present invention. This imaging element is mounted on an imaging element such as a digital camera and a digital video camera, an electronic endoscope, and imaging modules such as a cellular phone.

An imaging element 20a shown in FIG. 3 includes a photoelectric conversion element 10a according to the embodiment of the present invention, a blue photoelectric conversion element 22, and a red photoelectric conversion element 24, which are laminated along the light incident direction. As described above, the photoelectric conversion element 10a can mainly function as a green photoelectric conversion element capable of receiving green light.

The imaging element 20a is a so-called laminated type color separation imaging element. The photoelectric conversion element 10a, the blue photoelectric conversion element 22, and the red photoelectric conversion element 24 have different wavelength spectra to be detected. That is, the blue photoelectric conversion element 22 and the red photoelectric conversion element 24 correspond to photoelectric conversion elements that receive (absorb) light having a wavelength different from a wavelength of the light received by the photoelectric conversion element 10a. The photoelectric conversion element 10a can mainly receive green light, the blue photoelectric conversion element 22 can mainly receive blue light, and the red photoelectric conversion element can mainly receive red light.

Green light means light in the wavelength range of 500 to 600 nm, blue light means light in the wavelength range of 400 to 500 nm, and red light means light in the wavelength range of 600 to 700 nm.

In a case where light is incident on the imaging element 20a in the direction of the arrow, first, green light is mainly absorbed by the photoelectric conversion element 10a, but blue light and red light are transmitted through the photoelectric conversion element 10a. In a case where the light transmitted through the photoelectric conversion element 10a travels to the blue photoelectric conversion element 22, the blue light is mainly absorbed, but the red light is transmitted through the blue photoelectric conversion element 22. Then, light transmitted through the blue photoelectric conversion element 22 is absorbed by the red photoelectric conversion element 24. As described above, in the imaging element 20a, which is a laminated type color separation imaging element, one pixel can be configured with three light receiving sections of green, blue, and red, and a large area of the light receiving section can be taken.

In particular, the photoelectric conversion element 10a according to the embodiment of the present invention has a narrow absorption peak half-width, and thus absorptions of blue light and red light do not occur, and it is difficult to affect the detectability of the blue photoelectric conversion element 22 and the red photoelectric conversion element 24.

The configurations of the blue photoelectric conversion element 22 and the red photoelectric conversion element 24 are not particularly limited.

For example, the photoelectric conversion element having a configuration in which colors are separated by using silicon using a difference in light absorption length may be used. As a more specific example, both the blue photoelectric conversion element 22 and the red photoelectric conversion element 24 may be made of silicon. In this case, as for the light including the blue light, the green light, and the red light that has entered the imaging element 20a in the direction of the arrow, the photoelectric conversion element 10a mainly receives the green light having the center wavelength, and the remaining blue light and red light are easily separated. Blue light and red light have different light absorption lengths for silicon (wavelength dependence of absorption coefficient for silicon), blue light is easily absorbed near the surface of silicon, and red light can penetrate deeper into the silicon. Based on such a difference in light absorption length, blue light is mainly received by the blue photoelectric conversion element 22 existing in a shallower position, and red light is mainly received by the red photoelectric conversion element 24 existing in a deeper position.

Further, the blue photoelectric conversion element 22 and the red photoelectric conversion element 24 may be the photoelectric conversion element (the blue photoelectric conversion element 22 or the red photoelectric conversion element 24) having a configuration including a conductive film, an organic photoelectric conversion film having a maximum absorption wavelength for blue light or red light, and the transparent conductive film in this order.

In FIG. 3, the photoelectric conversion element according to the embodiment of the present invention, the blue photoelectric conversion element, and the red photoelectric conversion element are arranged in this order from the light incident side, but the arrangement is not limited to the aspect, and may be another aspect. For example, the blue photoelectric conversion element, the photoelectric conversion element according to the embodiment of the present invention, and the red photoelectric conversion element may be arranged in this order from the light incident side.

As described above, the configuration in which the photoelectric conversion elements of the three primary colors of blue, green, and red are laminated as the imaging element is described, but the configuration may be two layers (two colors) or four layers (four colors) or more.

For example, the photoelectric conversion element 10*a* according to the embodiment of the present invention may be arranged on the arrayed blue photoelectric conversion element 22 and red photoelectric conversion element 24. As needed, a color filter that absorbs light of a predetermined wavelength may be arranged on the light incident side.

The form of the imaging element is not limited to the forms shown in FIG. 3 and may be other forms.

For example, the photoelectric conversion element according to the embodiment of the present invention, the blue photoelectric conversion element, and the red photoelectric conversion element may be arranged in the same plane position.

Alternatively, the photoelectric conversion element may be used in a single layer. For example, blue, red, and green color filters may be arranged on the photoelectric conversion element 10*a* according to the embodiment of the present invention.

Examples of another application of the photoelectric conversion element include the photoelectric cell and the optical sensor, but the photoelectric conversion element according to the embodiment of the present invention is preferably used as the optical sensor. The photoelectric conversion element may be used alone as the optical sensor. Alternately, the photoelectric conversion element may be used as a line sensor in which the photoelectric conversion elements are linearly arranged or as a two-dimensional sensor in which the photoelectric conversion elements are planarly arranged.

Examples

Hereinafter, the present invention will be described in more detail with reference to examples. The materials, usage amounts, proportion, processing contents, and processing procedures shown in the following examples can be appropriately changed without departing from the spirit of the present invention. Therefore, the scope of the present invention should not be construed as being limited by the following examples.

<Synthesis of Compound (D-1)>

A compound (D-1) was synthesized according to the following scheme.

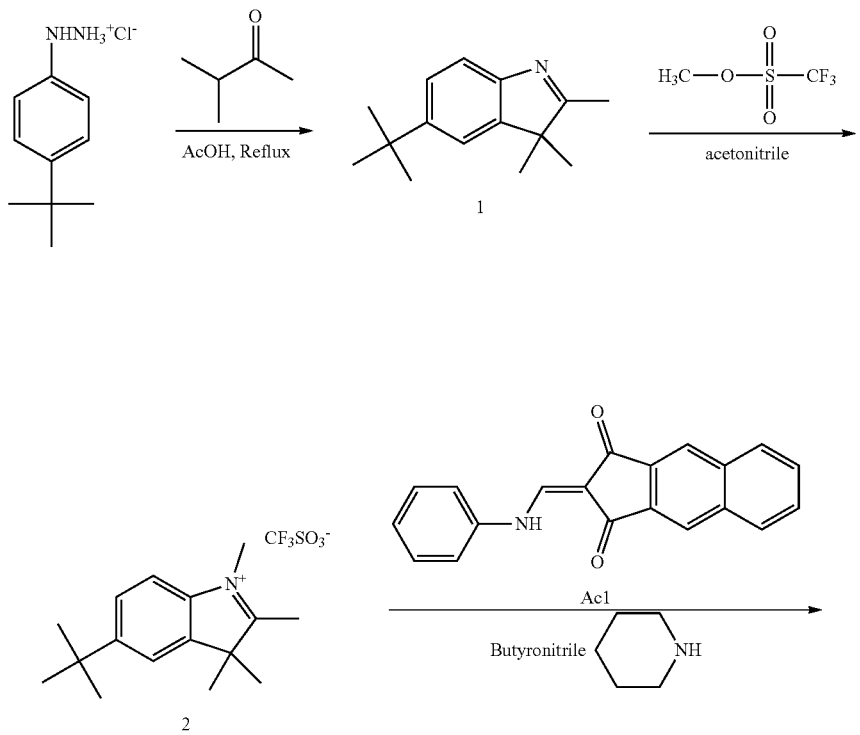

-continued

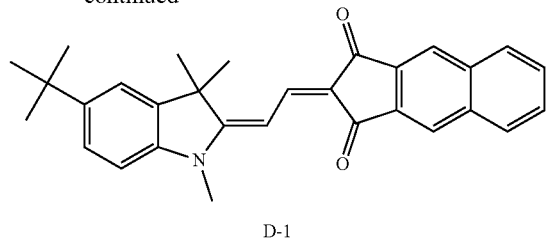

D-1

4-Tert-Butylphenylhydrazine hydrochloride (5.00 g, 24.9 mmol) and 3-methyl-2-butanone (2.58 g, 29.9 mmol) were added to acetic acid (62.5 mL), and the obtained solution was heated and refluxed for 3 hours under a nitrogen atmosphere. The obtained solution was cooled to room temperature, the organic layer was extracted with methyl-tert-butyl ether (MTBE), the obtained extract was washed with brine, and the washed extract was concentrated under reduced pressure to obtain the concentrated residue containing a compound 1.

Acetonitrile (40 mL) and methyl trifluoromethanesulfonate (7.14 g, 43.5 mmol) were added to the concentrated residue, and the obtained solution was heated and refluxed for 3 hours under a nitrogen atmosphere. In a case where MTBE (80 mL) was added to the obtained solution, the obtained solution was separated into a solid containing a compound 2 and the MTBE solution, and the MTBE solution was removed by decantation. MTBE (80 mL) was added to the solid containing the compound 2 to perform dispersion washing, and MTBE was removed by decantation to obtain the compound 2 (3.54 g, 9.33 mmol, yield 37%) as an orange solid.

The compound 2 (1.70 g, 4.48 mmol), Ac1 (1.22 g, 4.07 g) (synthesized according to paragraphs [0080] to [0084] of JP5337381B), and piperidine (0.8 mL) were added to butyronitrile (62.5 mL), and the obtained solution was heated and refluxed for 48 hours under a nitrogen atmosphere. The obtained solution was cooled to room temperature, the precipitated solid was collected by filtration, and the obtained solid was washed with acetonitrile to obtain a crude product. The obtained crude product was purified by silica gel column chromatography (chloroform:ethyl acetate=9:1), and the obtained compound was recrystallized from a chloroform-acetonitrile mixed solvent and washed with acetonitrile to obtain a compound (D-1) (1.20 g, 2.76 mmol, yield 61%).

The obtained compound (D-1) was identified by nuclear magnetic resonance (NMR) and mass spectrometry (MS).

Figure 4:
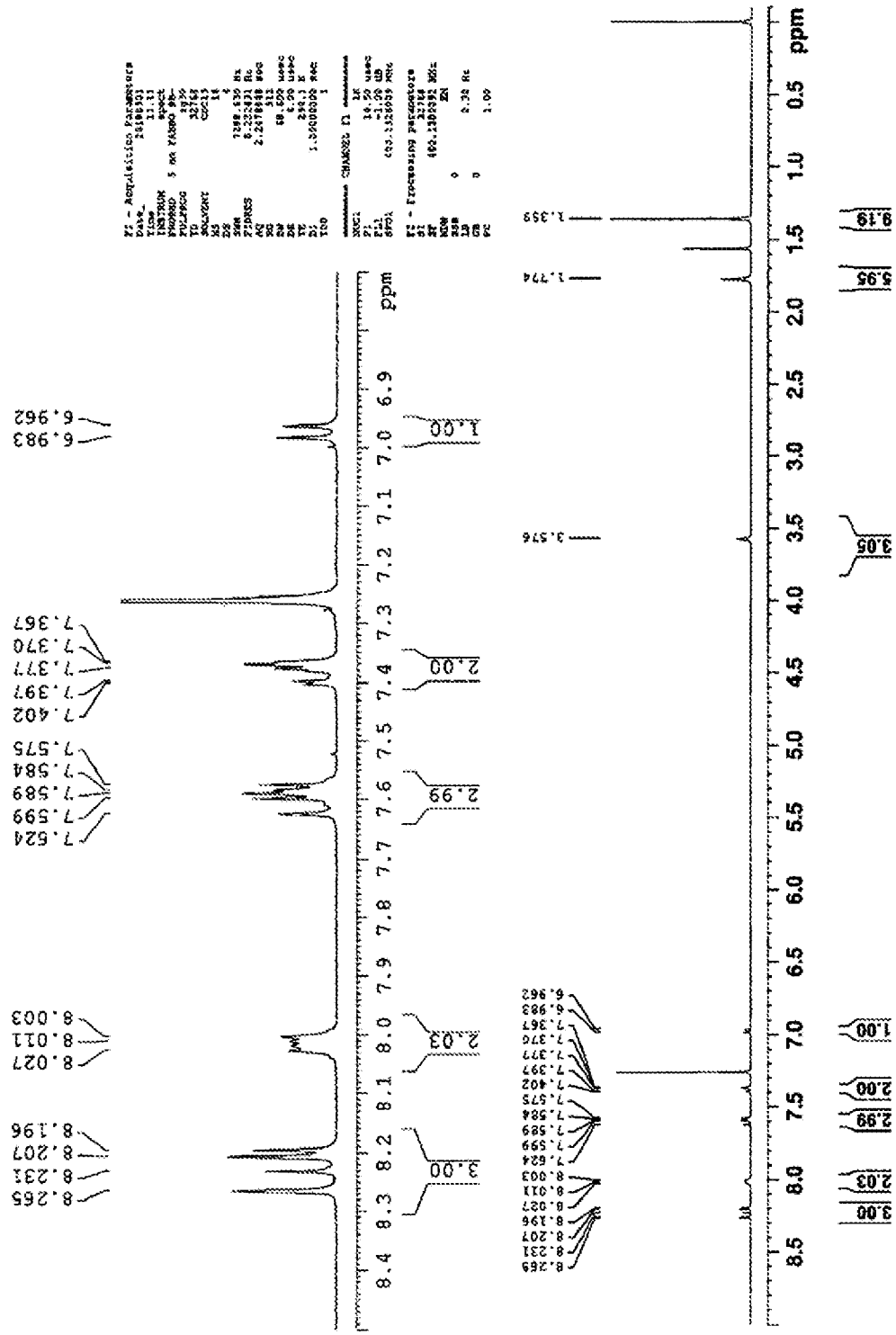
FIG. 4 is a $^1$H•NMR spectrum of a compound (D-1).

$^1$H NMR spectrum (400 MHz, CDCl$_3$) is shown in FIG. 4.

MS(ESI$^+$)m/z: 436.6 ([M+H]$^+$)

<Synthesis of Compound (D-2)>

A compound (D-2) was synthesized according to the following scheme.

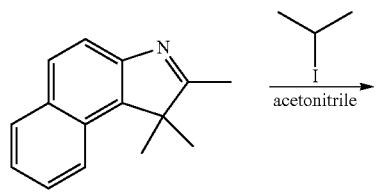

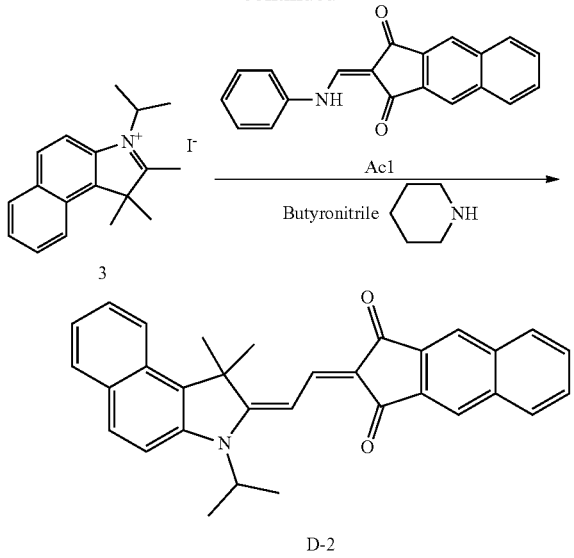

D-2

Acetonitrile (77 mL) and 2-iodopropane (25.0 g, 147 mmol) were added to 1,1,2-trimethyl-1H-benzo [e] indole (7.69 g, 36.8 mmol), and the obtained solution was heated and refluxed for 48 hours under a nitrogen atmosphere. After the obtained solution was cooled to room temperature, the precipitated powder was collected by filtration. The obtained powder was dispersed and washed with toluene, the powder was collected by filtration, and the collected powder was washed with MTBE to obtain a compound 3 (4.00 g, 10.5 mmol, yield 29%) as a white powder.

The compound 3 (4.00 g, 11.3 mmol), Ac1 (2.87 g, 9.59 mmol), and piperidine (2.66 mL) were added to butyronitrile (80 mL), and the obtained solution was heated and refluxed for 48 hours under a nitrogen atmosphere. The obtained solution was cooled to room temperature, the precipitated solid was collected by filtration, and the collected solid was washed with acetonitrile to obtain a crude product. The obtained crude product was purified by silica gel column chromatography (chloroform:ethyl acetate=9:1), and the obtained compound was recrystallized from a chloroform-acetonitrile mixed solvent and washed with acetonitrile to obtain a compound (D-2) (0.99 g, 2.16 mmol, yield 23%).

The obtained compound (D-2) was identified by NMR and MS.

Figure 5:
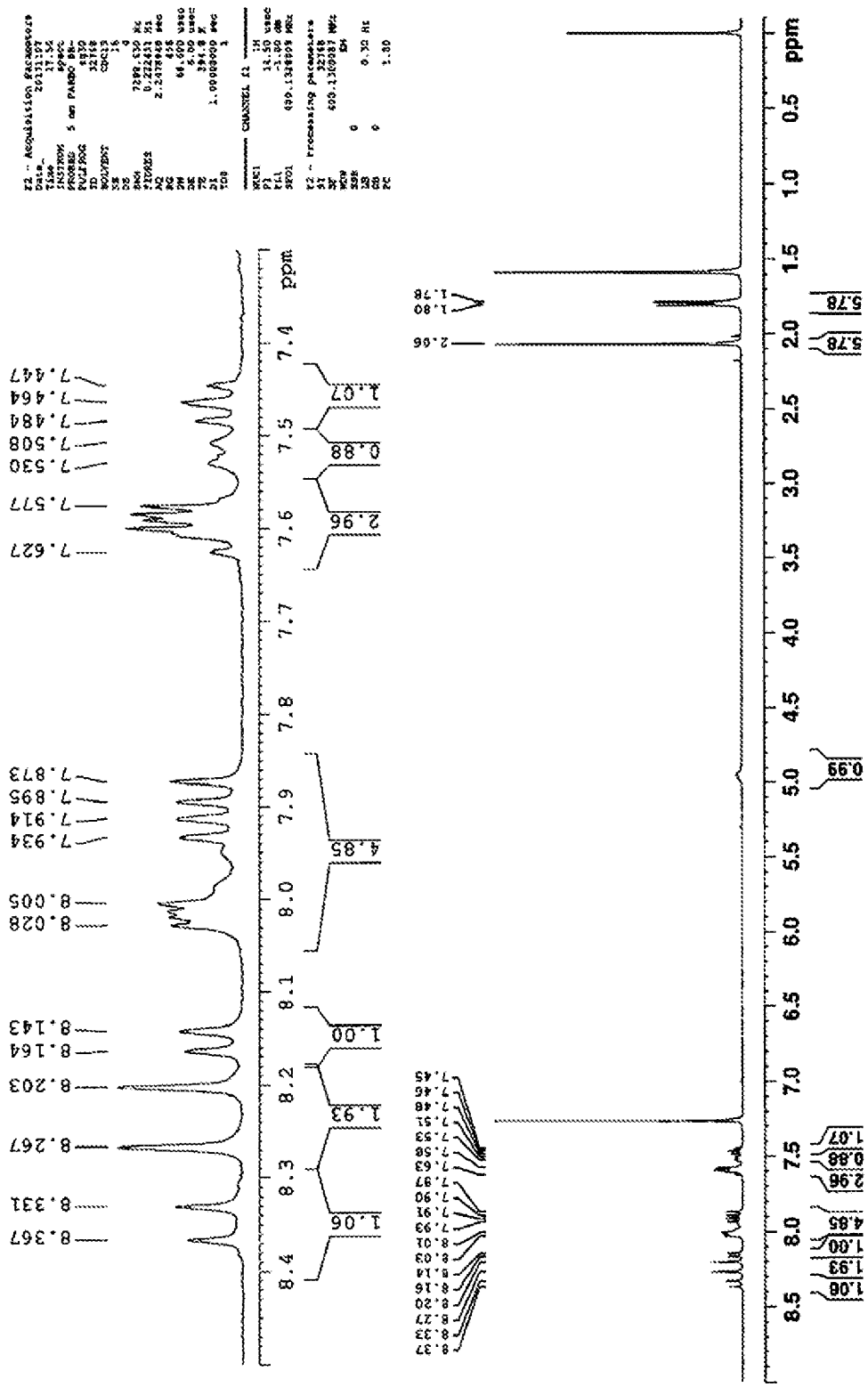
FIG. 5 is a $^1$H•NMR spectrum of a compound (D-2).

$^1$H NMR spectrum (400 MHz, CDCl$_3$) is shown in FIG. 5.

MS(ESI$^+$)m/z: 458.7 ([M+H]$^+$)

<Synthesis of Compound (D-3)>

A compound (D-3) was synthesized according to the following scheme.

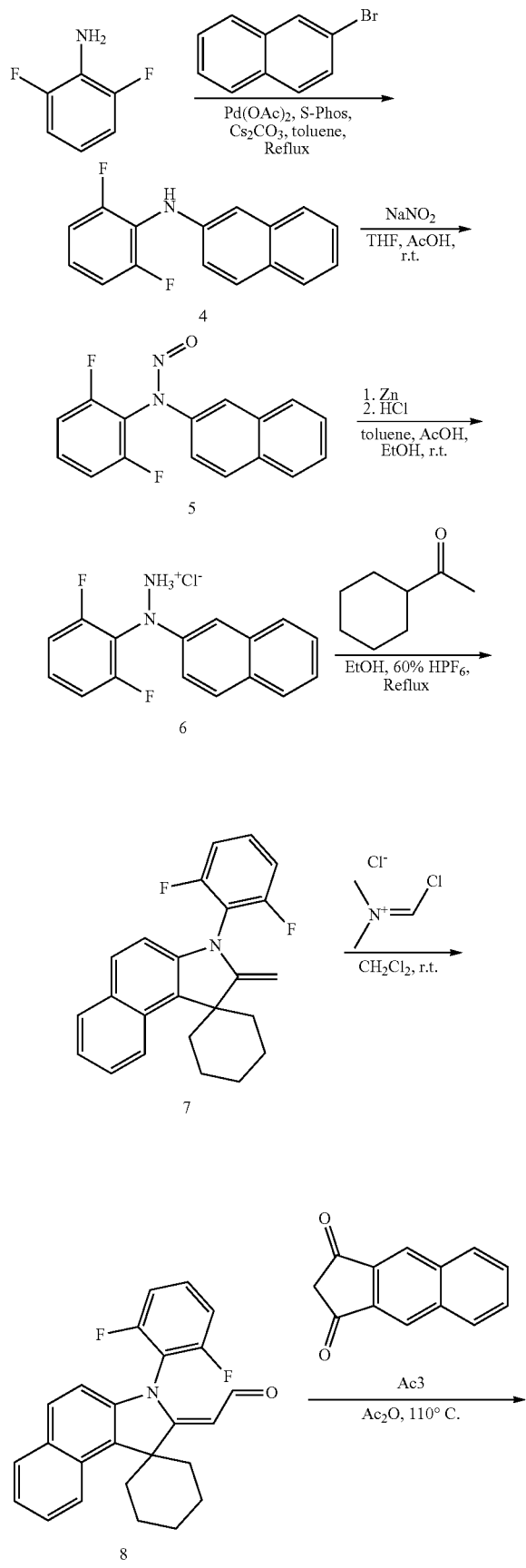

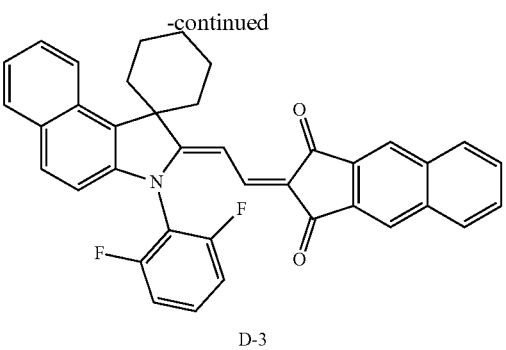

D-3

2,6-Difluoroaniline (46.7 g, 362 mmol), 2-bromonaphthalene (50.0 g, 241 mmol), palladium (II) acetate (1.62 g, 7.23 mmol), 2-dicyclohexylphosphino-2',6'-Dimethoxybiphenyl (S-Phos) (5.94 g, 14.5 mmol), cesium carbonate (157 g, 481 mmol), and toluene (500 mL) were placed in a three-necked flask of 2 L, and degassing and nitrogen gas replacement were performed. The solution in the flask was heated to 110° C. under a nitrogen atmosphere and stirred for 12 hours. Then, after cooling the solution to room temperature, the solution was added to water. The obtained organic layer was extracted with ethyl acetate, the obtained extract was washed with brine, and the washed extract was concentrated under reduced pressure. The concentrated residue was purified by silica gel column chromatography (toluene:hexane=1:1) to obtain a compound 4 (49.3 g, 193 mmol, yield 80%) as a pale yellow solid.

A compound 4 (40 g, 178 mmol) was added to a mixed solvent of tetrahydrofuran (200 mL) and acetic acid (200 mL), and the obtained solution was added with an aqueous sodium nitrite solution (87.8 mL, 356 mmol) dropwise at room temperature and reacted for 20 minutes. The obtained solution was extracted with toluene (434 mL), the obtained extract was washed with water (434 mL), and the aqueous layer was removed. Water (88 mL) and ethanol (88 mL) were added to the obtained organic layer containing a compound 5, and the obtained solution was cooled to 0° C. in an ice bath to add zinc powder (81.5 g, 1.25 mmol). After acetic acid (88 mL) was added dropwise to the obtained solution so as not to exceed 10° C., the obtained solution was reacted at room temperature for 2 hours. The insoluble matter was filtered from the solution, the filtrate was collected, brine (434 mL) was added to the filtrate to wash the organic layer, and the collected organic layer was concentrated under reduced pressure to about 150 mL. MTBE (400 mL) and 30% hydrochloric acid (43.3 g, 356 mmol) were added to the concentrated solution, and the mixture was stirred. The precipitated powder in the solution was filtered to collect the solid, and the collected solid was washed with MTBE and isopropanol and then dried by heating to obtain a compound 6 (21.8 g, 71.1 mmol, yield 36%).

A compound 6 (8.00 g, 26.1 mmol), cyclohexyl methyl ketone (3.62 g, 28.7 mmol), and 60% hexafluorophosphoric acid (7.23 mL) were added to ethanol (80 mL) and the obtained solution was heated and refluxed for 2 hours under a nitrogen atmosphere. The obtained solution was cooled to room temperature, 10M aqueous sodium hydroxide solution (100 mL) was added to the solution for neutralization, the organic layer was extracted with MTBE, and the obtained extract was washed with brine, and the washed extract was concentrated under reduced pressure to about 20 mL.

MTBE (150 mL) and 60% hexafluorophosphoric acid (7.23 mL, 52.2 mmol) were added to the concentrated solution, and the mixture was stirred. The salt of a compound 7 precipitated in the solution was collected by filtration, and the collected solid was washed with MTBE. The salt of the obtained compound 7 was added to dichloromethane (200 mL), and a 2M aqueous sodium hydroxide solution (200 mL) was added dropwise to the solution to neutralize and dissolve in dichloromethane. Dichloromethane was concentrated under reduced pressure to obtain the compound 7 (1.13 g, 3.13 mmol, yield 12%).

Under a nitrogen atmosphere, (chloromethylene) dimethyliminium (800 mg, 6.25 mmol) was added to dichloromethane (11 mL), and cooled to 0° C. in an ice bath. A dichloromethane solution (11 mL) of the compound 7 (1.13 g, 3.13 mmol) was added dropwise to the obtained solution, and the mixture was reacted at room temperature for 2 hours. A 2M aqueous sodium hydroxide solution (100 mL) was added dropwise to the obtained solution to cause hydrolysis. The obtained organic layer was extracted with dichloromethane, the obtained extract was washed with brine, and the washed extract was concentrated under reduced pressure. The concentrated residue was purified by silica gel column chromatography (chloroform:ethyl acetate=99:1) to obtain a compound 8 (900 mg, 2.31 mmol, yield 74%) as a pale yellow solid.

A compound 8 (900 mg, 2.31 mmol) and Ac3 (453 mg, 2.31 mmol) were added to acetic anhydride (16 mL), and the obtained solution was reacted at 110° C. for 2 hours under a nitrogen atmosphere. After the obtained solution was cooled to room temperature and the solvent was removed by concentration under reduced pressure, the obtained crude product was purified by silica gel column chromatography (chloroform:ethyl acetate=9:1), and the obtained compound was recrystallized from a chloroform-acetonitrile mixed solvent and washed with acetonitrile to obtain a compound (D-3) (1.00 g, 1.76 mmol, yield 76%).

The obtained compound (D-3) was identified by NMR and MS.

Figure 6:
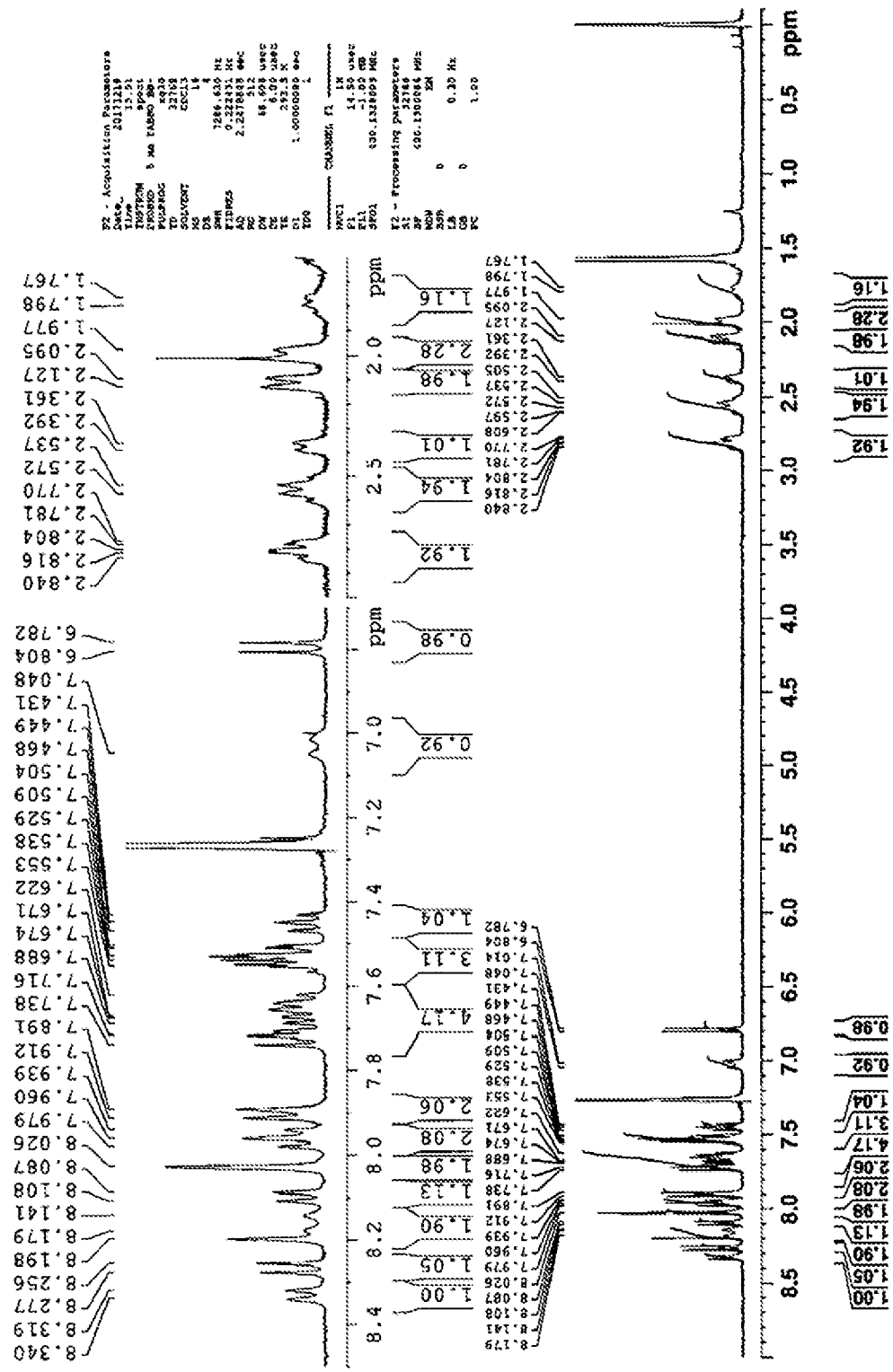
FIG. 6 is a $^1$H•NMR spectrum of a compound (D-3).

$^1$H NMR spectrum (400 MHz, CDCl$_3$) is shown in FIG. 6.

MS(ESI$^+$)m/z: 568.5 ([M+H]$^+$)

<Synthesis of Compound (D-4)>

A compound (D-4) was synthesized according to the following scheme.

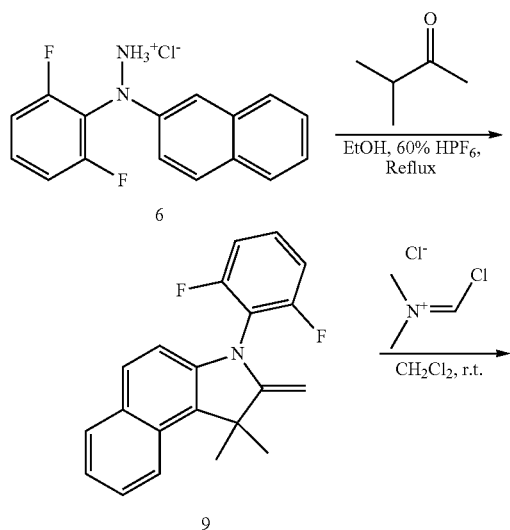

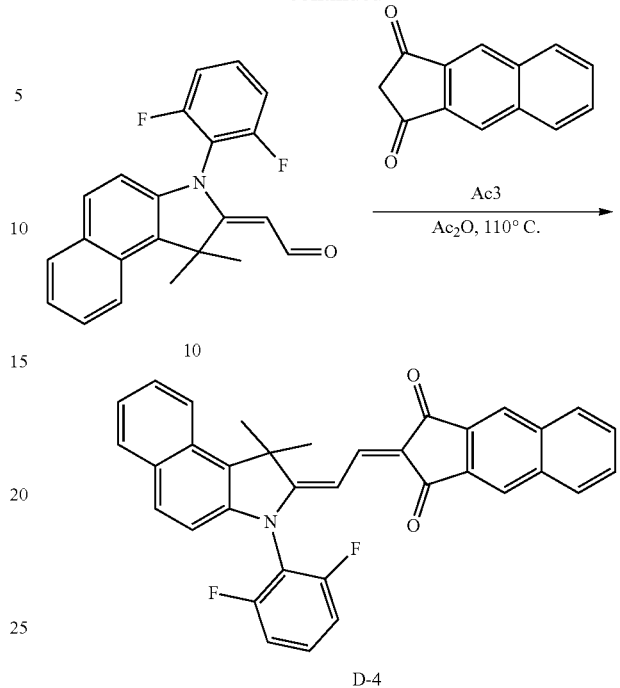

A compound 6 (3.00 g, 9.83 mmol), 3-methyl-2-butanone (1.27 g, 14.7 mmol), and 60% hexafluorophosphoric acid (2.71 mL) were added to ethanol (30 mL) and the obtained solution was heated and refluxed for 2 hours under a nitrogen atmosphere. The obtained solution was cooled to room temperature, 10M aqueous sodium hydroxide solution (50 mL) was added to the solution for neutralization, the organic layer was extracted with MTBE, and the obtained extract was washed with brine, and the washed extract was concentrated under reduced pressure. MTBE (150 mL) and 60% hexafluorophosphoric acid (2.71 mL, 19.7 mmol) were added to the concentrated solution, and the mixture was stirred. The salt of a compound 9 precipitated in the solution was collected by filtration, and the collected solid was washed with MTBE. The salt of the obtained compound 9 was added to dichloromethane (100 mL), and a 2M aqueous sodium hydroxide solution (100 mL) was added dropwise to neutralize and dissolve in dichloromethane. The obtained dichloromethane was concentrated under reduced pressure to obtain the compound 9 (2.30 g, 7.16 mmol, yield 49%).

Under a nitrogen atmosphere, (chloromethylene) dimethyliminium (1.37 g, 10.7 mmol) was added to dichloromethane (23 mL), and the obtained solution was cooled to 0° C. in an ice bath. A dichloromethane solution (23 mL) of the compound 9 (2.30 g, 7.16 mmol) was added dropwise to the solution, and the mixture was reacted at room temperature for 2 hours. A 2M aqueous sodium hydroxide solution (100 mL) was added dropwise to the obtained solution to cause hydrolysis. The organic layer was extracted with dichloromethane, the obtained extract was washed with brine, and the washed extract was concentrated under reduced pressure. The concentrated residue was purified by silica gel column chromatography (chloroform:ethyl acetate=99:1) to obtain a compound 10 (1.28 g, 3.66 mmol, yield 51%) as a pale yellow solid.

A compound 10 (1.28 g, 3.66 mmol) and Ac3 (719 mg, 3.66 mmol) were added to acetic anhydride (26 mL), and the obtained solution was reacted at 110° C. for 2 hours under a nitrogen atmosphere. After the obtained solution was cooled to room temperature and the solvent was removed by concentration under reduced pressure, the obtained crude product was purified by silica gel column chromatography (chloroform:ethyl acetate=9:1), and the obtained compound was recrystallized from a chloroform-acetonitrile mixed solvent and washed with acetonitrile to obtain a compound (D-4) (1.15 g, 2.18 mmol, yield 60%).

The obtained compound (D-4) was identified by NMR and MS.

Figure 7:
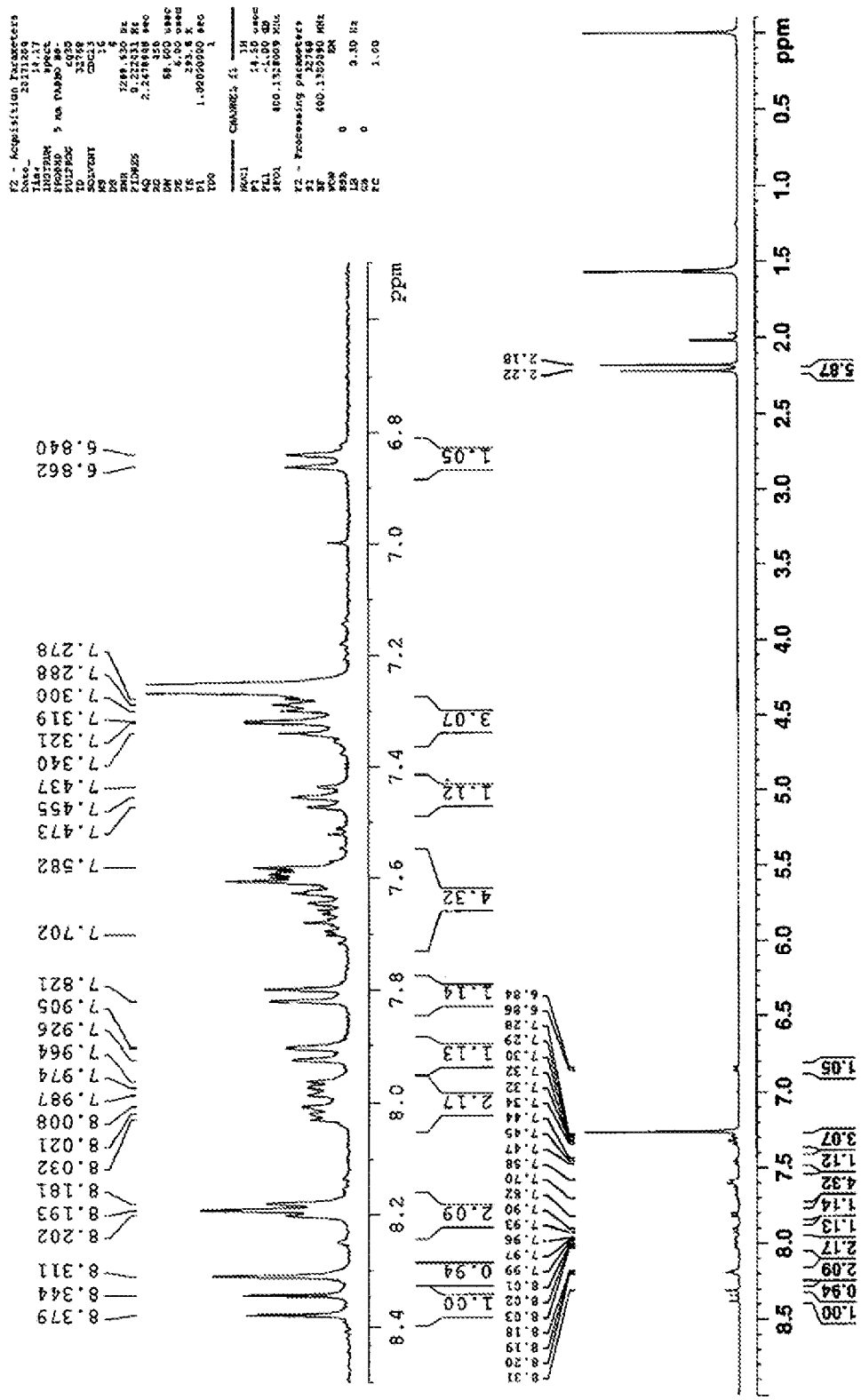
FIG. 7 is a $^1$H•NMR spectrum of a compound (D-4).

$^1$H NMR spectrum (400 MHz, CDCl$_3$) is shown in FIG. 7.

MS(ESI$^+$)m/z: 528.3 ([M+H]$^+$)

<Synthesis of Compound (D-5)>

A compound (D-5) was synthesized according to the following scheme in the same manner as the compound (D-4).

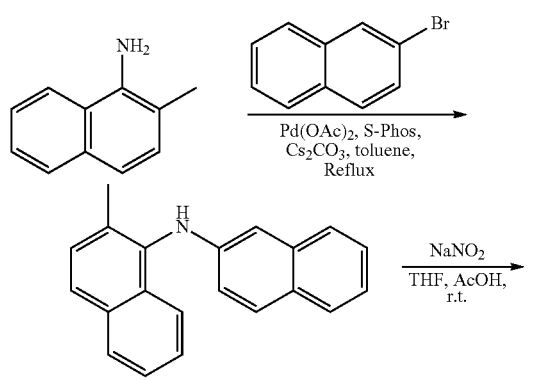

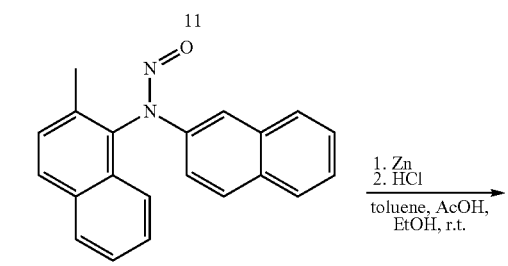

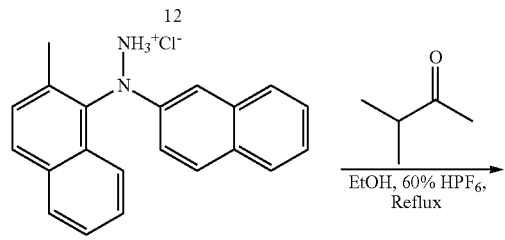

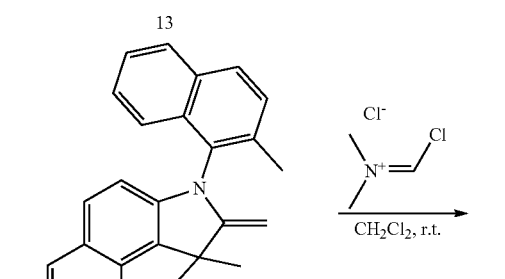

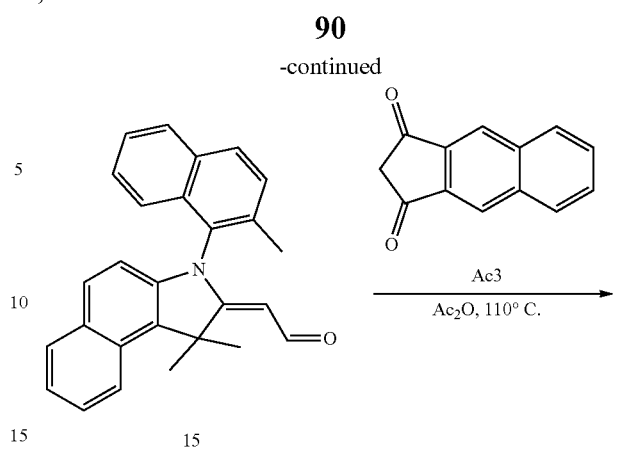

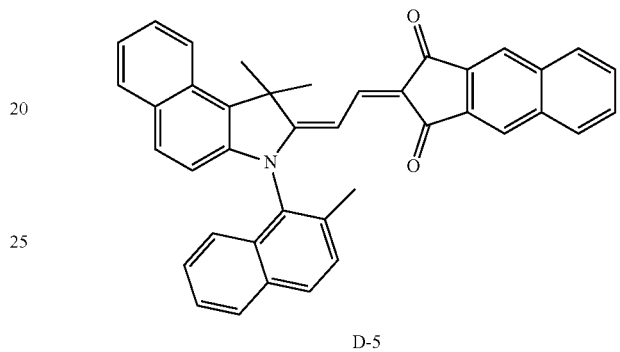

D-5

Figure 8:
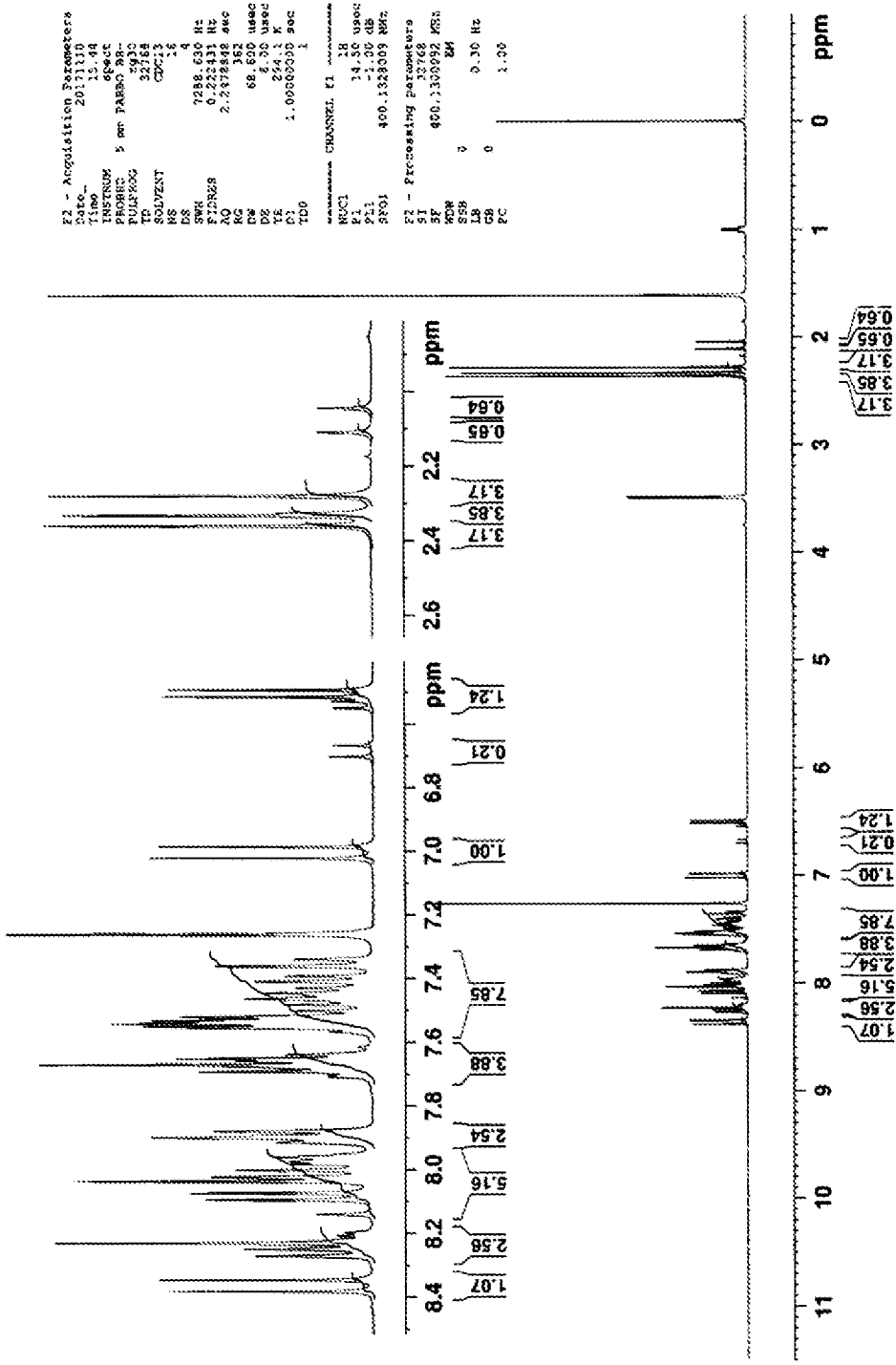
FIG. 8 is a $^1$H•NMR spectrum of a compound (D-5).

$^1$H NMR spectrum (400 MHz, CDCl$_3$) is shown in FIG. 8.

MS(ESI$^+$)m/z: 556.6 ([M+H]$^+$)

<Synthesis of Compound (D-6)>

A compound (D-6) was synthesized according to the following scheme in the same manner as the compound (D-4).

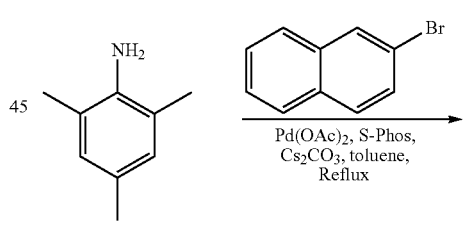

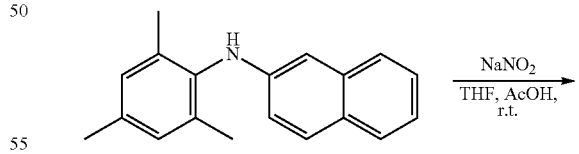

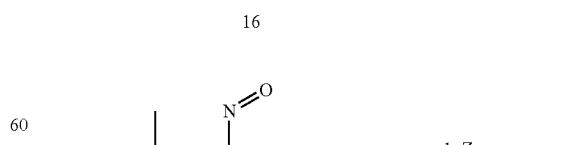

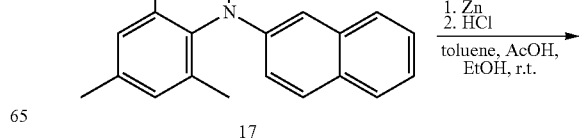

Figure 9:
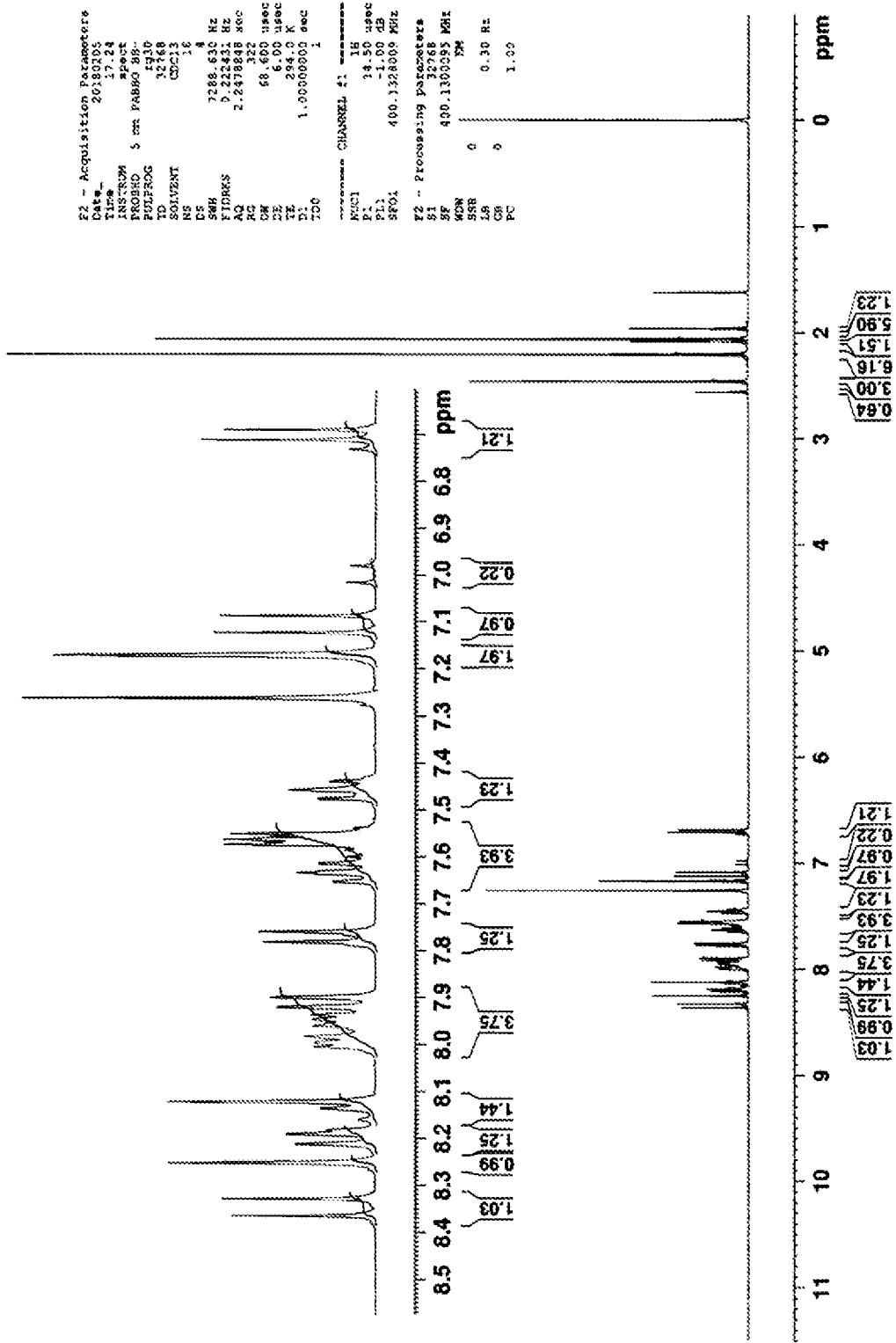
FIG. 9 is a $^1$H•NMR spectrum of a compound (D-6).

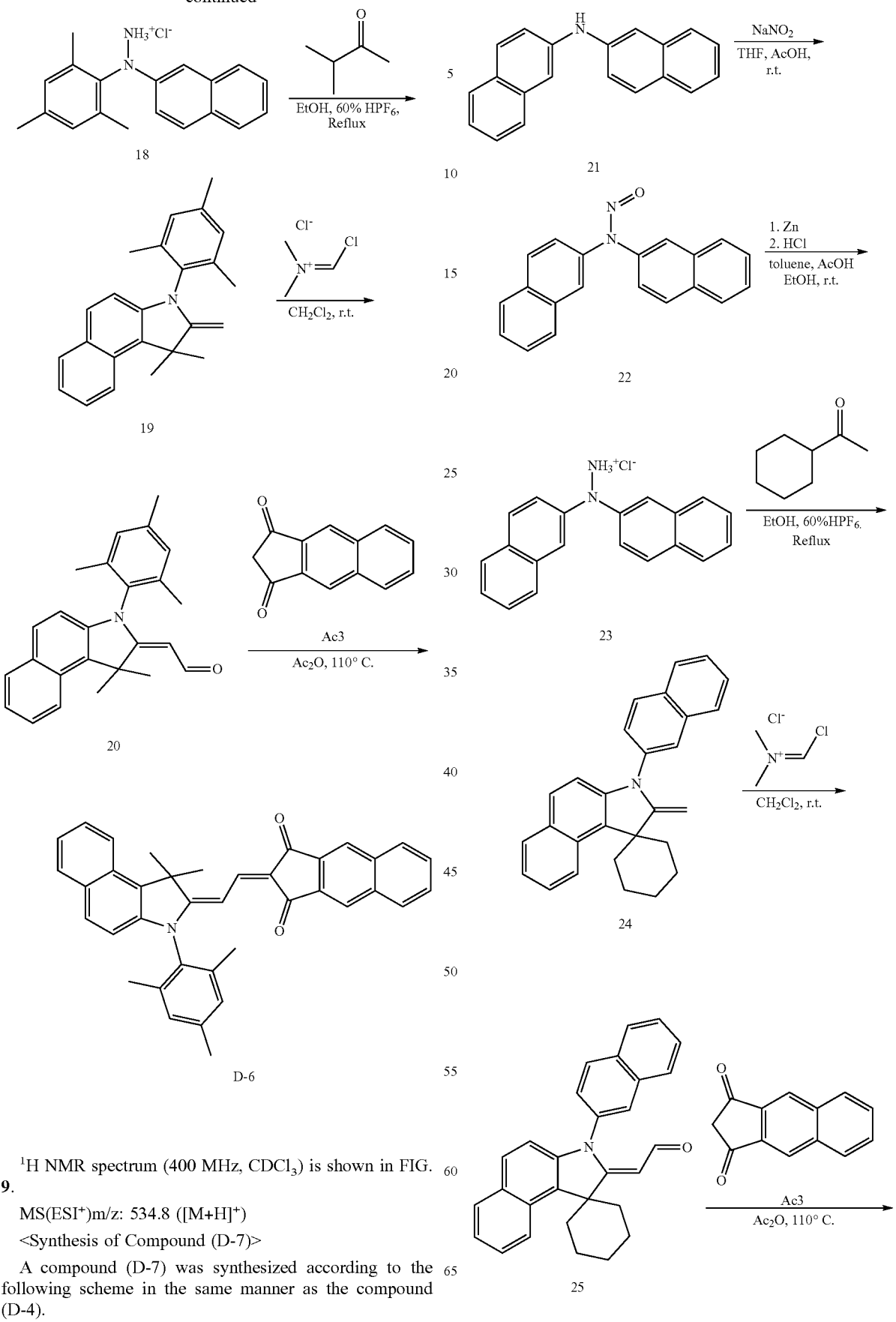
$^1$H NMR spectrum (400 MHz, CDCl$_3$) is shown in FIG. 9.
MS(ESI$^+$)m/z: 534.8 ([M+H]$^+$)
<Synthesis of Compound (D-7)>
A compound (D-7) was synthesized according to the following scheme in the same manner as the compound (D-4).

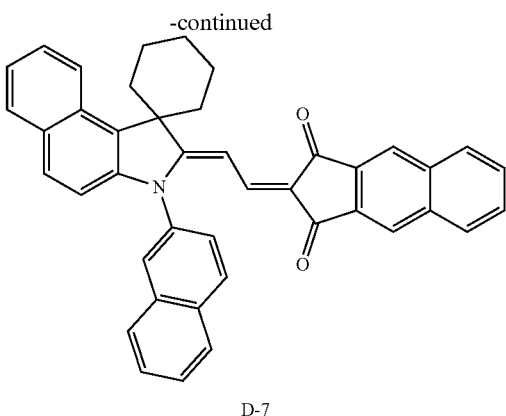

D-7

Figure 10:
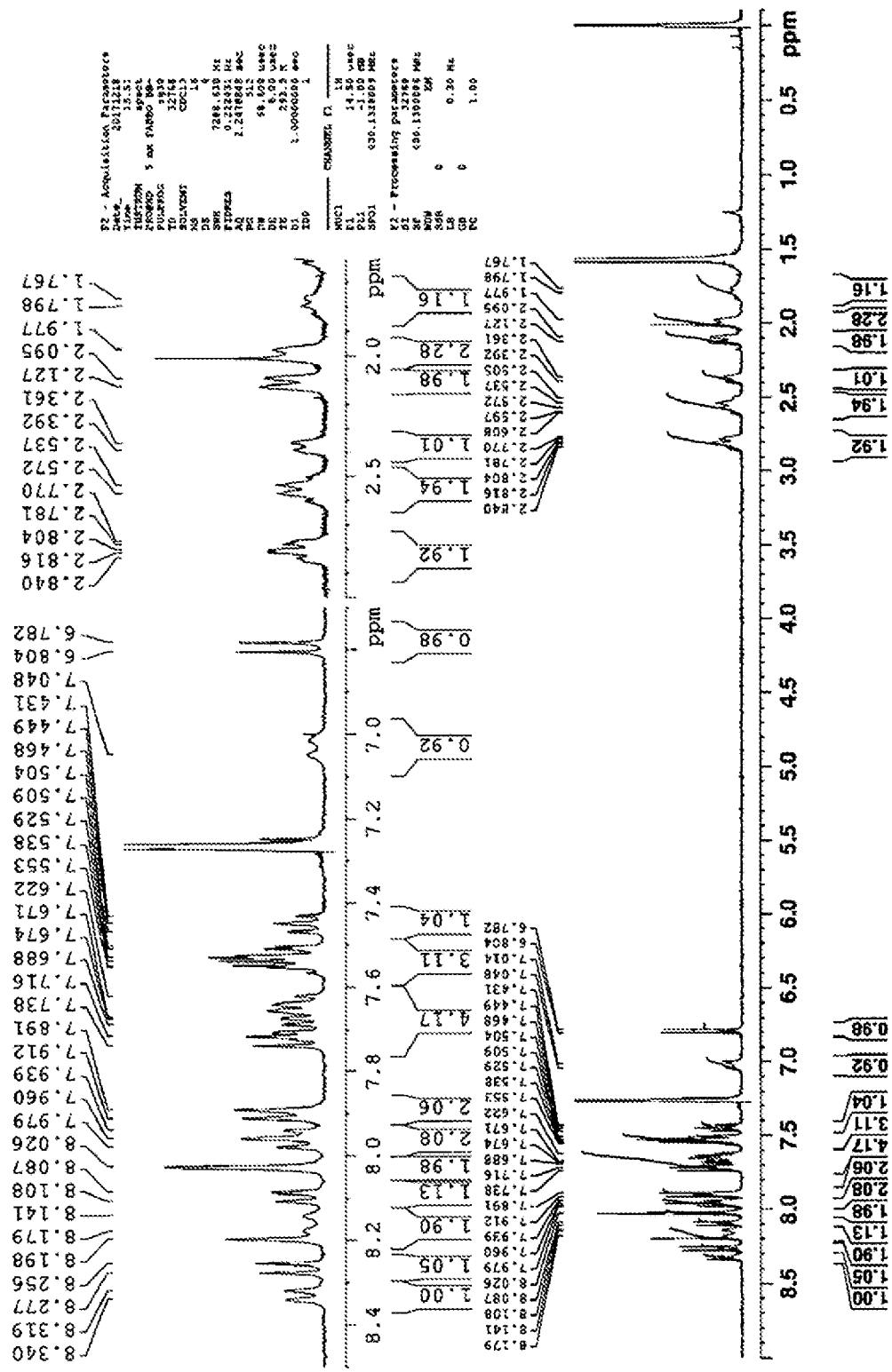
FIG. 10 is a $^1$H•NMR spectrum of a compound (D-7).

$^1$H NMR spectrum (400 MHz, CDCl$_3$) is shown in FIG. 10.

MS(ESI$^+$)m/z: 582.5 ([M+H]$^+$)

<Synthesis of Compound (D-8)>

A compound (D-8) was synthesized according to the following scheme according to the following scheme.

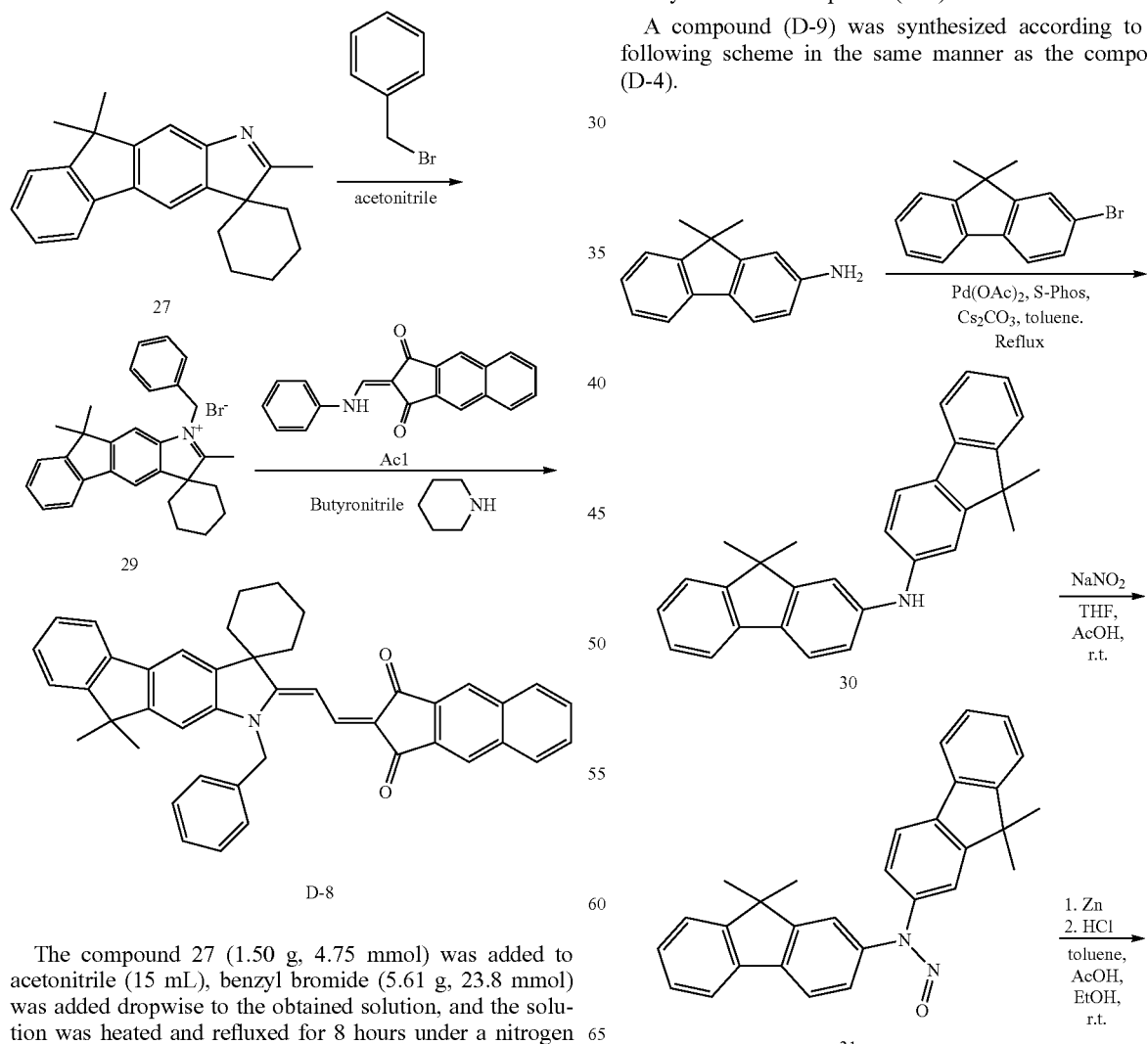

The compound 27 (1.50 g, 4.75 mmol) was added to acetonitrile (15 mL), benzyl bromide (5.61 g, 23.8 mmol) was added dropwise to the obtained solution, and the solution was heated and refluxed for 8 hours under a nitrogen atmosphere. After acetonitrile was removed from the solution by concentration under reduced pressure, toluene was added to separate the solid containing a compound 29 and the toluene solution, and the toluene solution was removed by decantation. MTBE was added to the obtained solid containing the compound 29, dispersion washing was performed, and MTBE was removed by decantation to obtain an orange solid containing the compound 29. The solid was used in the next reaction without further purification.

Figure 11:
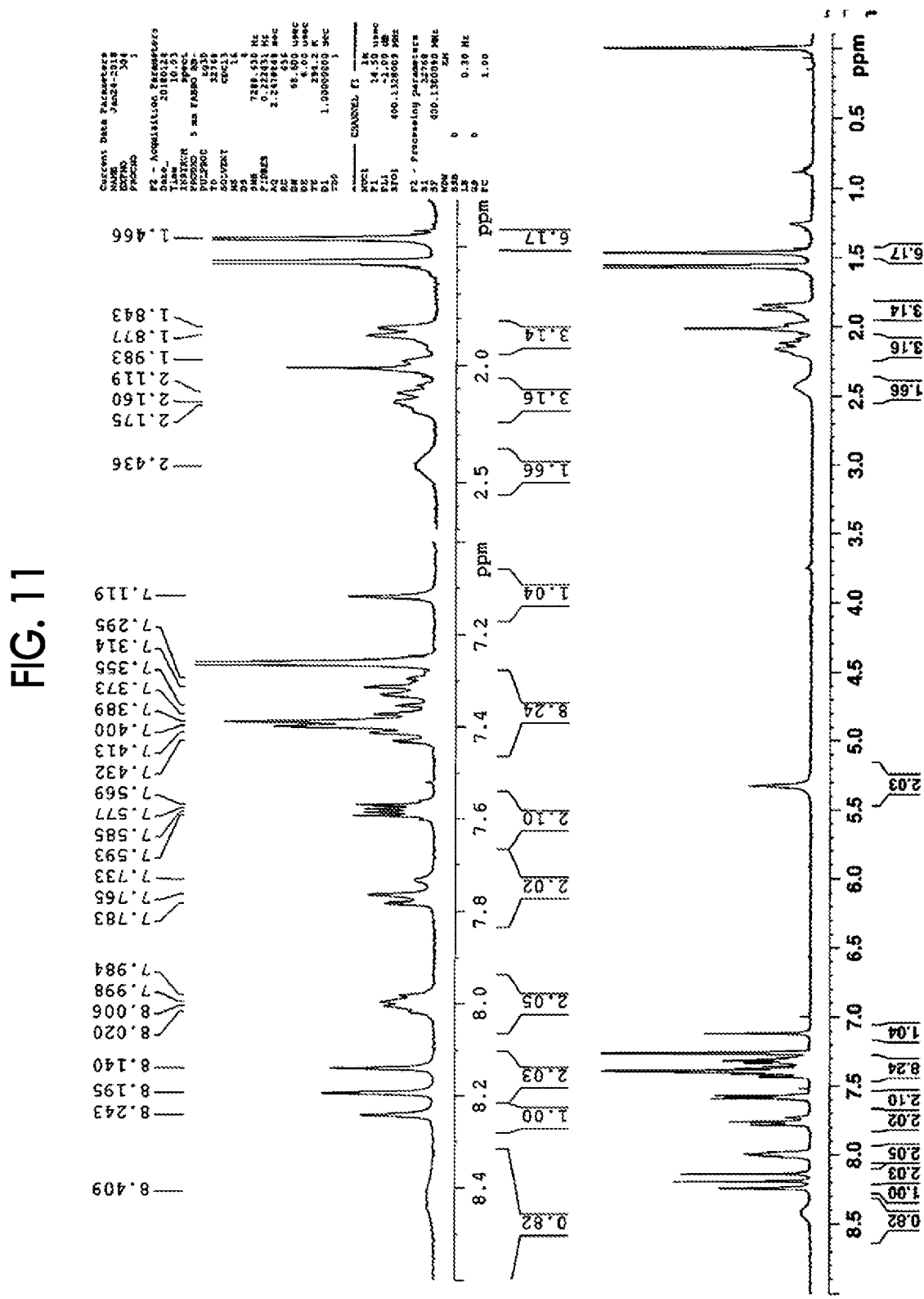
FIG. 11 is a $^1$H•NMR spectrum of a compound (D-8).

The orange solid, Ac1 (1.28 g, 4.28 mmol), and piperidine (1.00 mL) were added to butyronitrile (30 mL), and the obtained solution was heated and refluxed for 48 hours under a nitrogen atmosphere. The obtained solution was cooled to room temperature, the precipitated solid was collected by filtration, and the collected solid was washed with acetonitrile to obtain a crude product. The obtained crude product was purified by silica gel column chromatography (chloroform:ethyl acetate=9:1), and the obtained compound was recrystallized from a chloroform-acetonitrile mixed solvent and washed with acetonitrile to obtain a compound (D-8) (710 mg, 1.16 mmol, yield 24% (two steps)). $^1$H-NMR spectrum (400 MHz, CDCl$_3$) is shown in FIG. 11.

MS(ESI$^+$)m/z: 512.9 ([M+H]$^+$)

<Synthesis of Compound (D-9)>

A compound (D-9) was synthesized according to the following scheme in the same manner as the compound (D-4).

Figure 12:
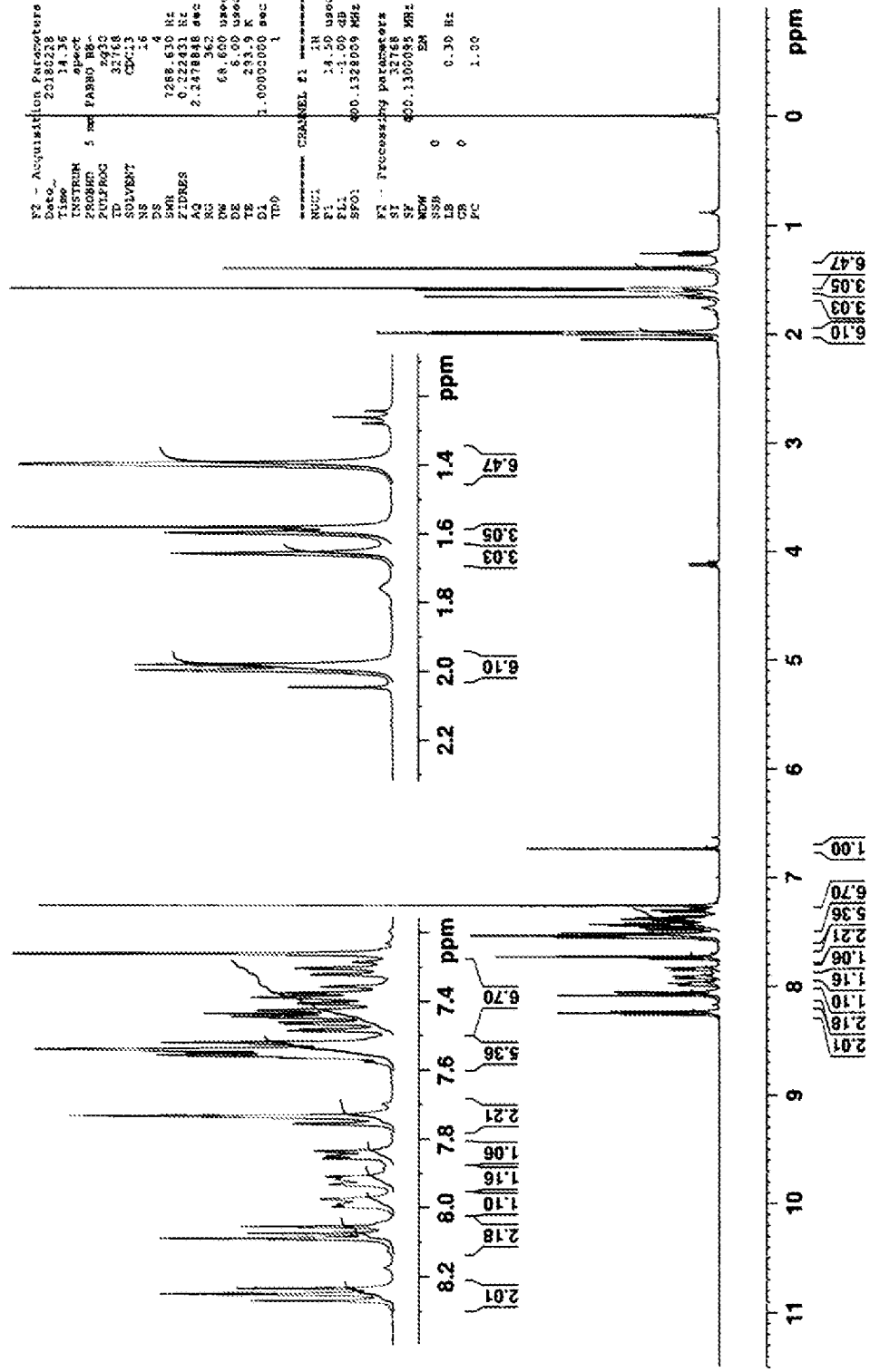
FIG. 12 is a $^1$H•NMR spectrum of a compound (D-9).

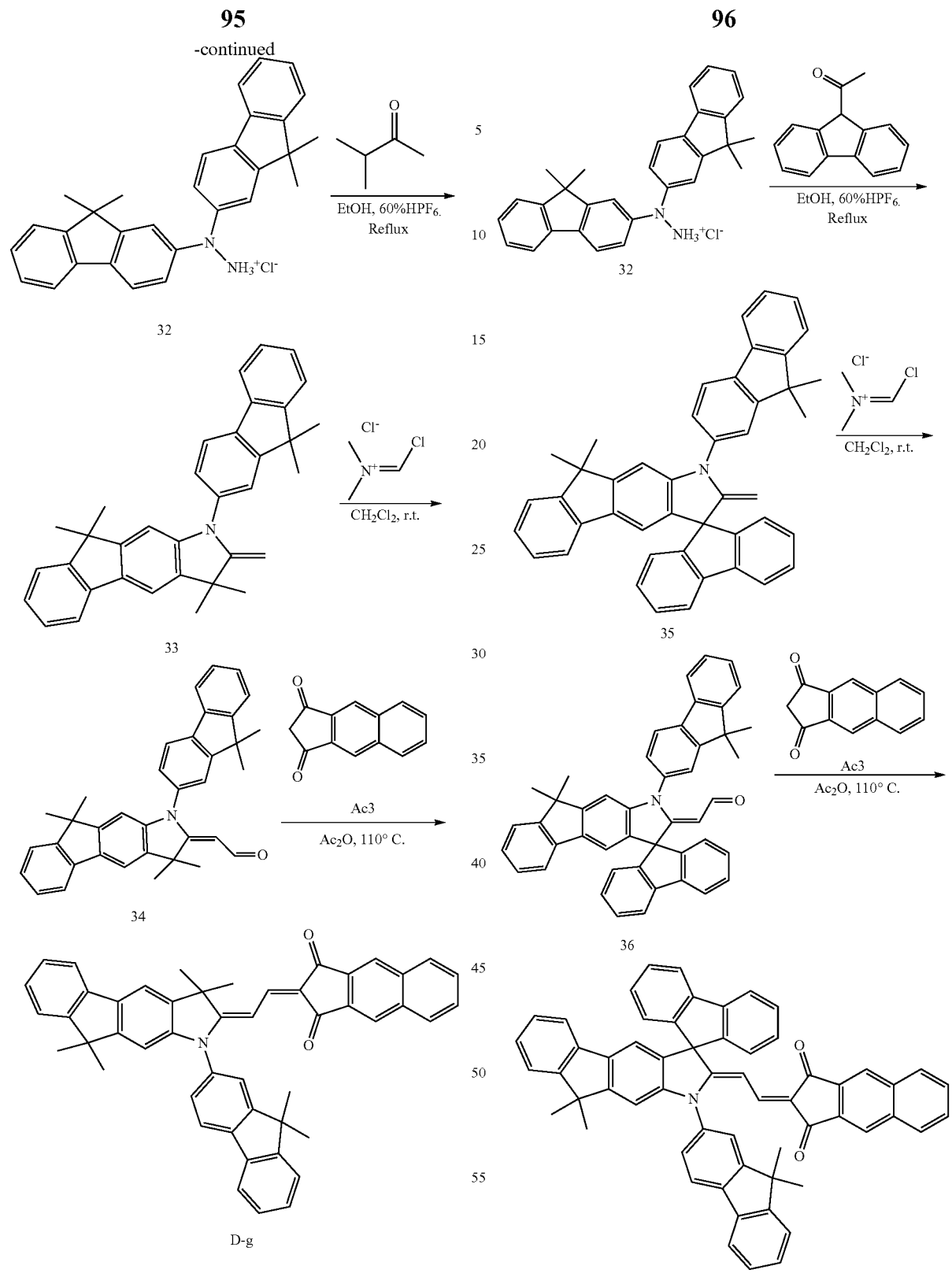
$^1$H NMR spectrum (400 MHz, CDCl$_3$) is shown in FIG. 12.
MS(ESI$^+$)m/z: 534.8 ([M+H]$^+$)
<Synthesis of Compound (D-10)>
A compound (D-10) was synthesized according to the following scheme with reference to the synthesis of the compound (D-4).
MS(ESI$^+$)m/z: 795.8 ([M+H]$^+$)
<Synthesis of Compound (D-11)>
A compound (D-11) was synthesized according to the following scheme.

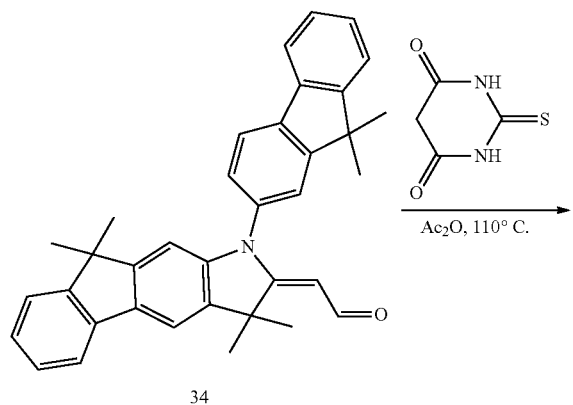

34

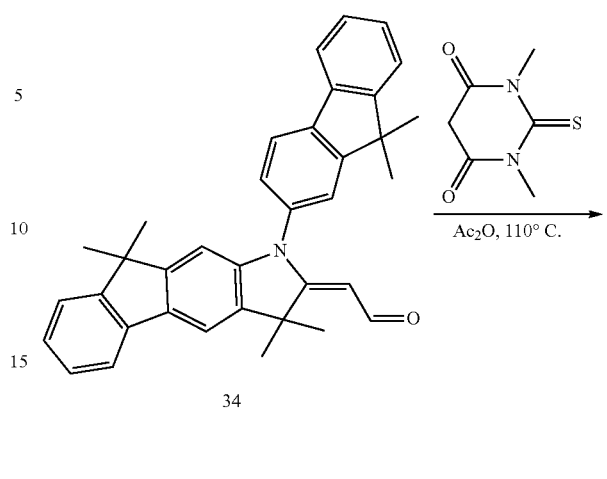

34

D-11

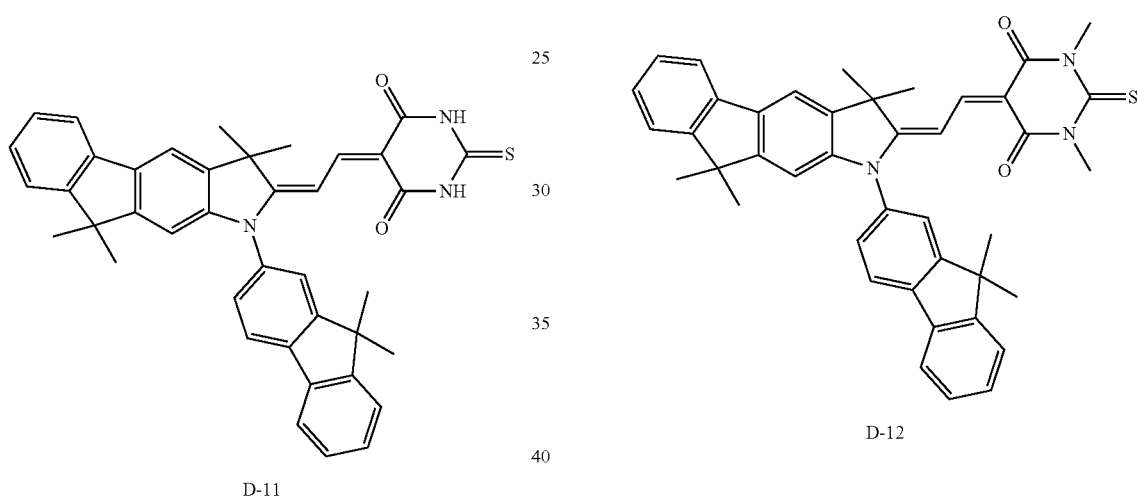

D-12

A compound 34 (480 mg, 0.968 mmol) and 2-thiobarbituric acid (140 mg, 0.968 mmol) were added to acetic anhydride (7 mL), and the obtained solution was reacted at 110° C. for 2 hours under a nitrogen atmosphere. After the obtained solution was cooled to room temperature and the solvent was removed by concentration under reduced pressure, the obtained crude product was purified by silica gel column chromatography (chloroform:ethyl acetate=9:1), and the obtained compound was recrystallized from a chloroform-acetonitrile mixed solvent and washed with acetonitrile to obtain a compound (D-11) (283 mg, 0.455 mmol, yield 47%).

Figure 13:
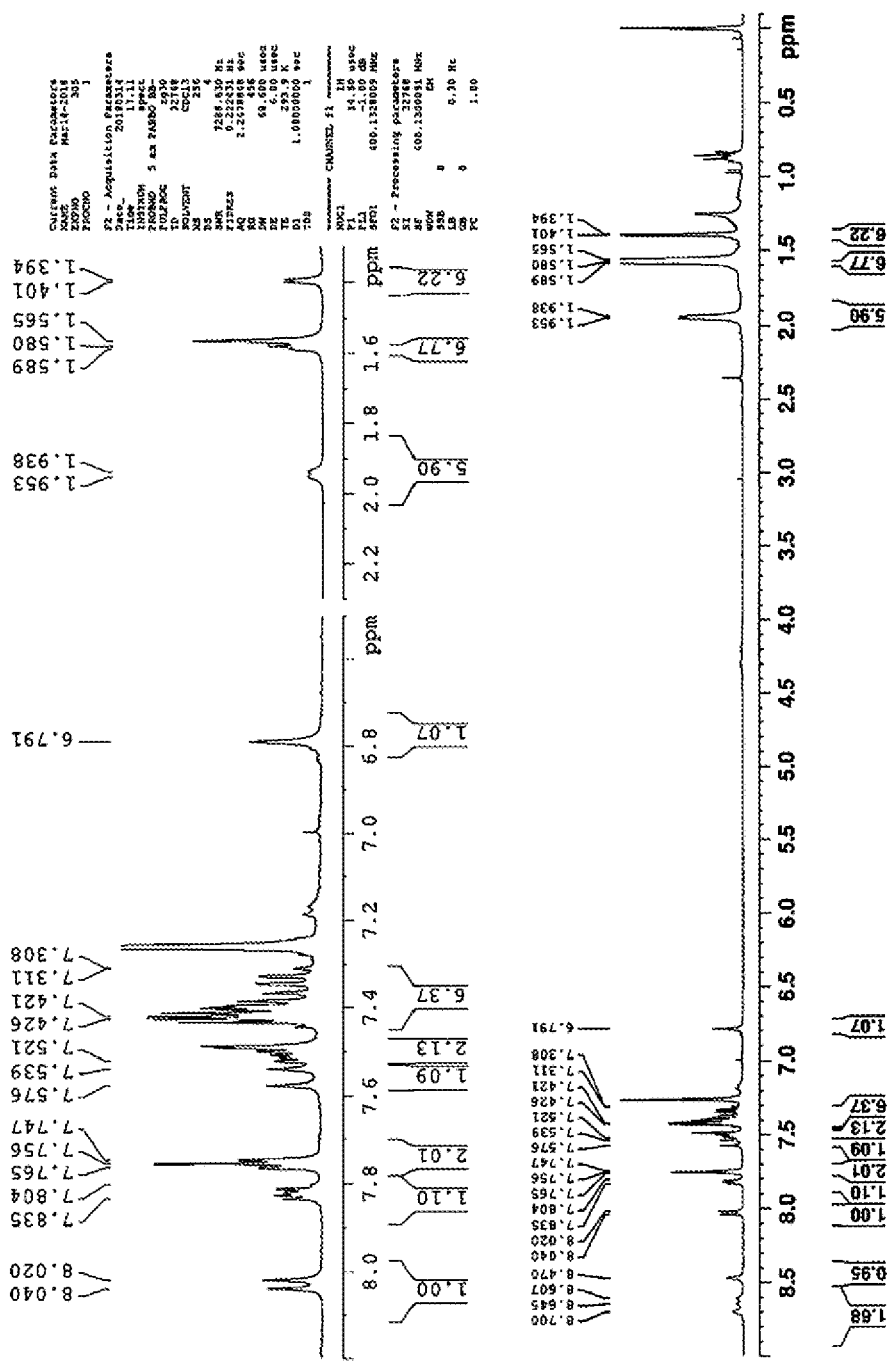
FIG. 13 is a $^1$H•NMR spectrum of a compound (D-11).

$^1$H NMR spectrum (400 MHz, DMSO) is shown in FIG. 13.

MS(ESI$^+$)m/z: 622.5 ([M+H]$^+$)

<Synthesis of Compound (D-12)>

A compound (D-12) was synthesized according to the following scheme with reference to the synthesis of the compound (D-11).

MS(ESI$^+$)m/z: 650.6 ([M+H]$^+$)

<Synthesis of Compound (D-13)>

A compound (D-13) was synthesized according to the following scheme with reference to the synthesis of the compounds (D-11) and (D-12).

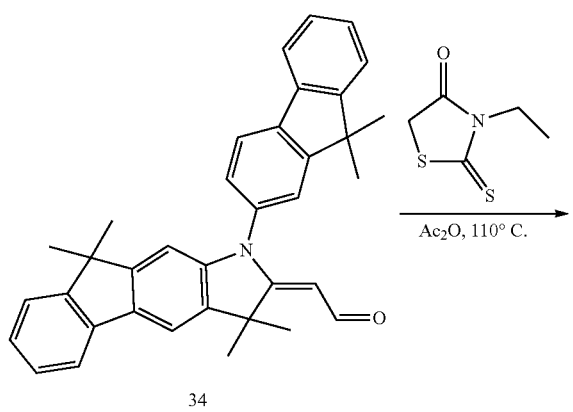

34

-continued

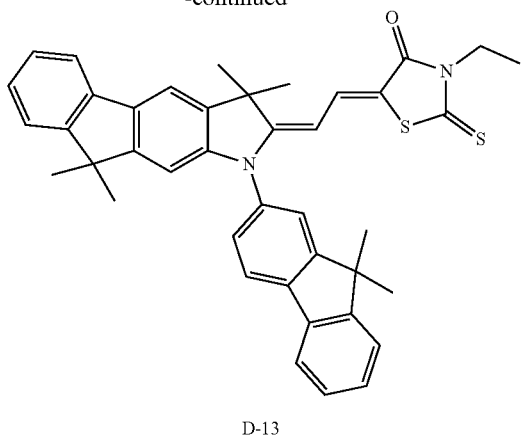

D-13

MS(ESI⁺)m/z: 639.7 ([M+H]⁺)
<Synthesis of Compound (D-14)>
A compound (D-14) was synthesized according to the following scheme.

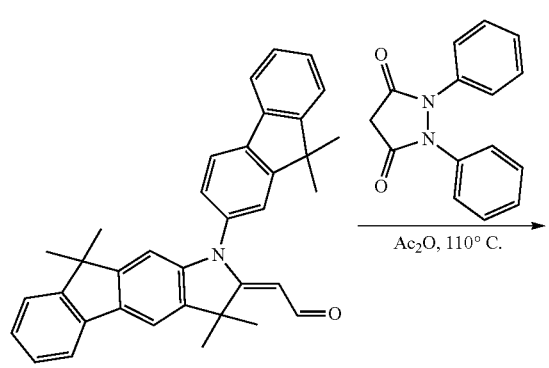

D-14

A compound 34 (480 mg, 0.968 mmol), 1,2-diphenylpyrazolidine-3,5-dione (244 mg, 0.968 mmol) were added to acetic anhydride (7 mL), and the obtained solution was reacted at 110° C. for 2 hours under a nitrogen atmosphere. After the obtained solution was cooled to room temperature and the solvent was removed by concentration under reduced pressure, the obtained crude product was purified by silica gel column chromatography (chloroform: ethyl acetate=9:1), and the obtained compound was recrystallized from a chloroform-acetonitrile mixed solvent and washed with acetonitrile to obtain a compound (D-14) (311 mg, 0.426 mmol, yield 44%).

Figure 14:
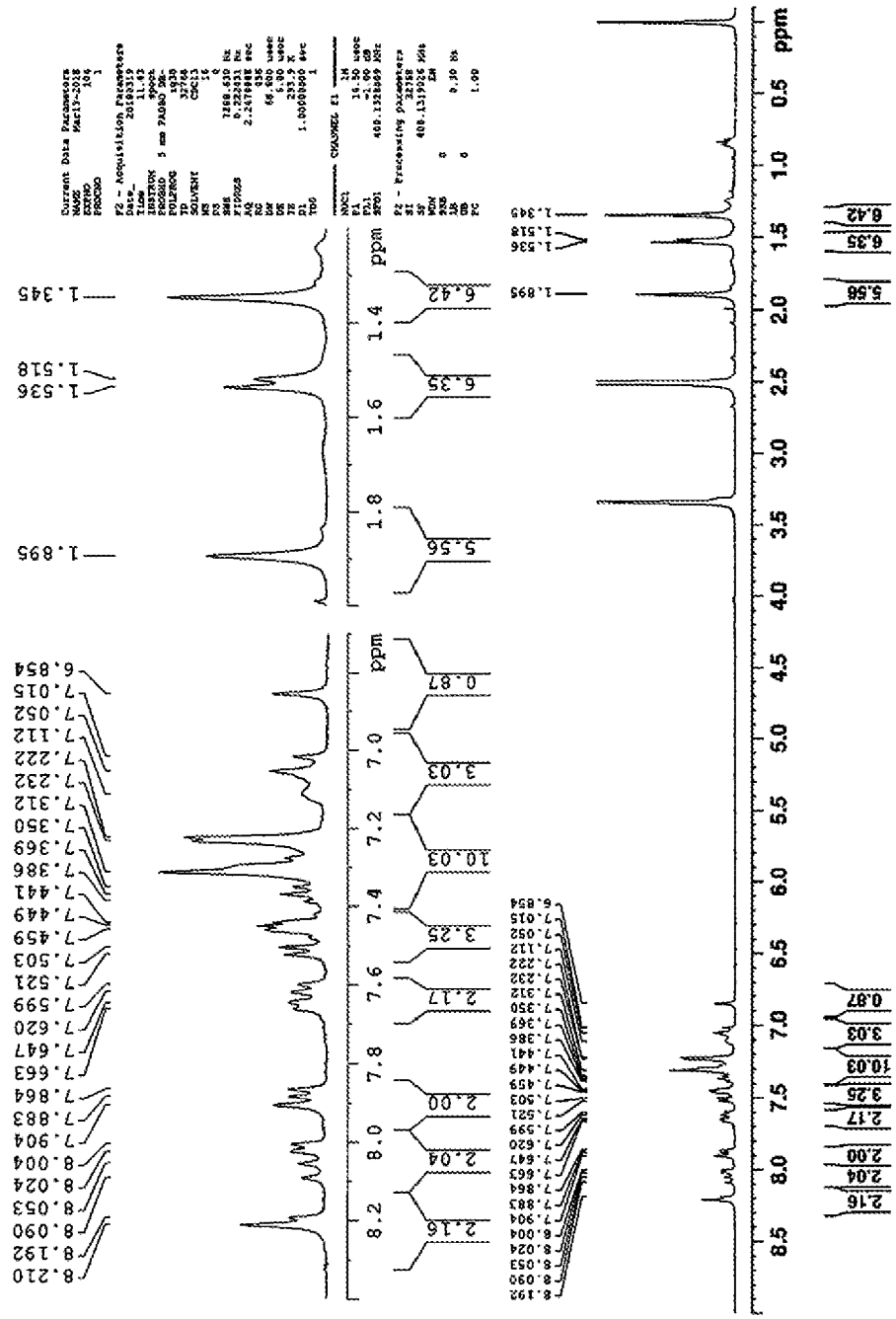
FIG. 14 is a $^1$H•NMR spectrum of a compound (D-14).

¹H NMR spectrum (400 MHz, DMSO) is shown in FIG. 14.

MS(ESI⁺)m/z: 730.0 ([M+H]⁺)
<Synthesis of Compound (D-15)>
A compound (D-15) was synthesized according to the following scheme with reference to the synthesis of the compounds (D-2) and (D-11).

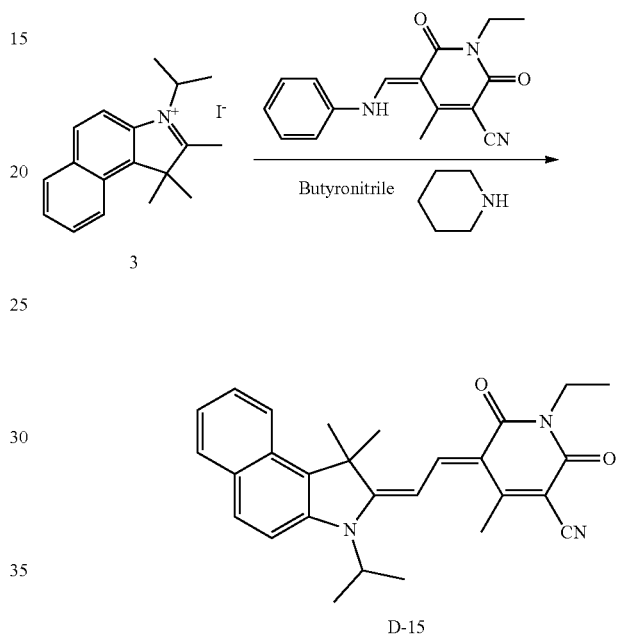

D-15

MS(ESI⁺)m/z: 428.4 ([M+H]⁺)
<Synthesis of Compound (D-16)>
A compound (D-16) was synthesized according to the following scheme with reference to the synthesis of the compound (D-2).

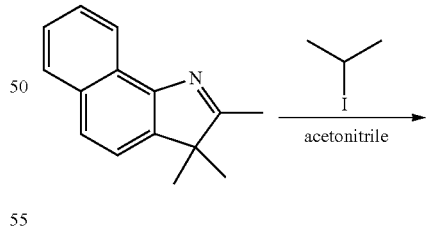

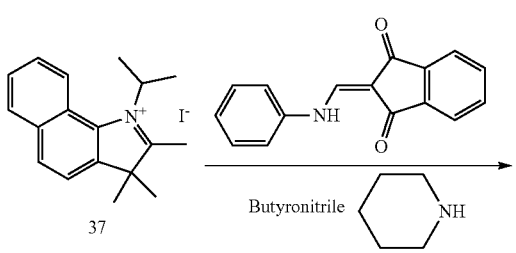

Figure 15:
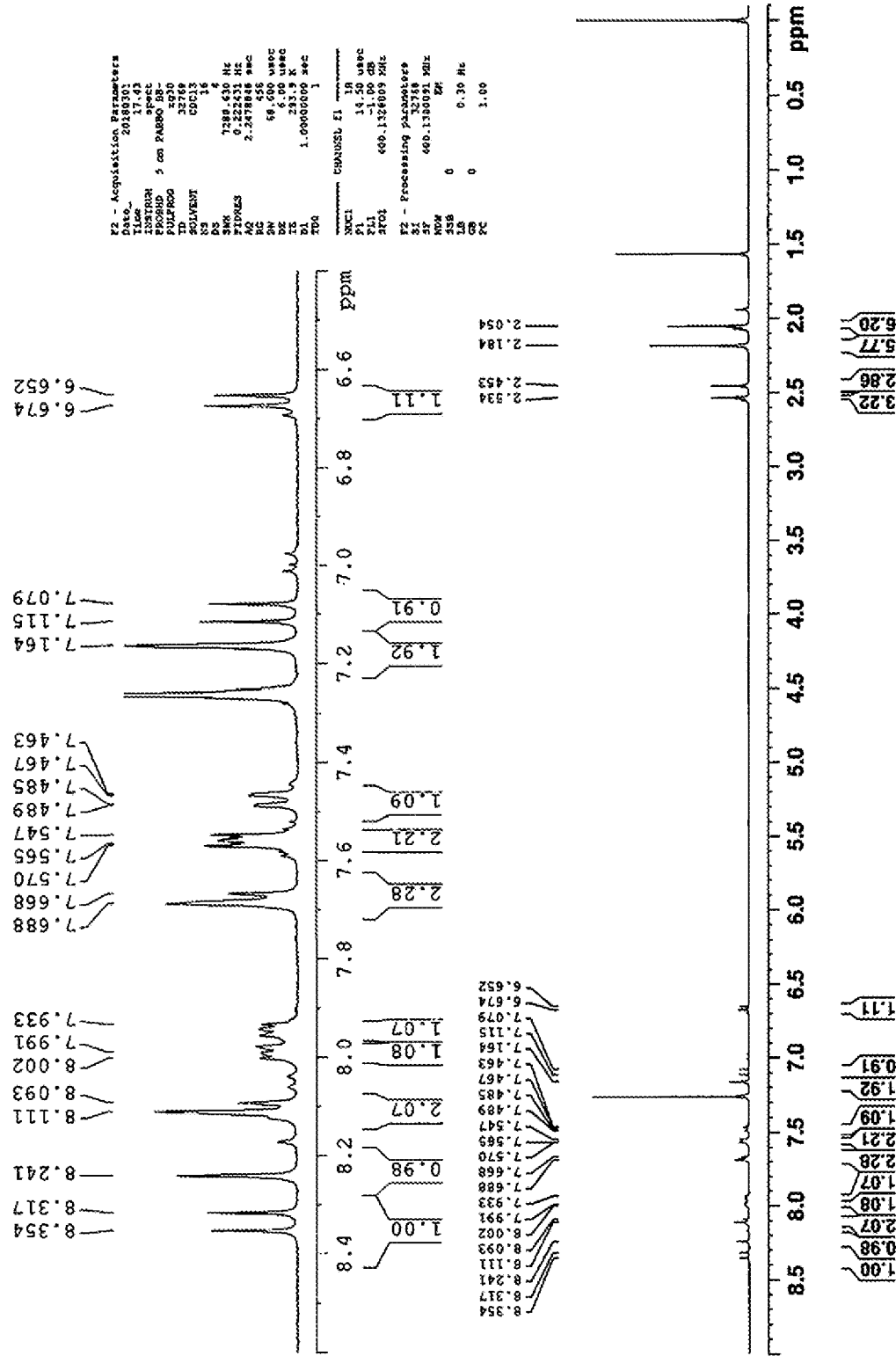
FIG. 15 is a $^1$H•NMR spectrum of a compound (D-17).

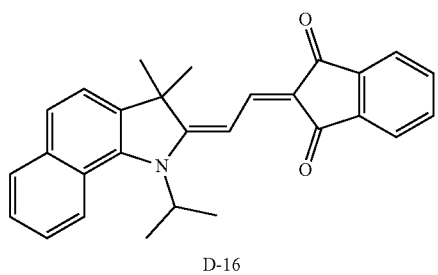
D-16
MS(ESI⁺)m/z: 408.2 ([M+H]⁺)
<Synthesis of Compound (D-17)>
A compound (D-17) was synthesized according to the following scheme in the same manner as the synthesis of the compound (D-6).
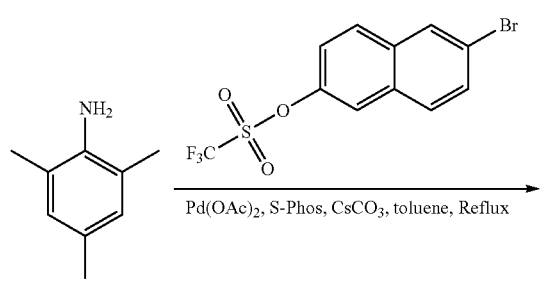
38
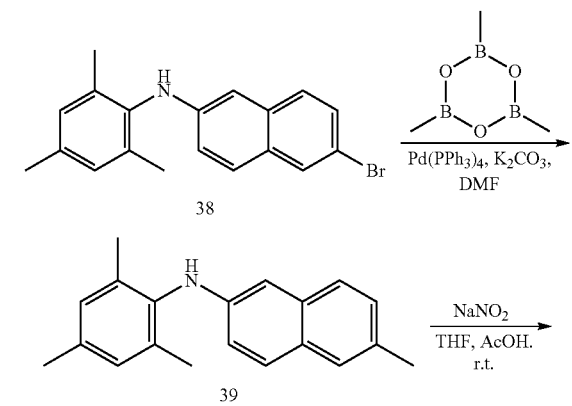
39
40
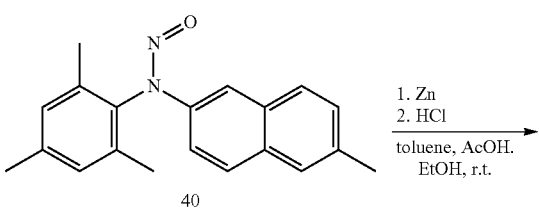
41
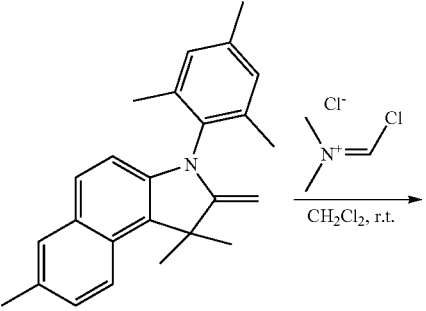
42
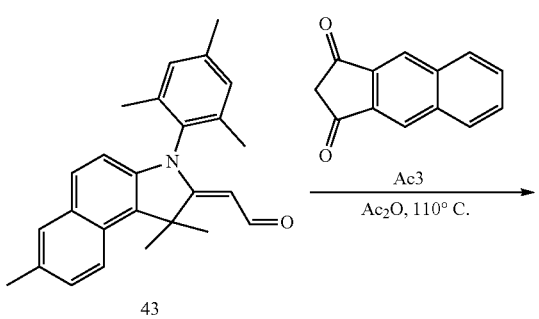
43
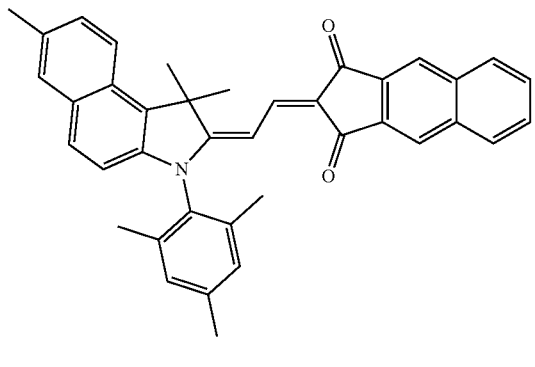
D-17
¹H NMR spectrum (400 MHz, CDCl₃) is shown in FIG. 15.
MS(ESI⁺)m/z: 545.8 ([M+H]⁺)
<Synthesis of Compound (D-18)>
A compound (D-18) was synthesized according to the following scheme with reference to the synthesis of the compounds (D-6) and (D-3).
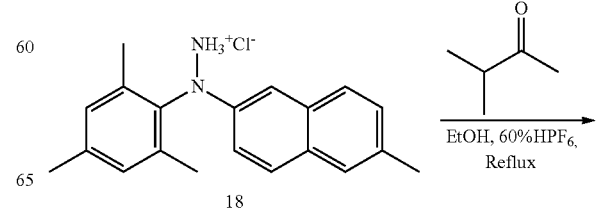
18

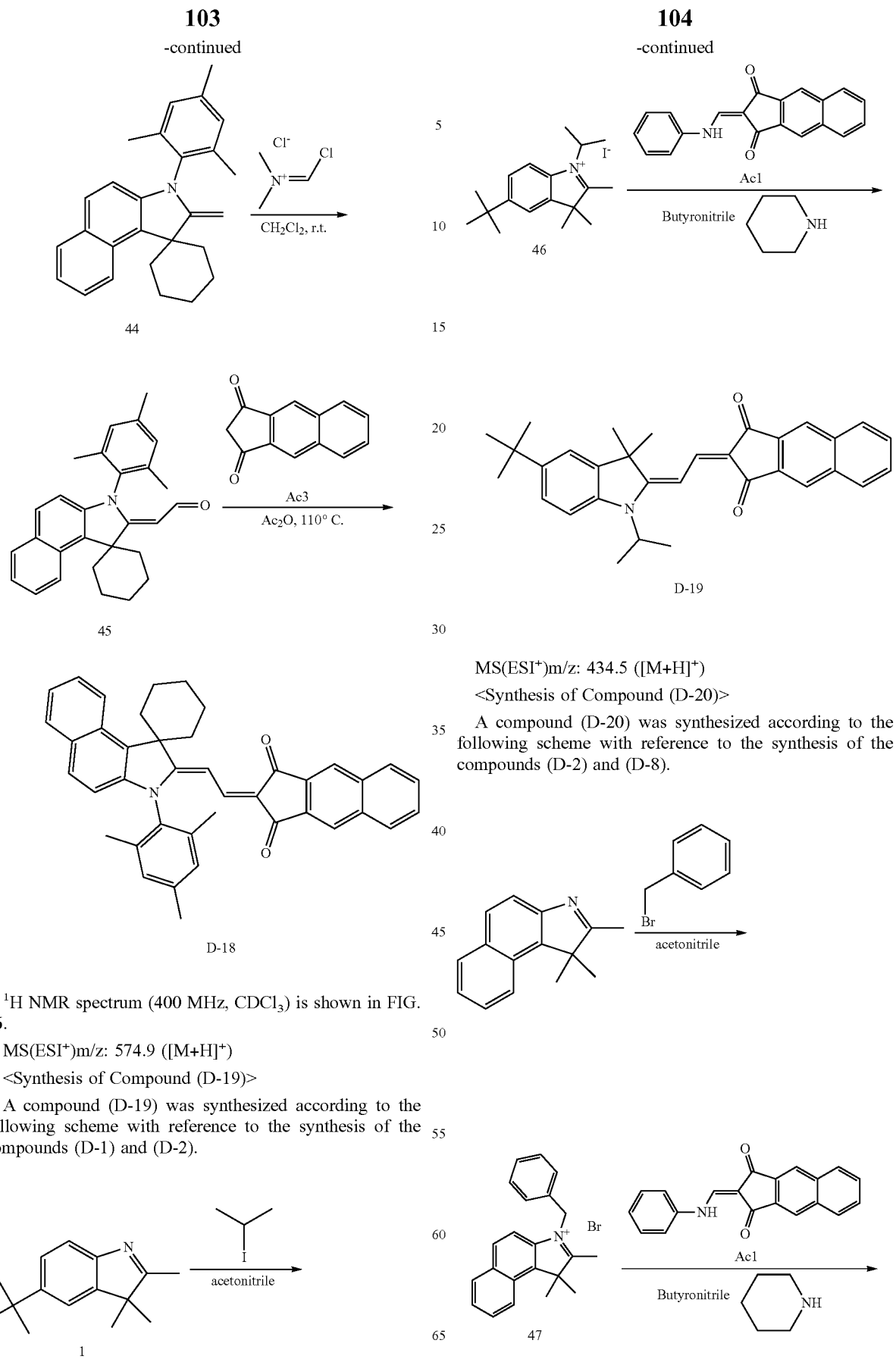

Figure 16:
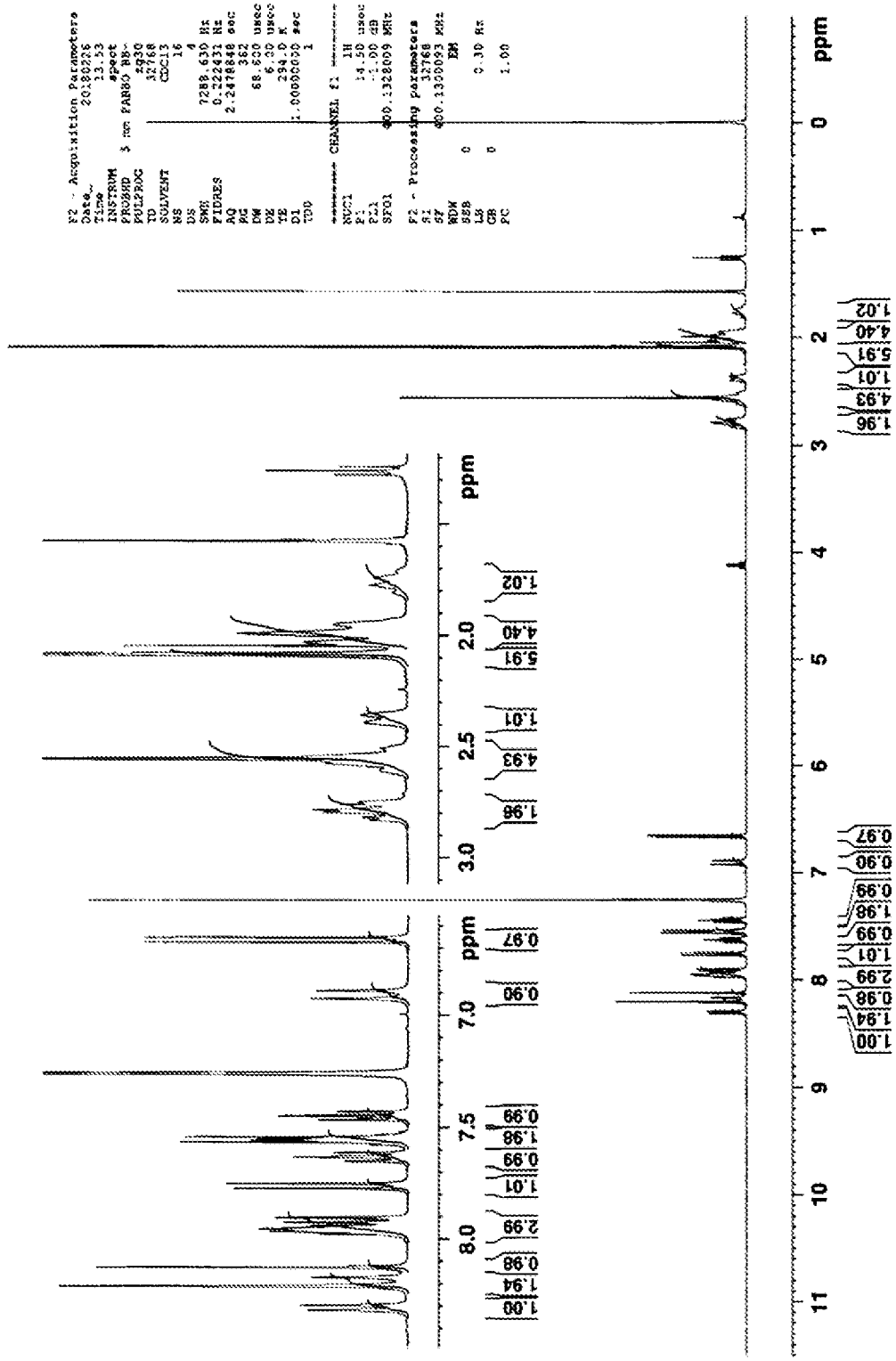
FIG. 16 is a $^1$H•NMR spectrum of a compound (D-18).

$^1$H NMR spectrum (400 MHz, CDCl$_3$) is shown in FIG. 16.

MS(ESI$^+$)m/z: 574.9 ([M+H]$^+$)

<Synthesis of Compound (D-19)>

A compound (D-19) was synthesized according to the following scheme with reference to the synthesis of the compounds (D-1) and (D-2).

MS(ESI$^+$)m/z: 434.5 ([M+H]$^+$)

<Synthesis of Compound (D-20)>

A compound (D-20) was synthesized according to the following scheme with reference to the synthesis of the compounds (D-2) and (D-8).

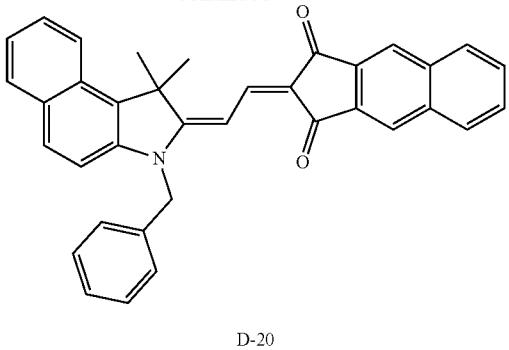

D-20

MS(ESI+)m/z: 505.6 ([M+H]+)

<Synthesis of Compound (D-21)>

A compound (D-21) was synthesized according to the following scheme.

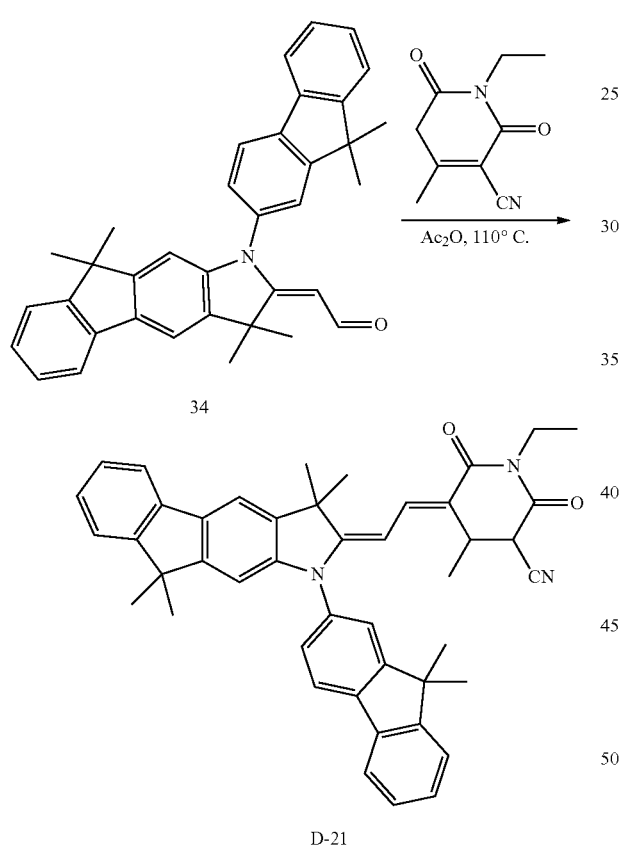

D-21

A compound 34 (480 mg, 0.968 mmol), 3-cyano-1-ethyl-6-hydroxy-4-methyl-2-pyridone (172 mg, 0.968 mmol) were added to acetic anhydride (7 mL), and the obtained solution was reacted at 110° C. for 2 hours under a nitrogen atmosphere. After the obtained solution was cooled to room temperature and the solvent was removed by concentration under reduced pressure, the obtained crude product was purified by silica gel column chromatography (chloroform: ethyl acetate=9:1), and the obtained compound was recrystallized from a chloroform-acetonitrile mixed solvent and washed with acetonitrile to obtain a compound (D-21) (456 mg, 0.695 mmol, yield 72%).

Figure 17:
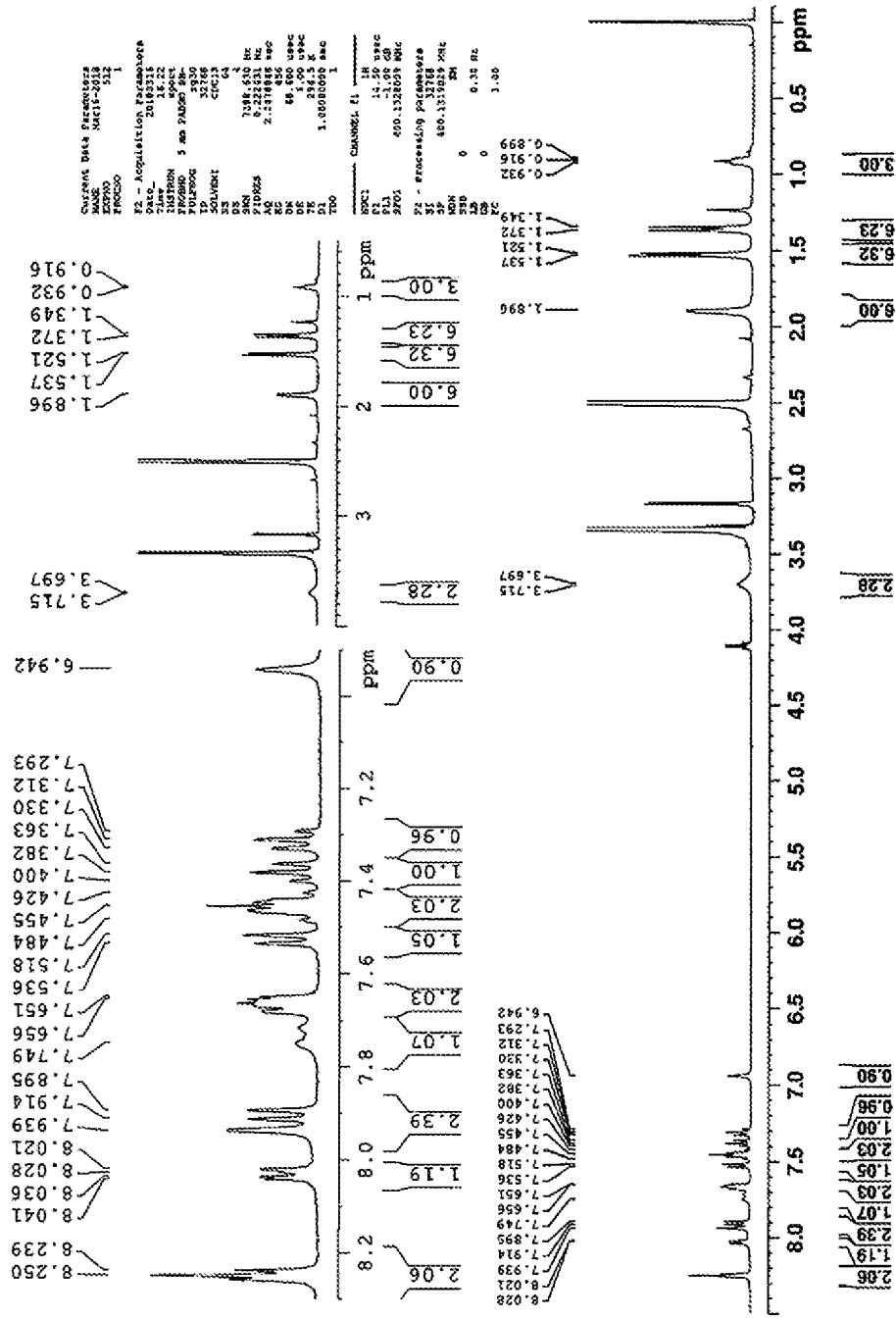
FIG. 17 is a $^1$H•NMR spectrum of a compound (D-21).
Figure 18:
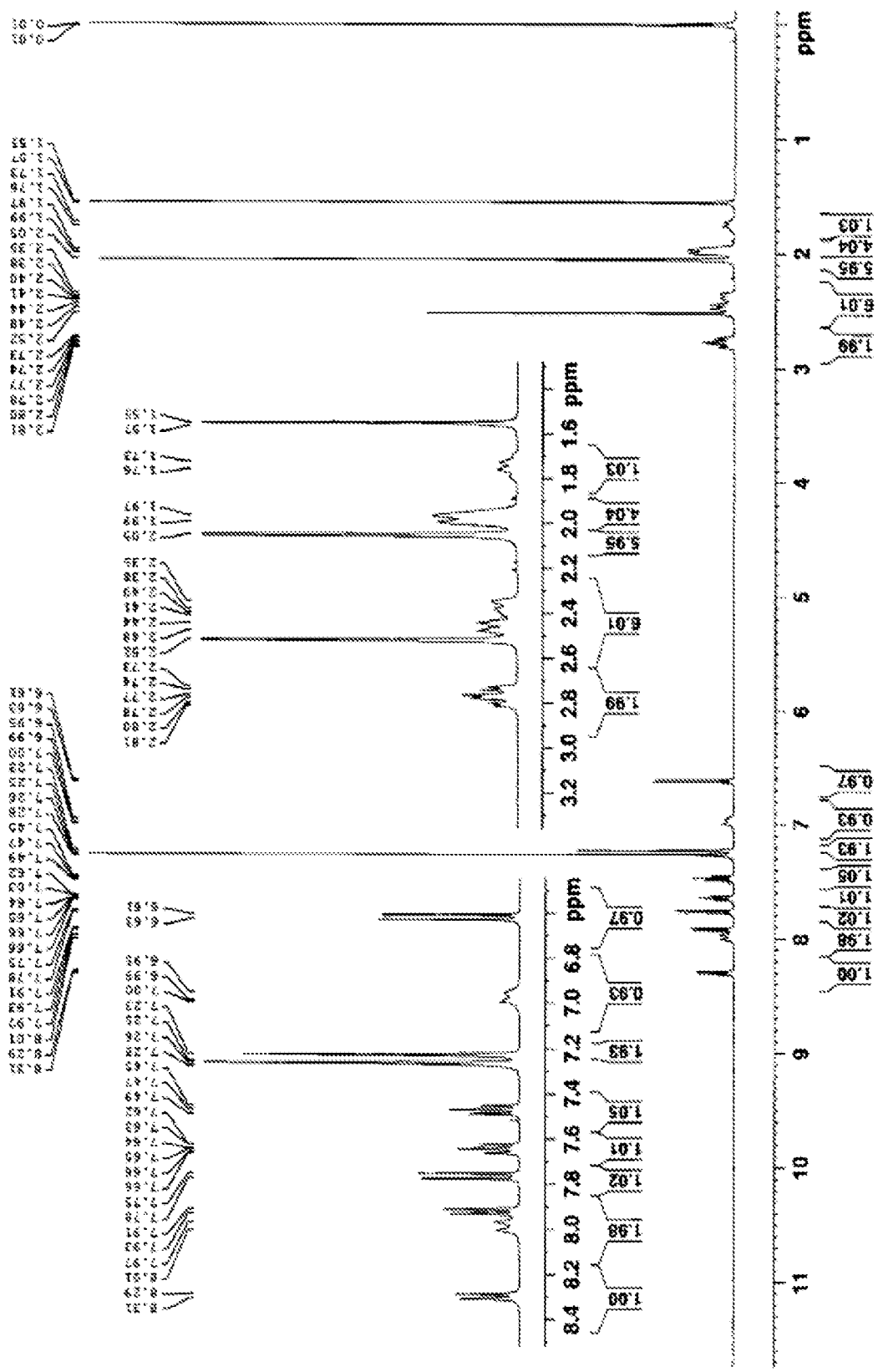
FIG. 18 is a $^1$H•NMR spectrum of a compound (D-22).
Figure 19:
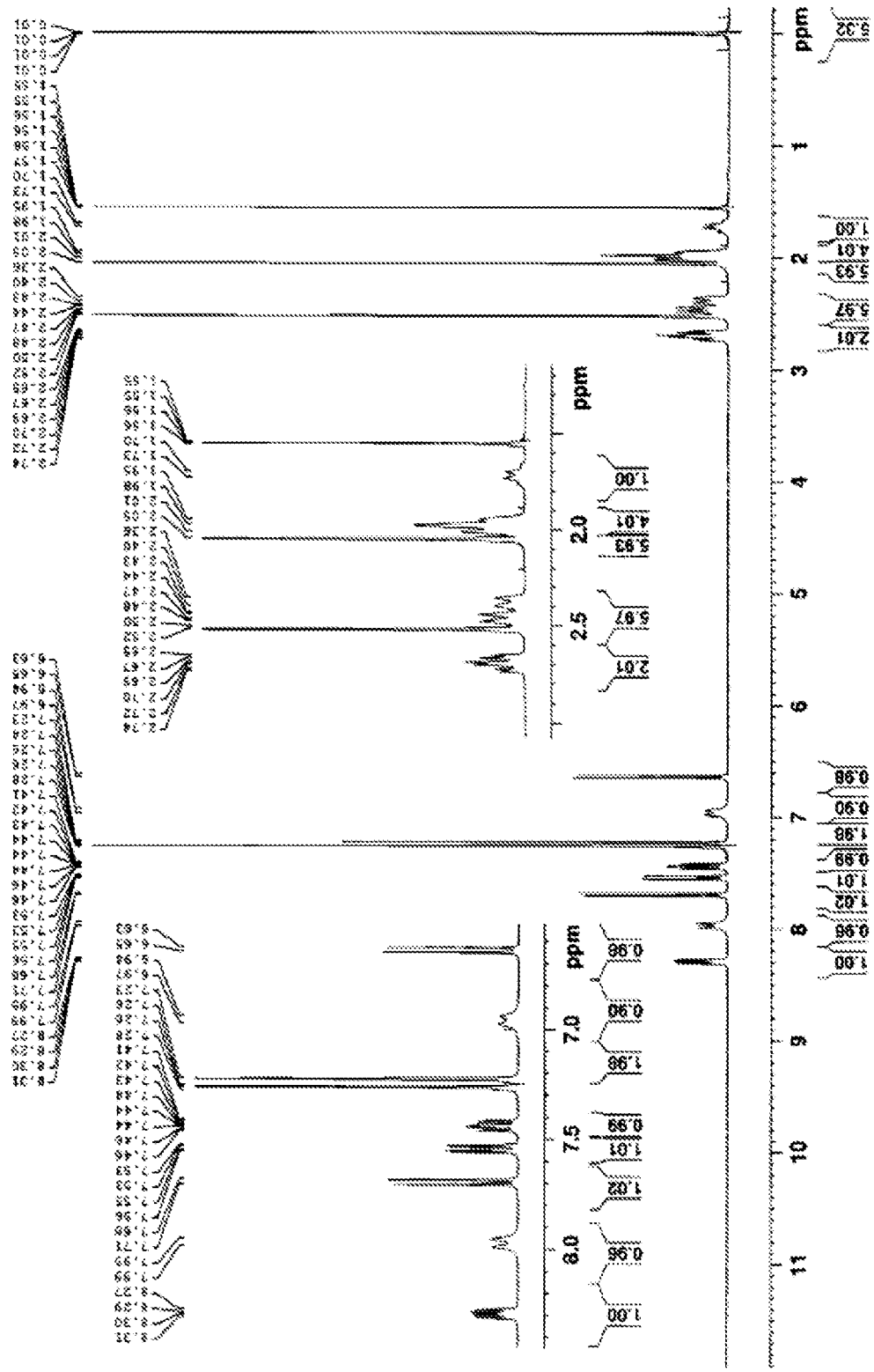
FIG. 19 is a $^1$H•NMR spectrum of a compound (D-24).
Figure 20:
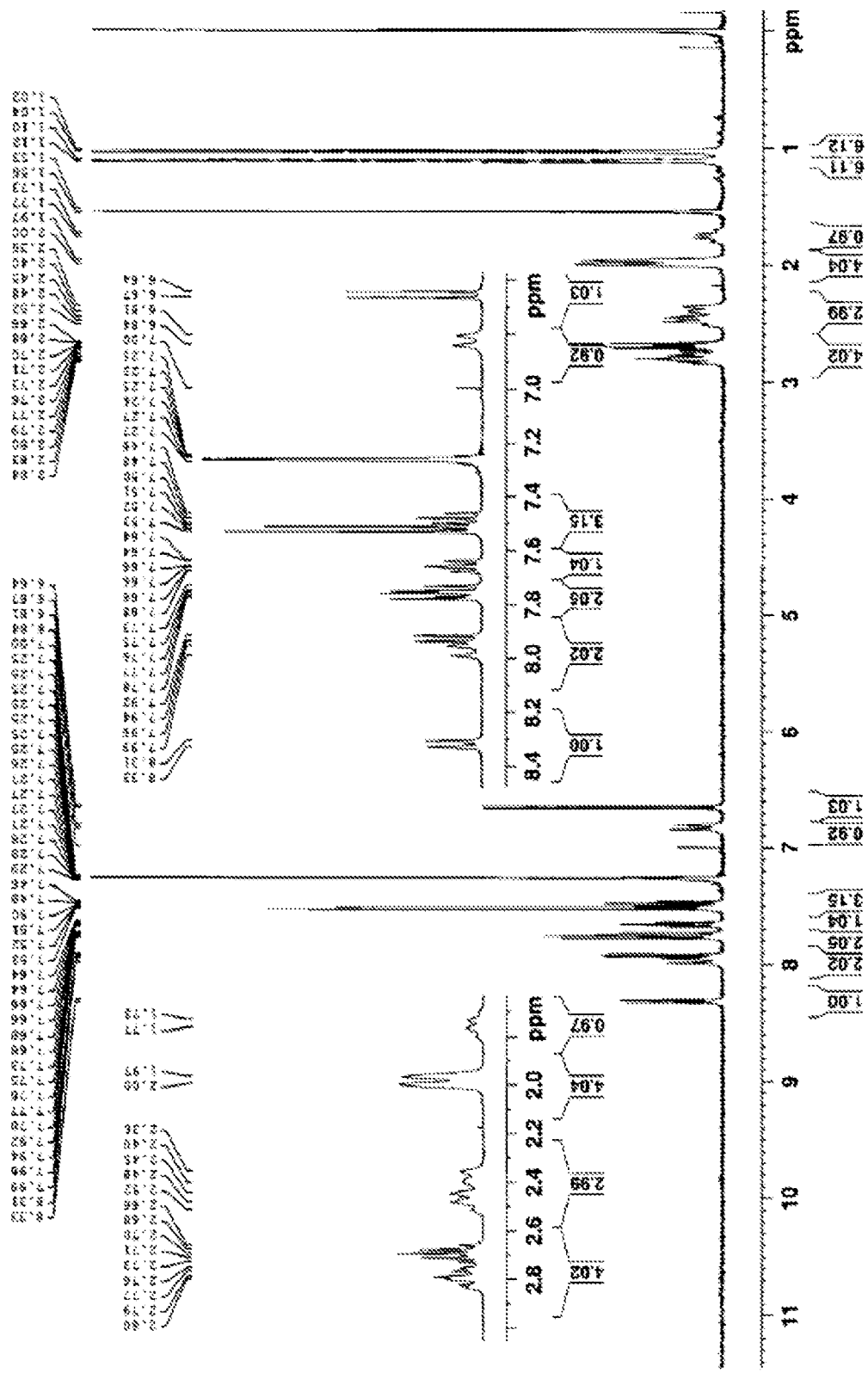
FIG. 20 is a $^1$H•NMR spectrum of a compound (D-25).
Figure 21:
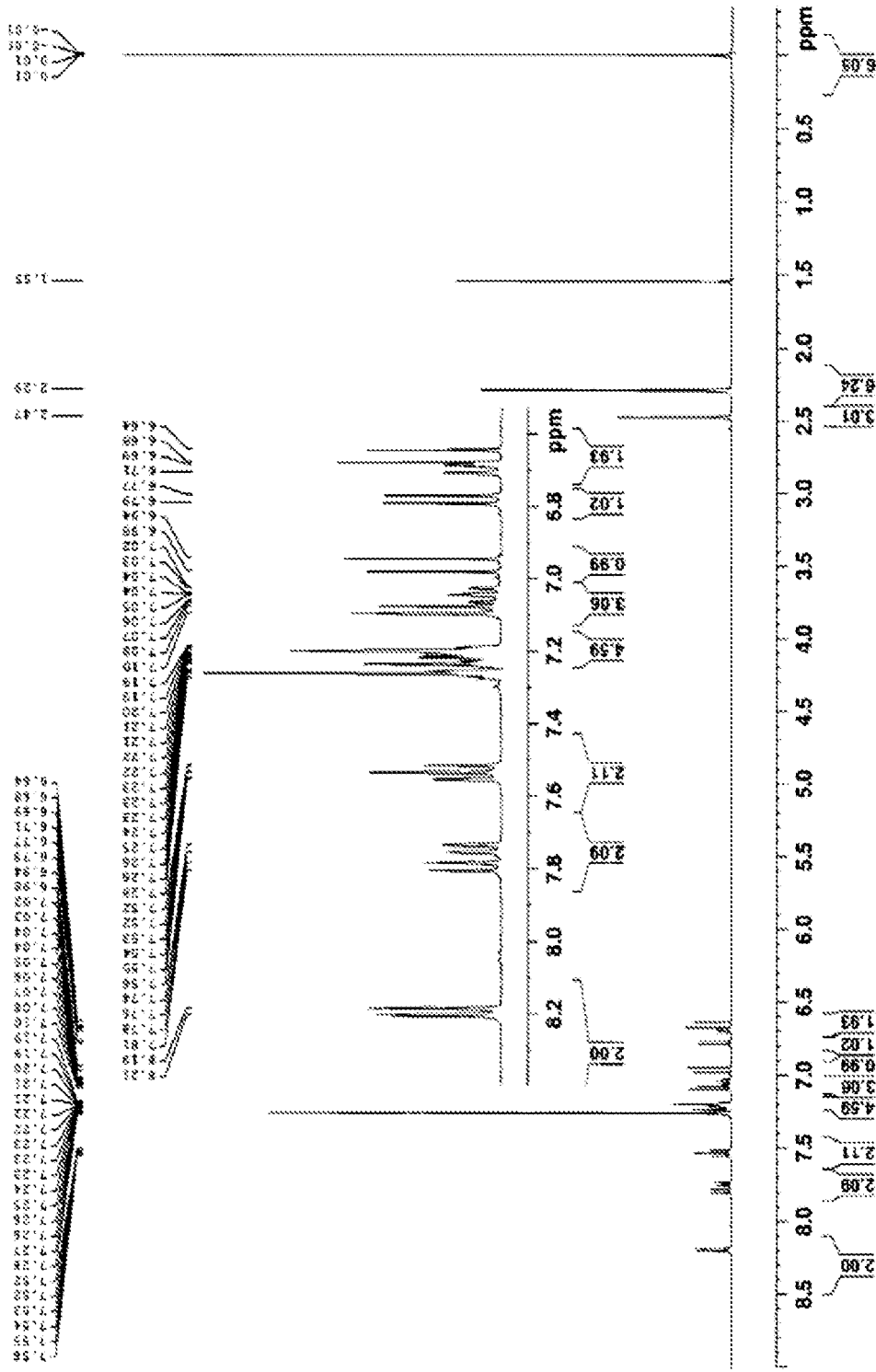
FIG. 21 is a $^1$H•NMR spectrum of a compound (D-26).

$^1$H NMR spectrum (400 MHz, DMSO) is shown in FIG. 17.

MS(ESI+)m/z: 656.5 ([M+H]+)

Compounds (D-22) to (D-32) were synthesized according to the following scheme with reference to the synthesis of the compounds (D-1) to (D-21).

FIGS. 18 to 21 show $^1$H NMR spectra (400 MHz, DMSO) of the compound (D-22) and the compounds (D-24) to (D-26), respectively.

Comparative compounds (R-1), (R-2), (R-3), and (R-4) are disclosed in JP2009-167348A, and a comparative compound (R-5) is disclosed in J. Am. Chem. Soc. 73, 1951, 5326-5330 and a comparative compound (R-6) were synthesized with reference to JP2016-188363A.

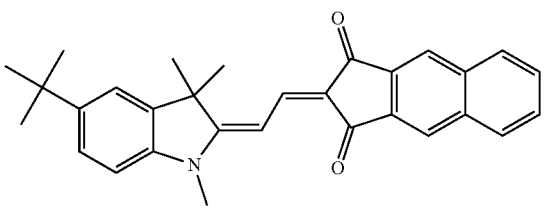

D-1

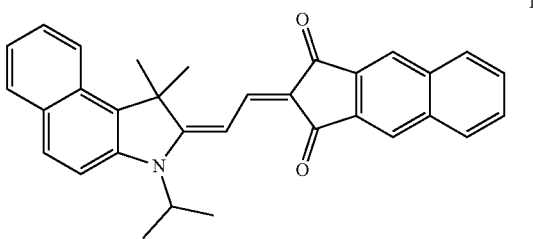

D-2

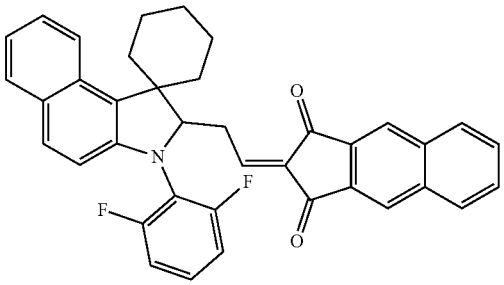

D-3

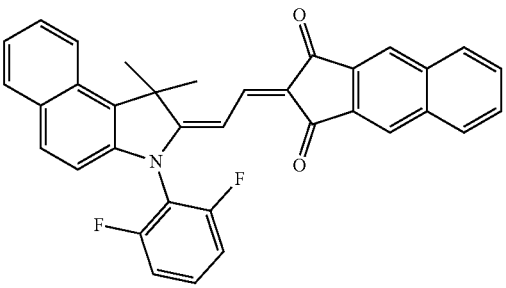

D-4

D-5
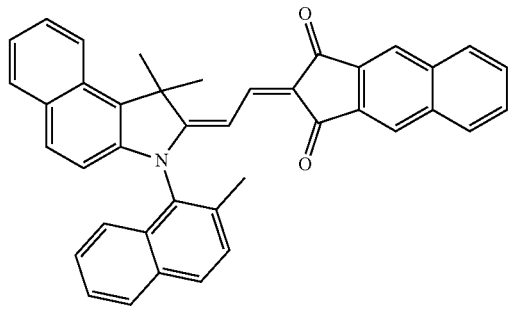
D-6
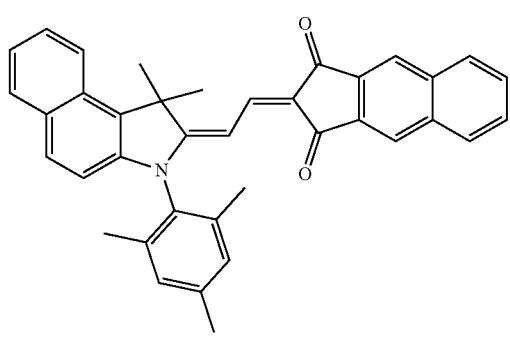
D-7
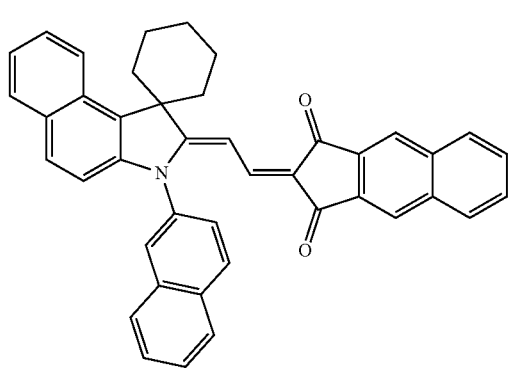
D-8
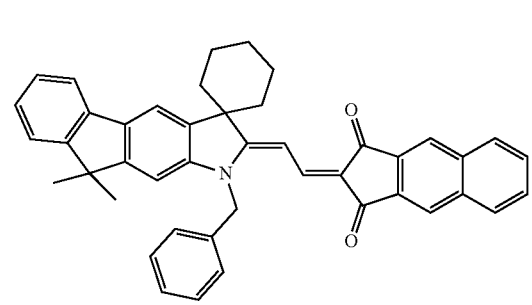
D-9
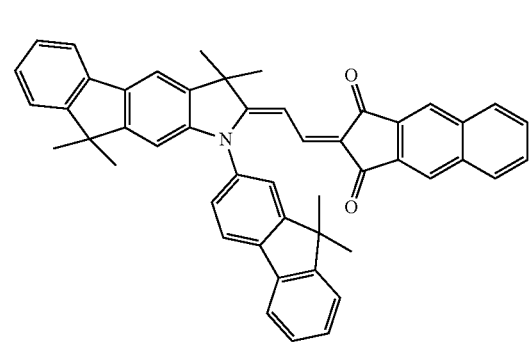
D-10
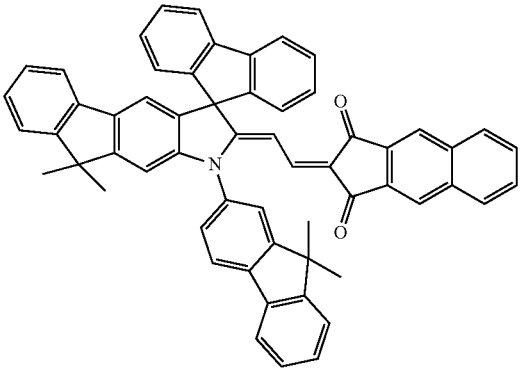
D-11
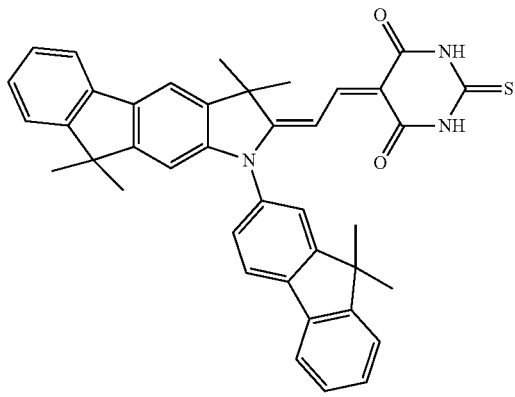
D-12
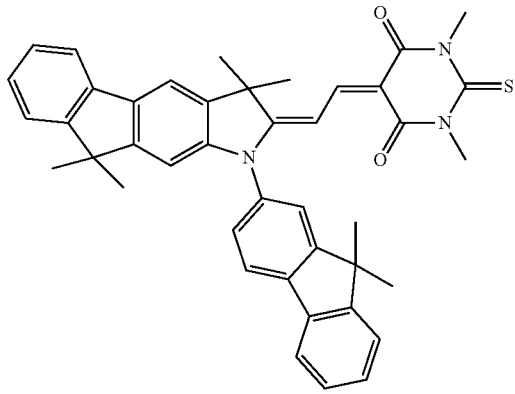
D-13
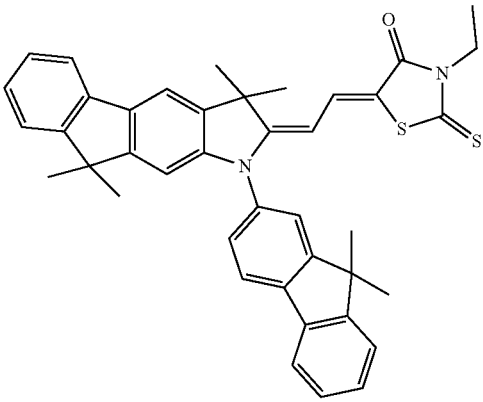

D-14
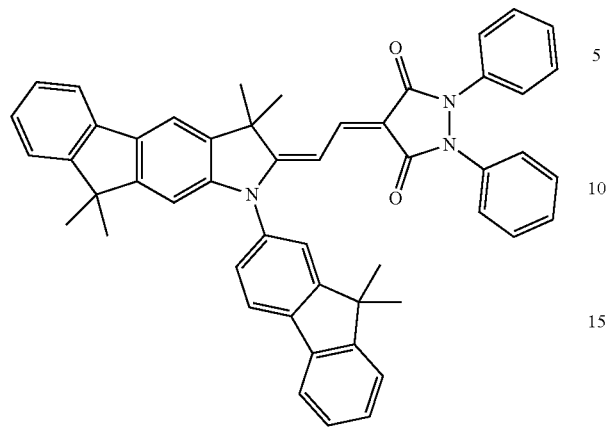
D-19
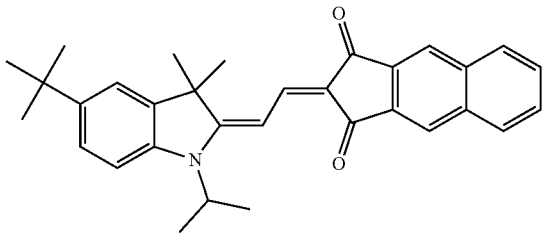
D-15
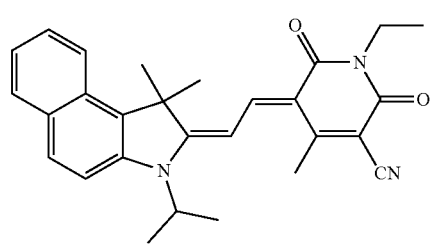
D-16
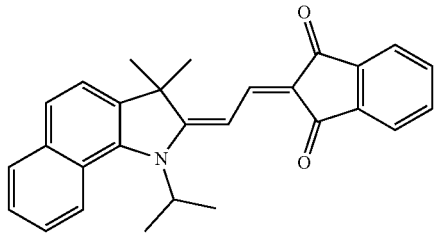
D-20
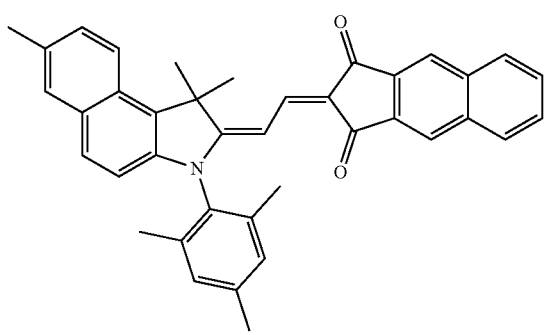
D-17
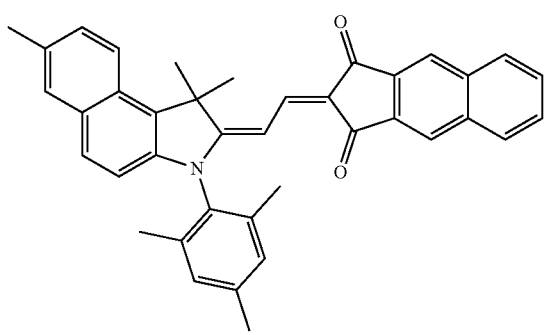
D-21
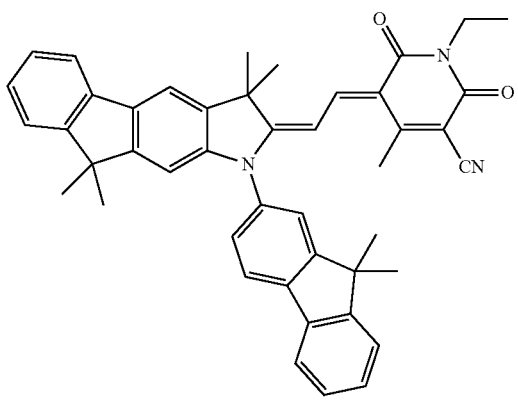
D-18
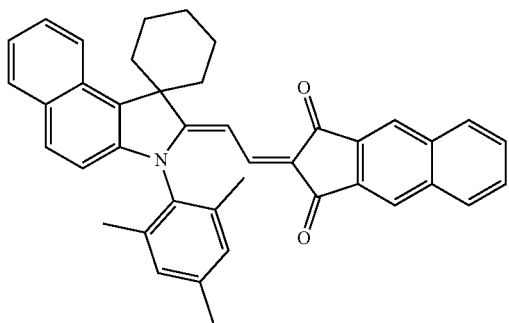
D-22
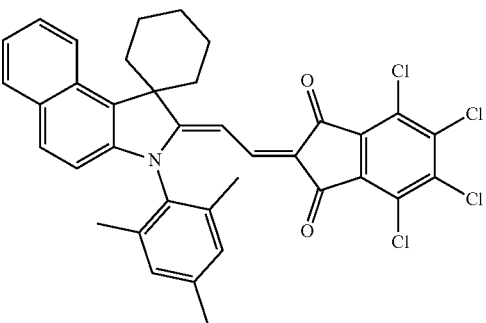

-continued
D-23
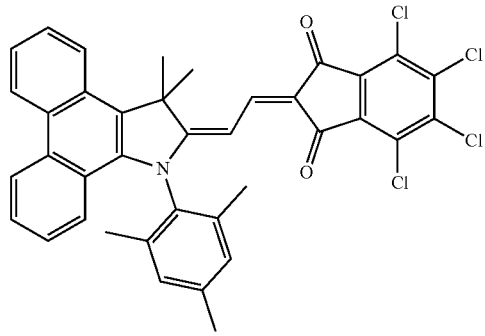
D-24
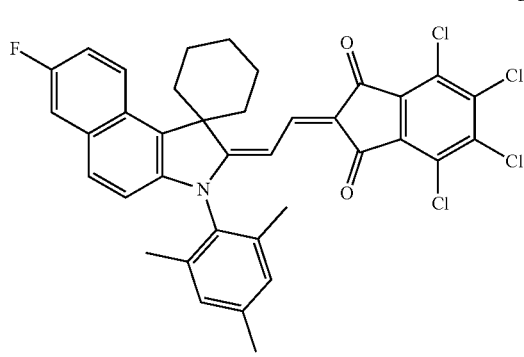
D-25
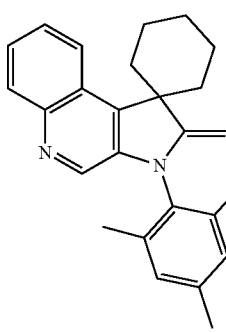
D-26
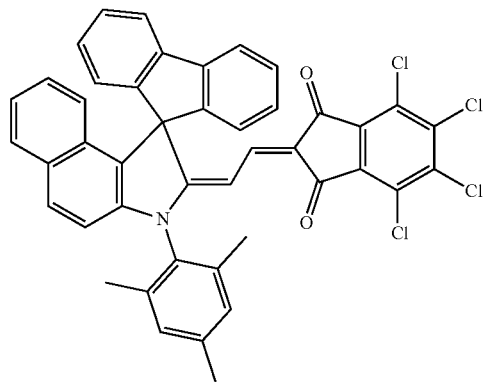
-continued
D-27
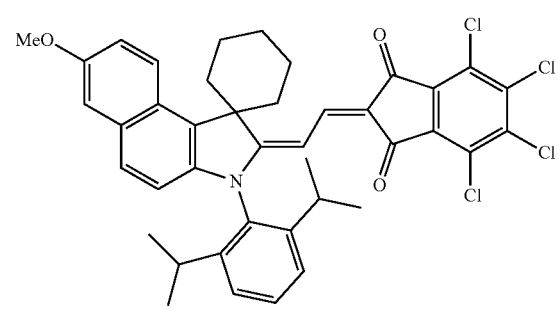
D-28
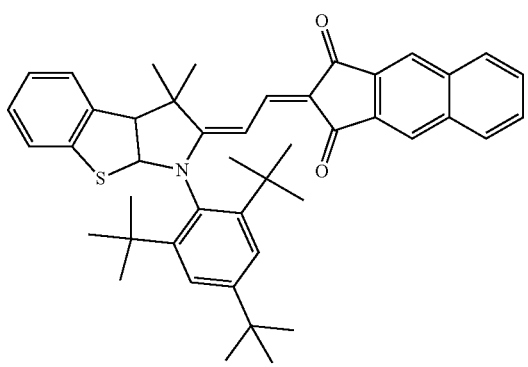
D-29
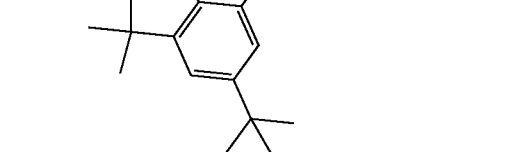
D-30
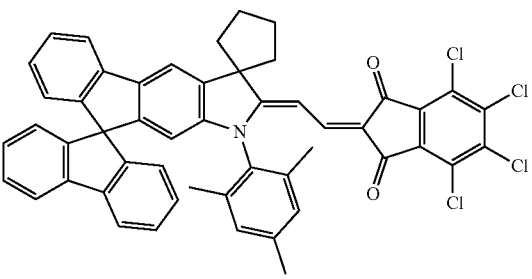
D-31
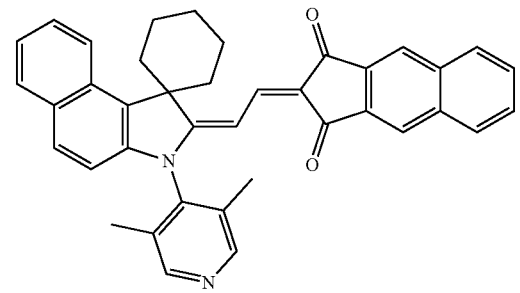

D-32

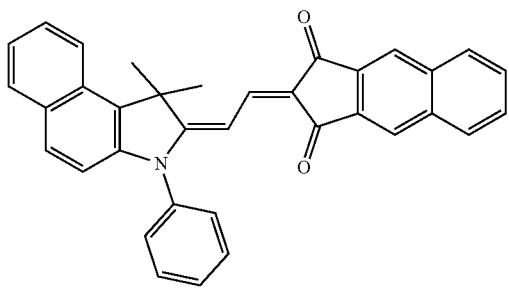

R-1

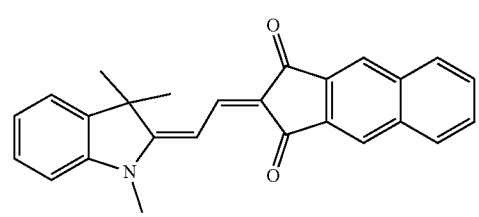

R-2

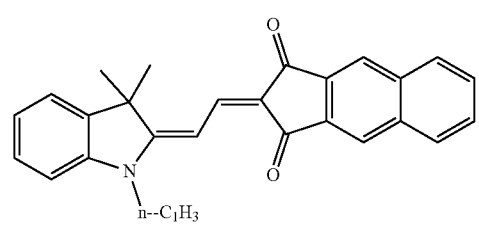

R-3

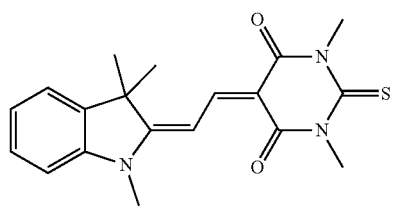

R-4

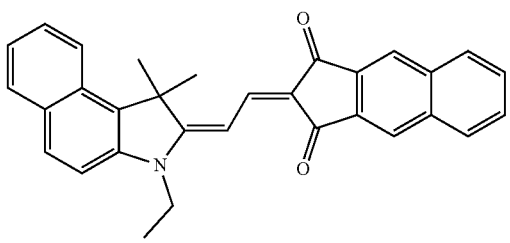

R-5

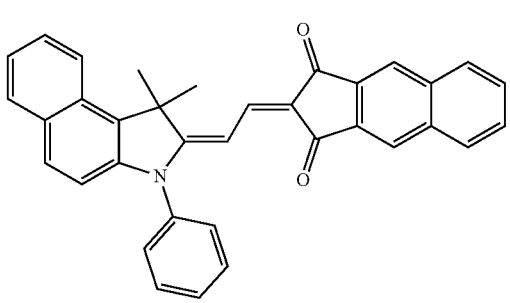

R-6

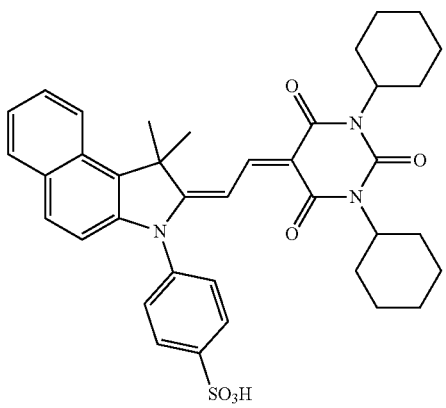

<Examples and Comparative Examples: Production of Photoelectric Conversion Element>

The photoelectric conversion element of the form of FIG. 1 was produced using the obtained compound. Here, the photoelectric conversion element includes a lower electrode 11, an electron blocking film 16A, a photoelectric conversion film 12, and an upper electrode 15.

Specifically, an amorphous ITO was formed into a film on the glass substrate by the sputtering method to form the lower electrode 11 (a thickness: 30 nm). Furthermore, the compound (EB-1) was formed into a film on the lower electrode 11 by the vacuum thermal vapor deposition method to form the electron blocking film 16A (a thickness: 30 nm).

Furthermore, the compound (D-1) and the fullerene ($C_{60}$) were subjected to co-vapor deposition by the vacuum evaporation method so as to be respectively 100 nm in terms of single layer on the electron blocking film 16A to form a film in a state where the temperature of the substrate was controlled to 25° C., and the photoelectric conversion film 12 having the bulk hetero structure of 200 nm was formed.

Furthermore, amorphous ITO was formed into a film on the photoelectric conversion film 12 by a sputtering method to form the upper electrode 15 (the transparent conductive film) (the thickness: 10 nm). After the SiO film was formed as the sealing layer on the upper electrode 15 by a vacuum evaporation method, an aluminum oxide ($Al_2O_3$) layer was formed thereon by an atomic layer chemical vapor deposition (ALCVD) method to produce a photoelectric conversion element.

EB-1

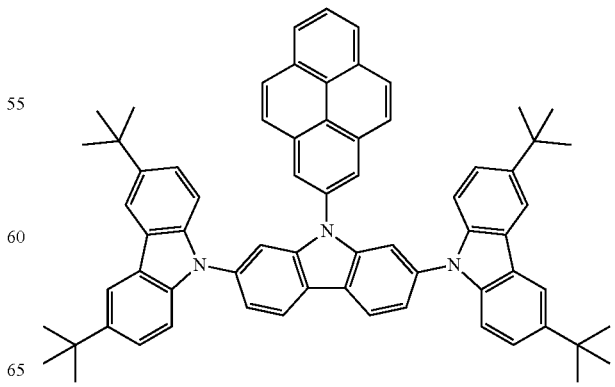

Similarly, the photoelectric conversion elements were produced using the compounds (D-2) to (D-32) and comparative compounds (R-1) to (R-6). However, the comparative compound (R-6) was thermally decomposed during vapor deposition and a photoelectric conversion element could not be produced.

<Evaluation of Photoelectric Conversion Efficiency>

A voltage was applied to each of the photoelectric conversion elements manufactured in Examples and Comparative Examples so that the electric field strength was $1.0 \times 10^5$ V/cm.

Then, light was irradiated from the upper electrode (the transparent conductive film) side to measure the external quantum efficiency at 580 nm. The external quantum efficiency was measured using a constant energy quantum efficiency measuring device (manufactured by Optel). The irradiation light amount was 50 µW/cm$^2$. Further, in order to remove the influence of the reflected light on the surface of the photoelectric conversion element, the measured value of the external quantum efficiency at 580 nm was divided by the light absorption rate at 580 nm to obtain the external quantum efficiency.

The photoelectric conversion efficiency of each photoelectric conversion element with respect to the photoelectric conversion element formed by using the compound (D-1) was evaluated as a relative value.

The relative value of the photoelectric conversion efficiency with respect to the photoelectric conversion element formed by using the compound (D-1) was assumed as "AA" in a case of 1.05 or more, "A" in a case of 1.00 or more and less than 1.05, "B" in a case of 0.95 or more and less than 1.00, "C" in a case of 0.90 or more and less than 0.95, and "D" in a case of less than 0.90. Table 1 shows the results.

Practically, "AA", "A" or "B" is preferable, and "AA" or "A" is more preferable.

<Measurement of Half-Width and Maximum Absorption Wavelength>

The compound (D-1) and the fullerene (C$_0$) were subjected to co-vapor deposition by the vacuum thermal vapor deposition method so as to be respectively 100 nm in terms of single layer to form a film in a state where the temperature of the glass substrate was controlled to 25° C., and the photoelectric conversion film having the bulk hetero structure of 200 nm was formed.

The maximum absorption wavelength and absorption half-width of the photoelectric conversion film were measured using a spectrophotometer U3310 manufactured by Hitachi High-Tech Co., Ltd. The absorption half-width represents the difference between the two wavelengths at which the light absorbance at the maximum absorption wavelength was 0.5 times that of the maximum absorption wavelength (the point at which the light absorbance at 0.5 times the maximum absorption wavelength is at the maximum absorption wavelength was observed at two points on the long wavelength side and the short wavelength side).

The maximum absorption wavelength was evaluated according to the following criteria. The results are summarized in Table 1.

"A": a case where the maximum absorption wavelength is 540 nm or more and less than 570 nm "B": a case where the maximum absorption wavelength is 520 nm or more and less than 540 nm, or a case where the maximum absorption wavelength is 570 nm or more and less than 580 nm "C": a case where the maximum absorption wavelength is 500 nm or more and less than 520 nm, or a case where the maximum absorption wavelength is 580 nm or more and less than 590 nm "D": a case where the maximum absorption wavelength is less than 500 nm or a case where the maximum absorption wavelength is 590 nm or more The absorption half-width was evaluated according to the following criteria. The results are summarized in Table 1.

"AA": a case where the absorption half-width is less than 86 nm

"A": a case where the absorption half-width is 86 nm or more and less than 92 nm "B": a case where the absorption half-width is 92 nm or more and less than 98 nm "C": a case where the absorption half-width is 98 nm or more and less than 100 nm "D": a case where the absorption half-width is 100 nm or more Practically, the absorption half-width is preferably "AA", "A" or "B", and more preferably "AA" or "A".

The compound (D-1) was changed to the compounds (D-2) to (D-32) and the comparative compounds (R-1) to (R-5), and the same evaluations as above were carried out.

In Table 1, the column "A" represents a ring corresponding to A in Formula (1), "B ring" represents a benzene ring, "N ring" represents a naphthalene ring, "F ring" represents a fluorene ring, and "P ring" represents a phenanthrene ring, "Q ring" represents a quinoline ring, and the "BT ring" represents a benzothiophene ring.

The "n" column represents the number corresponding to n in Formula (1).

The column "$R_1$" represents a group corresponding to $R_1$ in Formula (1), "R-1" represents a group represented by Formula (R-1), "R-2" represents a group represented by Formula (R-2), "R-4" represents a group represented by Formula (R-4), "Ar" represents an aryl group (which may be substituted with a substituent), "4A" represents a group represented by Formula (4A), "5A" represents a group represented by Formula (5A), "5B" represents a group represented by Formula (5B), and "Nap" represents a naphthalene ring (which may be substituted with a substituent). In addition, in a case where the group corresponding to $R_1$ corresponds to a plurality of conditions of the above groups, it is described as a group described below. For example, the group corresponding to $R_1$ in the compound (D-6) corresponds to any of "Ar", "4A" and "5A", but only "5A" is shown in the table.

The column "$B_1$" represents a group corresponding to $B_1$ in Formula (1), "B-2" represents a group represented by Formula (B-2), and "J-1" to "J-5" represents groups represented by Formulae (J-1) to (J-5), respectively.

The "total number" represents the total number of carbon atoms contained in $R_1$ to $R_4$ in Formula (1).

The "Formula" column indicates which compound each compound falls under among the compound represented by Formula (1), the compound represented by Formula (2), the compound represented by Formula (2b), the compound represented by Formula (2b-1), and the compound represented by Formula (2b-2). "1" means a compound represented by Formula (1), "2" means a compound represented by Formula (2), "2b" means a compound represented by Formula (2b), "2b-1" means a compound represented by Formula (2b-1), and "2b-2" means a compound represented by Formula (2b-2). In addition, in a case where a compound corresponds to a plurality of Formulae above, it is described as Formula described below. For example, the compounds represented by Formulae (2b-1) and (2b-2) also correspond to the compounds represented by Formulae (1) and (2b), but only "2b-1" and "2b-2" are shown in the table.

The Hammett's substituent constant $\sigma_p$ of the butyl group substituting the benzene ring in the compounds (D-1) and (D-19) was −0.20.

TABLE 1

|  | Compound | | | | | | Evaluation | | |
| --- | --- | --- | --- | --- | --- | --- | --- | --- | --- |
|  | Type | A | n | $R_1$ | $B_1$ | Total number | Formula | Photoelectric conversion efficiency | Maximum absorption wavelength | Absorption half-width |
| Example 1 | D-1 | B ring | 1 | R-1 | B-2 | 7 | 1 | A | B | B |
| Example 2 | D-2 | N ring | — | R-2 | J-1 | 5 | 2b | A | A | A |
| Example 3 | D-3 | N ring | — | Ar | J-1 | 11 | 2b | B | A | AA |
| Example 4 | D-4 | N ring | — | Ar | J-1 | 8 | 2b | B | A | AA |
| Example 5 | D-5 | N ring | — | Nap | J-1 | 13 | 2b-1 | A | A | AA |
| Example 6 | D-6 | N ring | — | 5A | J-1 | 11 | 2b-1 | AA | A | AA |
| Example 7 | D-7 | N ring | — | Nap | J-1 | 15 | 2b-1 | AA | A | A |
| Example 8 | D-8 | F ring | 2 | R-4 | J-1 | 14 | 2b | A | A | A |
| Example 9 | D-9 | F ring | 2 | 5B | J-1 | 19 | 2b | A | A | A |
| Example 10 | D-10 | F ring | 2 | 5B | J-1 | 29 | 2b-2 | A | A | AA |
| Example 11 | D-11 | F ring | 2 | 5B | J-2 | 19 | 2b | AA | A | B |
| Example 12 | D-12 | F ring | 2 | 5B | J-2 | 19 | 2b | B | A | A |
| Example 13 | D-13 | F ring | 2 | 5B | J-3 | 19 | 2b | B | B | A |
| Example 14 | D-14 | F ring | 2 | 5B | J-4 | 19 | 2b | B | B | A |
| Example 15 | D-15 | N ring | — | R-2 | J-5 | 5 | 2b | B | A | B |
| Example 16 | D-16 | N ring | — | R-2 | J-1 | 5 | 2b | A | A | A |
| Example 17 | D-17 | N ring | 1 | 5A | J-1 | 12 | 2b-1 | AA | A | A |
| Example 18 | D-18 | N ring | — | 5A | J-1 | 14 | 2b-1 | AA | A | AA |
| Example 19 | D-19 | B ring | 1 | R-2 | J-1 | 9 | 2 | A | B | A |
| Example 20 | D-20 | N ring | — | R-4 | J-1 | 9 | 2b | A | A | A |
| Example 21 | D-21 | F ring | 2 | 5B | J-5 | 19 | 2b | A | B | B |
| Comparative Example 1 | R-1 | B ring | — | R-1 | B-2 | 3 | — | C | B | C |
| Comparative Example 2 | R-2 | B ring | — | R-1 | B-2 | 6 | — | C | B | C |
| Comparative Example 3 | R-3 | B ring | — | R-1 | — | 3 | — | D | C | C |
| Comparative Example 4 | R-4 | N ring | — | R-1 | B-2 | 4 | — | B | C | D |
| Comparative Example 5 | R-5 | B ring | — | Ar | B-2 | 8 | — | C | B | B |
| Comparative Example 6 | R-6 | N ring | — | Ar | — | 8 | — | Thermal decomposition and element production are not performed during vapor deposition | | |

TABLE 2

|  | Compound | | | | | | Evaluation | | |
| --- | --- | --- | --- | --- | --- | --- | --- | --- | --- |
|  | Type | A | n | $R_1$ | $B_1$ | Total number | Formula | Photoelectric conversion efficiency | Maximum absorption wavelength | Absorption half-width |
| Example 22 | D-22 | N ring | — | 5A | J-1 | 14 | 2b-1 | AA | A | A |
| Example 23 | D-23 | P ring | — | 5A | J-1 | 11 | 2b | A | A | A |
| Example 24 | D-24 | N ring | 1 | 5A | J-1 | 14 | 2b-1 | AA | A | A |
| Example 25 | D-25 | N ring | — | 5A | J-1 | 17 | 2b-1 | A | A | AA |
| Example 26 | D-26 | N ring | — | 5A | J-1 | 21 | 2b-1 | A | A | AA |
| Example 27 | D-27 | N ring | 1 | 5A | J-1 | 18 | 2b-1 | AA | A | A |
| Example 28 | D-28 | Q ring | — | 5A | J-1 | 14 | 2b | A | A | A |
| Example 29 | D-29 | BT ring | — | 5A | J-1 | 20 | 2b | A | A | A |
| Example 30 | D-30 | F ring | 2 | 5A | J-1 | 25 | 2b-2 | A | A | AA |
| Example 31 | D-31 | N ring | — | 4A | J-1 | 12 | 2b-1 | A | A | A |
| Example 32 | D-32 | N ring | — | Ar | J-1 | 8 | 2b | A | A | B |

As shown in Table 1, in the photoelectric conversion element according to the embodiment of the present invention, the half-width of the absorption peak of the photoelectric conversion film was narrow.

In a case where the specific compound is a compound represented by Formula (2) or Formula (2b) and $B_1$ ($B_2$) is represented by Formula (J-1) or (J-2), it was confirmed that the performance of the photoelectric conversion element according to the embodiment of the present invention is better (results of Examples 2 to 12, 16 to 20, 22 to 32 (one or less "B" evaluation in all evaluation items)).

In a case where the specific compound is a compound represented by Formula (2b), $B_1$ ($B_2$) is represented by Formula (J-1) or (J-2), $R_1$ ($Rc_1$) is a group represented by Formula (R-2), a group represented by Formula (R-4), a group represented Formula (4A), or a polycyclic aromatic ring which may have a substituent, it was confirmed that the performance of the photoelectric conversion element according to the embodiment of the present invention is even better (results of Examples 2, 5 to 10, 16 to 18, 20, 22 to 31 (all evaluation items are "A" or higher)).

In a case where the specific compound is a compound represented by Formula (2b-1) or (2b-2), $R_1$ ($Rc_3$) is a group represented by Formula (5A), a group represented by Formula (5B), or a naphthyl group which may have a substituent, it was confirmed that the performance of the photoelectric conversion element according to the embodiment of the present invention is particularly better (results of Examples 5 to 7, 10, 17, 18, 22, and 24 to 27, 30 (all evaluation items are "A" or higher and "AA" evaluation item is present)).

<Production of Imaging Element>

The same imaging element as shown in FIG. 3 was produced using the compounds (D-1) to (D-32).

The photoelectric conversion element functioning as a green photoelectric conversion element was produced by the method described above.

The blue photoelectric conversion element and the red photoelectric conversion element were produced with reference to the description of JP2005-303266A.

In the obtained imaging element, since the absorption peak of the photoelectric conversion film in the photoelectric conversion element according to the embodiment of the present invention has a narrow half-width, light was easily received by the blue photoelectric conversion element and the red photoelectric conversion element, and color separation performance was excellent.

EXPLANATION OF REFERENCES 10a, 10b: photoelectric conversion element
11: conductive film (lower electrode)
12: photoelectric conversion film
15: transparent conductive film (upper electrode)
16A: electron blocking film
16B: positive hole blocking film
20a: imaging element
22: blue photoelectric conversion element
24: red photoelectric conversion element

What is claimed is:

1. A photoelectric conversion element comprising:
a conductive film;
a photoelectric conversion film; and
a transparent conductive film, in this order,
wherein the photoelectric conversion film contains a compound represented by Formula (1),

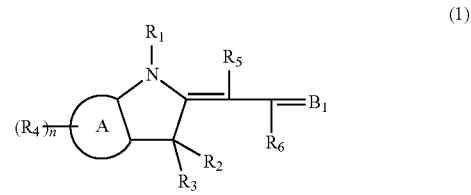

in Formula (1), $R_1$ represents an aryl group which may have a substituent, a heteroaryl group which may have a substituent, a group represented by Formula (R-2), a group represented by Formula (R-3), or a group represented by Formula (R-4),

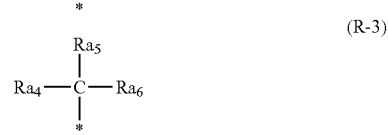

in Formula (R-2), $Ra_2$ and $Ra_3$ each independently represent an alkyl group or an aryl group, $Ra_2$ and $Ra_3$ may bond to each other to form a ring, and * represents a bonding position, in Formula (R-3), $Ra_4$ to $Ra_6$ each independently represent an alkyl group or an aryl group, $Ra_4$ to $Ra_6$ may bond to each other to form a ring, and * represents a bonding position, in Formula (R-4), $Ra_{12}$ represents an aryl group which may have a substituent or a heteroaryl group which may have a substituent, and * represents a bonding position, A represents an aromatic ring, $R_2$ and $R_3$ each independently represent a substituent, $R_2$ and $R_3$ may bond to each other to form a ring, $R_4$ to $R_6$ each independently represent a hydrogen atom or a substituent, n represents an integer of 0 to 18, and in a case where n is 2 or more, a plurality of $R_4$s may bond to each other to form a non-aromatic ring containing no aromatic ring structure, or a fluorene ring, in a case where A is a benzene ring, n is 1 or more, and at least one of $R_4$s represents a substituent having a Hammett's substituent constant $\sigma_p$ of 0.05 or less, the total number of carbon atoms contained in $R_1$ to $R_4$ is 5 or more, in a case where $R_1$ represents an aryl group which may have a substituent, a heteroaryl group which may have a substituent, a group represented by Formula (R-2), a group represented by Formula (R-3), or a group represented by Formula (R-4), $B_1$ represents a group represented by Formula (B-1-1) or a group represented by Formula (B-1-2),

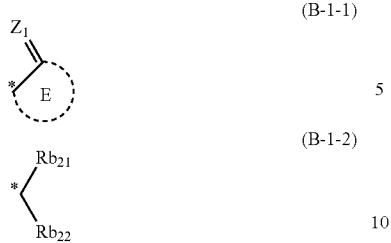

(B-1-1)

(B-1-2)

in Formula (B-1-1), E represents a ring which has at least two carbon atoms and may have a substituent, $Z_1$ represents an oxygen atom, a sulfur atom, $NR_{Z1}$, or $CR_{Z2}R_{Z3}$, $R_{Z1}$ represents a hydrogen atom or a substituent, $R_{Z2}$ and $R_{Z3}$ each independently represent a cyano group or —$COOR_{Z4}$, $R_{Z4}$ represents an alkyl group which may have a substituent, an aryl group which may have a substituent, or a heteroaryl group which may have a substituent, and * represents a bonding position, and in Formula (B-1-2), $Rb_{21}$ and $Rb_{22}$ each independently represent a cyano group or —$COORb_{23}$, and $Rb_{23}$ represents an alkyl group which may have a substituent, an aryl group which may have a substituent, or a heteroaryl group which may have a substituent, where, the compound represented by Formula (1) has none of a carboxy group, a salt of a carboxy group, a phosphoric acid group, a salt of a phosphoric acid group, a sulfonic acid group, or a salt of a sulfonic acid group.

2. The photoelectric conversion element according to claim 1, wherein the compound represented by Formula (1) is a compound represented by Formula (2) or a compound represented by Formula (2b),

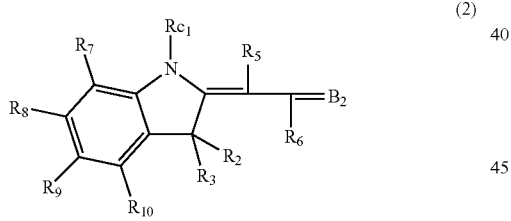

(2)

in Formula (2), $Rc_1$ represents an aryl group which may have a substituent, a heteroaryl group which may have a substituent, a group represented by Formula (R-2), a group represented by Formula (R-3), or a group represented by Formula (R-4), $R_2$ and $R_3$ each independently represent a substituent, $R_2$ and $R_3$ may bond to each other to form a ring, $R_5$ and $R_6$ each independently represent a hydrogen atom or a substituent, $R_7$ to $R_{10}$ each independently represent a hydrogen atom or a substituent, $R_7$ to $R_{10}$ may bond to each other to form a non-aromatic ring containing no aromatic ring structure, at least one of $R_7$ to $R_{10}$ represents a substituent having a Hammett's substituent constant $\sigma_p$ of 0.05 or less, the total number of carbon atoms contained in $Rc_1$, $R_2$, $R_3$, and $R_7$ to $R_{10}$ is 5 or more, and $B_2$ represents a group represented by Formula (B-1-1), where, the compound represented by Formula (2) has none of a carboxy group, a salt of a carboxy group, a phosphoric acid group, a salt of a phosphoric acid group, a sulfonic acid group, or a salt of a sulfonic acid group,

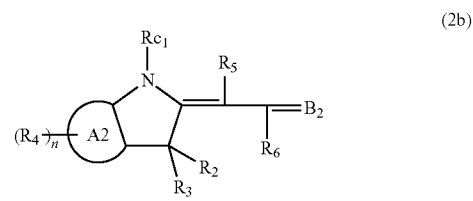

(2b)

in Formula (2b), $Rc_1$ represents an aryl group which may have a substituent, a heteroaryl group which may have a substituent, a group represented by Formula (R-2), a group represented by Formula (R-3), or a group represented by Formula (R-4), $R_2$ and $R_3$ each independently represent a substituent, $R_2$ and $R_3$ may bond to each other to form a ring, and $R_4$ to $R_6$ each independently represent a hydrogen atom or a substituent, and A2 represents a polycyclic aromatic ring which may have a substituent, $B_2$ represents a group represented by Formula (B-1-1), the total number of carbon atoms contained in $Rc_1$ and $R_2$ to $R_4$ is 5 or more, n represents an integer of 0 to 18, and in a case where n is 2 or more, a plurality of $R_4$s may bond to each other to form a non-aromatic ring containing no aromatic ring structure, or a fluorene ring, where, the compound represented by Formula (2b) has none of a carboxy group, a salt of a carboxy group, a phosphoric acid group, a salt of a phosphoric acid group, a sulfonic acid group, or a salt of a sulfonic acid group.

3. The photoelectric conversion element according to claim 2, wherein the groups represented by Formula (B-1-1) in the compounds represented by Formula (2) and Formula (2b) is groups represented by Formulae (J-1) to (J-5),

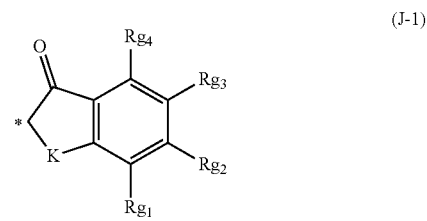

(J-1)

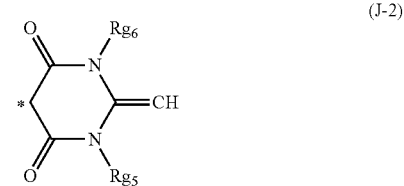

(J-2)

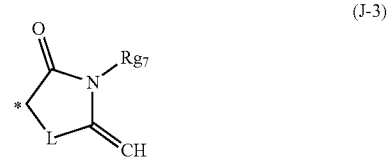

(J-3)

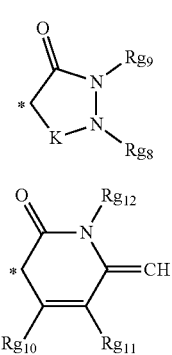

(J-4)

(J-5)

in Formula (J-1), $Rg_1$ to $Rg_4$ each independently represent a hydrogen atom or a substituent, $Rg_1$ to $Rg_4$ may bond to each other to form a ring, K represents —CO—, an oxygen atom, a sulfur atom, a selenium atom, a tellurium atom, —$NRb_1$—, —$CRb_2Rb_3$—, or —$SiRb_4Rb_5$—, and $Rb_1$ to $Rb_5$ each independently represent a hydrogen atom or a substituent, in Formula (J-2), $Rg_5$ and $Rg_6$ each independently represent a hydrogen atom or a substituent, Ch represents =$CRa_7Ra_8$, an oxygen atom, a sulfur atom, a selenium atom, or a tellurium atom, $Ra_7$ and $Ra_8$ each independently represent a hydrogen atom or a substituent, and $Ra_7$ and $Ra_8$ may bond to each other to form a ring, in Formula (J-3), $Rg_7$ represents a hydrogen atom or a substituent, Ch represents =$CRa_7Ra_8$, an oxygen atom, a sulfur atom, a selenium atom, or a tellurium atom, $Ra_7$ and $Ra_8$ each independently represent a hydrogen atom or a substituent, $Ra_7$ and $Ra_8$ may bond to each other to form a ring, and L represents an oxygen atom, a sulfur atom, a selenium atom, or a tellurium atom, in Formula (J-4), $Rg_8$ and $Rg_9$ each independently represent a hydrogen atom or a substituent, $Rg_8$ and $Rg_9$ may bond to each other to form a ring, K represents —CO—, an oxygen atom, a sulfur atom, a selenium atom, a tellurium atom, —$NRb_1$—, —$CRb_2Rb_3$—, or —$SiRb_4Rb_5$—, and $Rb_1$ to $Rb_5$ each independently represent a hydrogen atom or a substituent, and in Formula (J-5), $Rg_{10}$ to $Rg_{12}$ each independently represent a hydrogen atom or a substituent, $Rg_{10}$ and $Rg_{11}$ may bond to each other to form a ring, Ch represents =$CRa_7Ra_8$, an oxygen atom, a sulfur atom, a selenium atom, or a tellurium atom, $Ra_7$ and $Ra_8$ each independently represent a hydrogen atom or a substituent, and $Ra_7$ and $Ra_8$ may bond to each other to form a ring.

4. The photoelectric conversion element according to claim 3,
wherein the compound represented by Formula (1) is the compound represented by Formula (2) or Formula (2b), and
the group represented by Formula (B-1-1) in the compound represented by Formula (2) or Formula (2b) is the group represented by Formula (J-1) or the group represented by Formula (J-2).

5. The photoelectric conversion element according to claim 2,
wherein the compound represented by Formula (1) is the compound represented by Formula (2b), and $Rc_1$ represents the group represented by Formula (R-2), the group represented by Formula (R-3), the group represented by Formula (R-4), a group represented by Formula (4A), or a polycyclic aromatic ring which may have a substituent,

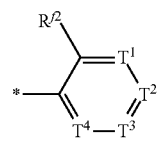

(4A)

in Formula (4A), $T^1$ to $T^4$ each independently represent $CR^{e12}$ or a nitrogen atom, $R^{e12}$ represents a hydrogen atom or a substituent, and $R^{f2}$ represents an alkyl group, a cyano group, an aryl group which may have a substituent, or a heteroaryl group which may have a substituent, and in a case where a plurality of $R^{e12}$s are present in Formula (4A), $R^{e12}$s may be the same as or different from each other, and $R^{e12}$s may bond to each other to form a non-aromatic ring containing no aromatic ring structure.

6. The photoelectric conversion element according to claim 5,
wherein the compound represented by Formula (1) is the compound represented by Formula (2b), and
the group represented by Formula (B-1-1) in the compound represented by Formula (2b) is a group represented by Formula (J-1), and $Rc_1$ represents the group represented by Formula (4A), or a polycyclic aromatic ring which may have a substituent.

7. The photoelectric conversion element according to claim 5, wherein the compound represented by Formula (1) is a compound represented by Formula (2b-1) or a compound represented by Formula (2b-2),

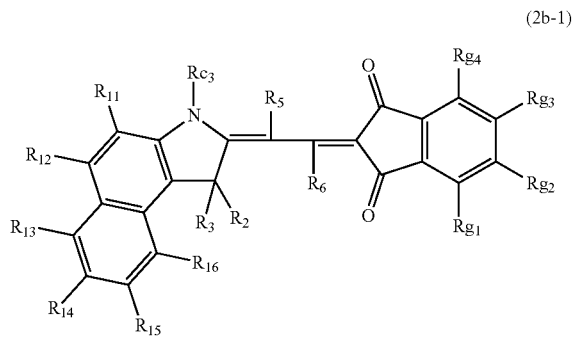

(2b-1)

in Formula (2b-1), $Rc_3$ represents the group represented by Formula (4A) or a polycyclic aromatic ring which may have a substituent, $R_2$ and $R_3$ each independently represent a substituent, $R_2$ and $R_3$ may bond to each other to form a ring, $R_5$ and $R_6$ each independently represent a hydrogen atom or a substituent, $R_{11}$ to $R_{16}$ each independently represent a hydrogen atom or a substituent, $R_{11}$ to $R_{16}$ may bond to each other to form a non-aromatic ring containing no aromatic ring structure or a fluorene ring, $Rg_1$ to $Rg_4$ each independently represent a hydrogen atom or a substituent, and $Rg_1$ to $Rg_4$ may bond to each other to form a ring, and the total number of carbon atoms contained in $Rc_3$, $R_2$, $R_3$, and $R_{11}$ to $R_{16}$ is 5 or more, where, the compound represented by Formula (2b-1) has none of a carboxy group, a salt of a carboxy group, a phosphoric acid group, a salt of a phosphoric acid group, a sulfonic acid group, or a salt of a sulfonic acid group,

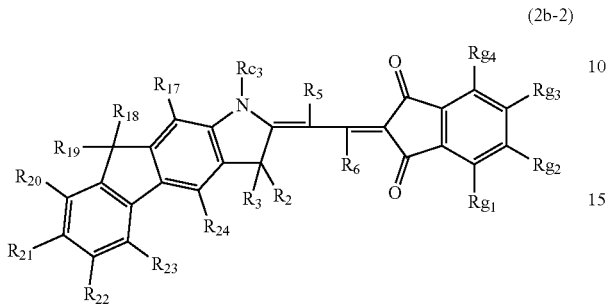

(2b-2)

in Formula (2b-2), $Rc_3$ represents the group represented by Formula (4A) or a polycyclic aromatic ring which may have a substituent, $R_2$ and $R_3$ each independently represent a substituent, $R_2$ and $R_3$ may bond to each other to form a ring, $R_5$ and $R_6$ each independently represent a hydrogen atom or a substituent, $R_{17}$ to $R_{24}$ each independently represent a hydrogen atom or a substituent, $R_{17}$ to $R_{24}$ may bond to each other to form a non-aromatic ring containing no aromatic ring structure or a fluorene ring, $Rg_1$ to $Rg_4$ each independently represent a hydrogen atom or a substituent, $Rg_1$ to $Rg_4$ may bond to each other to form a ring, and the total number of carbon atoms contained in $R_2$ and $R_3$ is 4 or more, and the total number of carbon atoms contained in $Rc_3$, $R_2$, $R_3$, and $R_{17}$ to $R_{24}$ is 5 or more, where, the compound represented by Formula (2b-2) has none of a carboxy group, a salt of a carboxy group, a phosphoric acid group, a salt of a phosphoric acid group, a sulfonic acid group, or a salt of a sulfonic acid group.

8. The photoelectric conversion element according to claim 7, wherein $Rc_3$ represents a group represented by Formula (5A), a group represented by Formula (5B), or a naphthyl group which may have a substituent,

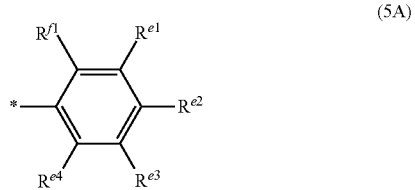

(5A)

in Formula (5A), $R^{e1}$ to $R^{e4}$ each independently represent a hydrogen atom or a substituent, $R^{e1}$ to $R^{e4}$ may bond to each other to form a non-aromatic ring containing no aromatic ring structure, and $R^{f1}$ represents an alkyl group, and

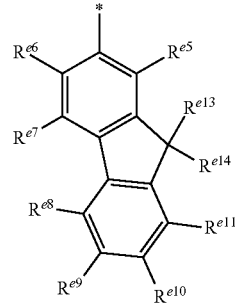

(5B)

in Formula (5B), $R^{e5}$ to $R^{e11}$ and $R^{e13}$ to $R^{e14}$ each independently represent a hydrogen atom or a substituent, and $R^{e5}$ to $R^{e11}$ and $R^{e13}$ to $R^{e14}$ may bond to each other to form a ring.

9. The photoelectric conversion element according to claim 1, wherein the photoelectric conversion film further contains an n-type organic semiconductor, and has a bulk hetero structure formed in a state where the compound represented by Formula (1) and the n-type organic semiconductor are mixed.

10. The photoelectric conversion element according to claim 9, wherein the n-type organic semiconductor contains fullerenes selected from the group consisting of a fullerene and a derivative thereof.

11. The photoelectric conversion element according to claim 1, further comprising one or more interlayers between the conductive film and the transparent conductive film, in addition to the photoelectric conversion film.

12. The photoelectric conversion element according to claim 1, wherein A is an aromatic hydrocarbon ring.

13. An imaging element comprising the photoelectric conversion element according to claim 1.

14. The imaging element according to claim 13, further comprising another photoelectric conversion element that receives light having a wavelength different from a wavelength of light received by the photoelectric conversion element.

15. The imaging element according to claim 14,
wherein the photoelectric conversion element and the other photoelectric conversion element are laminated, and
at least a part of incidence ray is transmitted through the photoelectric conversion element, and then is received by the other photoelectric conversion element.

16. The imaging element according to claim 14,
wherein the photoelectric conversion element is a green photoelectric conversion element, and
the other photoelectric conversion element includes a blue photoelectric conversion element and a red photoelectric conversion element.

17. An optical sensor comprising the photoelectric conversion element according to claim 1.

18. A compound represented by Formula (1),

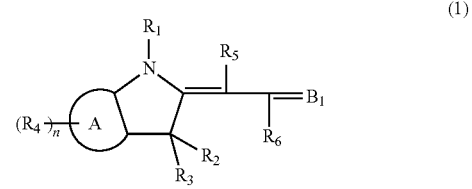

(1)

in Formula (1), $R_1$ represents an aryl group which may have a substituent, a heteroaryl group which may have a substituent, a group represented by Formula (R-2), a group represented by Formula (R-3), or a group represented by Formula (R-4),

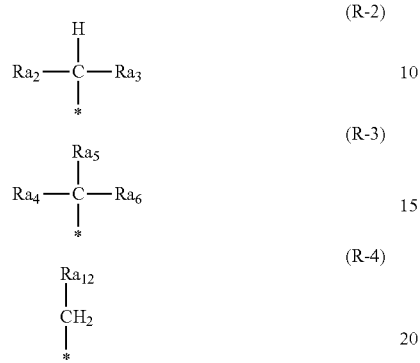

in Formula (R-2), $Ra_2$ and $Ra_3$ each independently represent an alkyl group or an aryl group, $Ra_2$ and $Ra_3$ may bond to each other to form a ring, and * represents a bonding position, in Formula (R-3), $Ra_4$ to $Ra_6$ each independently represent an alkyl group or an aryl group, $Ra_4$ to $Ra_6$ may bond to each other to form a ring, and * represents a bonding position, in Formula (R-4), $Ra_{12}$ represents an aryl group which may have a substituent or a heteroaryl group which may have a substituent, and * represents a bonding position, A represents an aromatic ring, $R_2$ and $R_3$ each independently represent a substituent, $R_2$ and $R_3$ may bond to each other to form a ring, $R_4$ to $R_6$ each independently represent a hydrogen atom or a substituent, n represents an integer of 0 to 18, and in a case where n is 2 or more, a plurality of $R_4$s may bond to each other to form a non-aromatic ring containing no aromatic ring structure, or a fluorene ring, in a case where A is a benzene ring, n is 1 or more, at least one of $R_4$s represents a substituent having a Hammett's substituent constant $\sigma_p$ of 0.05 or less, the total number of carbon atoms contained in $R_1$ to $R_4$ is 5 or more, in a case where $R_1$ represents an aryl group which may have a substituent, a heteroaryl group which may have a substituent, a group represented by Formula (R-2), a group represented by Formula (R-3), or a group represented by Formula (R-4), $B_1$ represents a group represented by Formula (B-1-1) or a group represented by Formula (B-1-2),

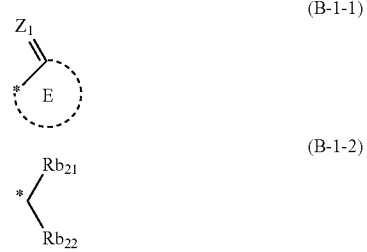

in Formula (B-1-1), E represents a ring which has at least two carbon atoms and may have a substituent, $Z_1$ represents an oxygen atom, a sulfur atom, $NR_{Z1}$, or $CR_{Z2}R_{Z3}$, $R_{Z1}$ represents a hydrogen atom or a substituent, $R_{Z2}$ and $R_{Z3}$ each independently represent a cyano group or $—COOR_{Z4}$, $R_{Z4}$ represents an alkyl group which may have a substituent, an aryl group which may have a substituent, or a heteroaryl group which may have a substituent, and * represents a bonding position, and in Formula (B-1-2), $Rb_{21}$ and $Rb_{22}$ each independently represent a cyano group or $—COORb_{23}$, and $Rb_{23}$ represents an alkyl group which may have a substituent, an aryl group which may have a substituent, or a heteroaryl group which may have a substituent, where, the compound represented by Formula (1) has none of a carboxy group, a salt of a carboxy group, a phosphoric acid group, a salt of a phosphoric acid group, a sulfonic acid group, or a salt of a sulfonic acid group.

19. The compound according to claim 18, which is the compound represented by Formula (2) or a compound represented by Formula (2b),

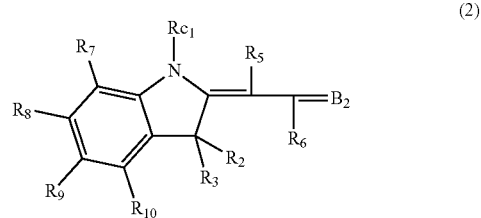

in Formula (2), $Rc_1$ represents an aryl group which may have a substituent, a heteroaryl group which may have a substituent, a group represented by Formula (R-2), a group represented by Formula (R-3), or a group represented by Formula (R-4), $R_2$ and $R_3$ each independently represent a substituent, $R_2$ and $R_3$ may bond to each other to form a ring, $R_5$ and $R_6$ each independently represent a hydrogen atom or a substituent, $R_7$ to $R_{10}$ each independently represent a hydrogen atom or a substituent, $R_7$ to $R_{10}$ may bond to each other to form a non-aromatic ring containing no aromatic ring structure, at least one of $R_7$ to $R_{10}$ represents a substituent having a Hammett's substituent constant $\sigma_p$ of 0.05 or less, the total number of carbon atoms contained in $Rc_1$, $R_2$, $R_3$, and $R_7$ to $R_{10}$ is 5 or more, and $B_2$ represents a group represented by Formula (B-1-1), where, the compound represented by Formula (2) has none of a carboxy group, a salt of a carboxy group, a phosphoric acid group, a salt of a phosphoric acid group, a sulfonic acid group, or a salt of a sulfonic acid group,

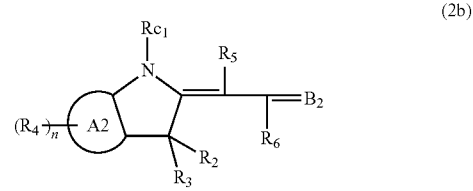

in Formula (2b), $Rc_1$ represents an aryl group which may have a substituent, a heteroaryl group which may have a substituent, a group represented by Formula (R-2), a group represented by Formula (R-3), or a group represented by Formula (R-4), $R_2$ and $R_3$ each independently represent a substituent, $R_2$ and $R_3$ may bond to each other to form a ring, and $R_4$ to $R_6$ each independently represent a hydrogen atom or a substituent, and A2 represents a polycyclic aromatic ring which may have a substituent, $B_2$ represents a group represented by Formula (B-1-1), the total number of carbon atoms contained in $Rc_1$ and $R_2$ to $R_4$ is 5 or more, n represents an integer of 0 to 18, and in a case where n is 2 or more, a plurality of $R_4$s may bond to each other to form a non-aromatic ring containing no aromatic ring structure, or a fluorene ring, where, the compound represented by Formula (2b) has none of a carboxy group, a salt of a carboxy group, a phosphoric acid group, a salt of a phosphoric acid group, a sulfonic acid group, or a salt of a sulfonic acid group.

20. The compound according to claim 19, which is the compound represented by Formula (2b) and $Rc_1$ represents the group represented by Formula (R-2), the group represented by Formula (R-3), the group represented by Formula (R-4), a group represented by Formula (4A), or a polycyclic aromatic ring which may have a substituent,

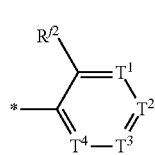

(4A)

in Formula (4A), $T^1$ to $T^4$ each independently represent $CR^{e12}$ or a nitrogen atom, $R^{e12}$ represents a hydrogen atom or a substituent, $R^{f2}$ represents an alkyl group, a cyano group, an aryl group which may have a substituent, or a heteroaryl group which may have a substituent, and in a case where a plurality of $R^{e12}$s are present in Formula (4A), $R^{e12}$s may be the same as or different from each other, and $R^{e12}$s may bond to each other to form a non-aromatic ring containing no aromatic ring structure.

21. The compound according to claim 20, which is a compound represented by Formula (2b-1) or a compound represented by Formula (2b-2),

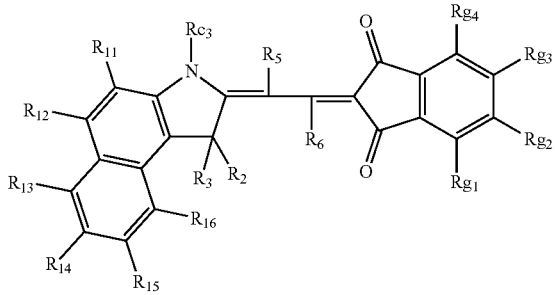

(2b-1)

in Formula (2b-1), $Rc_3$ represents the group represented by Formula (4A) or a polycyclic aromatic ring which may have a substituent, $R_2$ and $R_3$ each independently represent a substituent, $R_2$ and $R_3$ may bond to each other to form a ring, $R_5$ and $R_6$ each independently represent a hydrogen atom or a substituent, $R_{11}$ to $R_{16}$ each independently represent a hydrogen atom or a substituent, $R_{11}$ to $R_{16}$ may bond to each other to form a non-aromatic ring containing no aromatic ring structure or a fluorene ring, $Rg_1$ to $Rg_4$ each independently represent a hydrogen atom or a substituent, and $Rg_1$ to $Rg_4$ may bond to each other to form a ring, and the total number of carbon atoms contained in $Rc_3$, $R_2$, $R_3$, and $R_{11}$ to $R_{16}$ is 5 or more, where, the compound represented by Formula (2b-1) has none of a carboxy group, a salt of a carboxy group, a phosphoric acid group, a salt of a phosphoric acid group, a sulfonic acid group, or a salt of a sulfonic acid group,

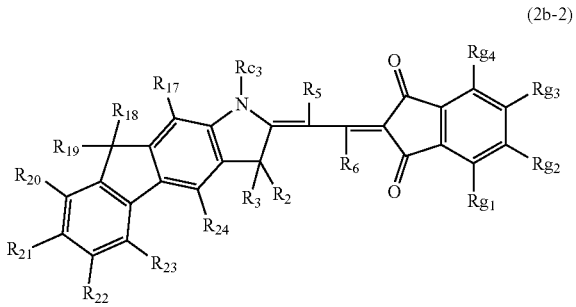

(2b-2)

in Formula (2b-2), $Rc_3$ represents the group represented by Formula (4A) or a polycyclic aromatic ring which may have a substituent, $R_2$ and $R_3$ each independently represent a substituent, $R_2$ and $R_3$ may bond to each other to form a ring, $R_5$ and $R_6$ each independently represent a hydrogen atom or a substituent, $R_{17}$ to $R_{24}$ each independently represent a hydrogen atom or a substituent, $R_{17}$ to $R_{24}$ may bond to each other to form a non-aromatic ring containing no aromatic ring structure or a fluorene ring, $Rg_1$ to $Rg_4$ each independently represent a hydrogen atom or a substituent, $Rg_1$ to $Rg_4$ may bond to each other to form a ring, and the total number of carbon atoms contained in $R_2$ and $R_3$ is 4 or more, and the total number of carbon atoms contained in $Rc_3$, $R_2$, $R_3$, and $R_{17}$ to $R_{24}$ is 5 or more, where, the compound represented by Formula (2b-2) has none of a carboxy group, a salt of a carboxy group, a phosphoric acid group, a salt of a phosphoric acid group, a sulfonic acid group, or a salt of a sulfonic acid group.

* * * * *